(12) United States Patent
Wang et al.

(10) Patent No.: US 7,560,269 B2
(45) Date of Patent: Jul. 14, 2009

(54) REAL TIME ELECTRONIC CELL SENSING SYSTEM AND APPLICATIONS FOR CYTOTOXICITY PROFILING AND COMPOUND ASSAYS

(75) Inventors: Xiaobo Wang, San Diego, CA (US); Xiao Xu, San Diego, CA (US); Yama Abassi, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 714 days.

(21) Appl. No.: 11/055,639

(22) Filed: Feb. 9, 2005

(65) Prior Publication Data

US 2005/0213374 A1     Sep. 29, 2005

Related U.S. Application Data

(63) Continuation-in-part of application No. 10/987,732, filed on Nov. 12, 2004, now Pat. No. 7,192,752, and a continuation-in-part of application No. 10/705,447, filed on Nov. 10, 2003, now Pat. No. 7,470,533, which is a continuation-in-part of application No. 10/705,615, filed on Nov. 10, 2003, now Pat. No. 7,459,303.

(60) Provisional application No. 60/519,567, filed on Nov. 12, 2003, provisional application No. 60/397,749, (Continued)

(51) Int. Cl.
*C12M 1/42*     (2006.01)
*C12M 1/34*     (2006.01)
*C12M 3/00*     (2006.01)
*C12N 13/00*    (2006.01)

(52) U.S. Cl. .............. 435/285.2; 435/288.4; 435/173.1; 435/173.4; 435/173.5; 435/173.8; 435/287.2; 435/288.2; 435/288.3

(58) Field of Classification Search .............. 435/285.2, 435/173.4, 288.4, 173.1, 173.5, 173.8, 287.2, 435/288.2, 288.3
See application file for complete search history.

(56) References Cited

U.S. PATENT DOCUMENTS 2,656,508 A     10/1953     Coulter (Continued)

FOREIGN PATENT DOCUMENTS

EP     1 138 758 A1     4/2001

(Continued)

OTHER PUBLICATIONS

Wegner et al. Electric Cell-Substrate Impedance Sensing (ECIS) as a Noninvasive Means to Monitor the Kinetics of Cell Spreading to Artificial Surfaces. Experimental Cell Research 259, 158-166 (2000).

(Continued)

*Primary Examiner*—William H Beisner
*Assistant Examiner*—Nathan A Bowers
(74) *Attorney, Agent, or Firm*—Biotech Beach Law Group, PC; Raymond Wagenknecht

(57) ABSTRACT

The present invention includes devices, systems, and methods for assaying cells using cell-substrate impedance monitoring. In one aspect, the invention provides cell-substrate impedance monitoring devices that comprise electrode arrays on a nonconducting substrate, in which each of the arrays has an approximately uniform electrode resistance across the entire array. In another aspect, the invention provides cell-substrate monitoring systems comprising one or more cell-substrate monitoring devices comprising multiple wells each having an electrode array, an impedance analyzer, a device station that connects arrays of individual wells to the impedance analyzer, and software for controlling the device station and impedance analyzer. In another aspect, the invention provides cellular assays that use impedance monitoring to detect changes in cell behavior or state. The methods can be used to test the effects of compounds on cells, such as in cytotoxicity assays. Methods of cytotoxicity profiling of compounds are also provided.

19 Claims, 35 Drawing Sheets

Related U.S. Application Data

(60) filed on Jul. 20, 2002, provisional application No. 60/435,400, filed on Dec. 20, 2002, provisional application No. 60/469,572, filed on May 9, 2003, provisional application No. 60/542,927, filed on Feb. 9, 2004, provisional application No. 60/548,713, filed on Feb. 27, 2004, provisional application No. 60/614,601, filed on Sep. 29, 2004.

(56) References Cited

U.S. PATENT DOCUMENTS

| | | |
|---|---|---|
| 3,259,842 A | 7/1966 | Coulter et al. |
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A * | 3/1991 | Taylor et al. ............ 435/4 |
| 5,134,070 A | 7/1992 | Casnig |
| 5,187,096 A | 2/1993 | Giaever et al. |
| 5,218,312 A | 6/1993 | Moro |
| 5,278,048 A | 1/1994 | Parce et al. |
| 5,284,753 A | 2/1994 | Goodwin |
| 5,514,555 A | 5/1996 | Springer et al. |
| 5,563,067 A | 10/1996 | Sugihara et al. |
| 5,601,997 A | 2/1997 | Tchao et al. |
| 5,622,872 A | 4/1997 | Ribi |
| 5,626,734 A | 5/1997 | Docoslis et al. |
| 5,643,742 A | 7/1997 | Malin et al. |
| 5,766,934 A | 6/1998 | Guiseppi-Elie |
| 5,801,055 A | 9/1998 | Henderson |
| 5,810,725 A | 9/1998 | Sugihara et al. |
| 5,851,489 A | 12/1998 | Wolf et al. |
| 5,981,268 A | 11/1999 | Kovacs et al. |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| RE37,977 E | 2/2003 | Sugihara et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat |
| RE38,323 E | 11/2003 | Sugihara et al. |
| 6,649,402 B2 * | 11/2003 | Van der Weide et al. . 435/288.4 |
| 6,686,193 B2 | 2/2004 | Maher et al. |
| 6,716,620 B2 | 4/2004 | Bashir et al. |
| 6,723,523 B2 | 4/2004 | Lynes et al. |
| 7,192,752 B2 | 3/2007 | Xu et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 * | 7/2002 | Chan et al. ............ 435/7.1 |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0116447 A1 | 6/2003 | Surridge et al. |
| 2003/0143625 A1 * | 7/2003 | Martin et al. ............ 435/6 |
| 2003/0157587 A1 | 8/2003 | Gomez et al. |
| 2003/0166015 A1 | 9/2003 | Zarowitz et al. |
| 2004/0091397 A1 | 5/2004 | Picard |
| 2004/0146849 A1 | 7/2004 | Huang et al. |
| 2005/0014130 A1 | 1/2005 | Liu et al. |

FOREIGN PATENT DOCUMENTS

| | | |
|---|---|---|
| EP | 1195432 B1 | 9/2004 |
| WO | 96/01836 | 1/1996 |
| WO | 99/66329 | 12/1999 |
| WO | 00/71669 | 11/2000 |
| WO | 01/25769 | 4/2001 |
| WO | 01/38873 | 5/2001 |
| WO | 02/04943 | 1/2002 |
| WO | 02/42766 | 5/2002 |
| WO | 03/016887 | 2/2003 |
| WO | 2005/005979 | 1/2005 |

OTHER PUBLICATIONS

Aravanis et al. A genetically engineered cell-based biosensor for functional classification of agents. Biosensors & Bioelectronics 16:571-577 (2001).

Baumann et al. Microelectronic sensor system for microphysiological application on living cells. Sensors & Accuators B55:77-89 (1999).

Becker et al, Separation of human breast cancer cells from blood by differential dielectric affinity. Cell Biology. 92:960-964 (1995).

Berens et al, The role of extracellular matrix in human astrocytoma migration and proliferation studied in a microliter scale assay. Clin. Exp. Metastasis 12:405-415 (1994).

Bergveld, A critical evaluation of direct electrical protein detection methods, Biosensors& Bioelectronics. 6:55-72 (1991).

Burns et al, Neutrophil Transendothelial Migration Is Independent of Tight Junctions and Occurs Preferentially at Tricellular Corners. Journal of Immunology 2893-2903 (1997).

Duan et al, Separation-Free Sandwich Enzyme Immnoassays Using Microporous Gold Electrodes and Self-Assembled Monolayer/Immobilized Capture Antibodies, Anal. Chem. 66:1369-1377 (1994).

Connolly et al., An extracellular microelectrode array for monitoring electrogenic cells in culture Biosensors & Bioelectronics 5: 223-234 (1990).

Ehret et al, Monitoring of cellular behaviour by impedance measurements on interdigitated electrode structures. Biosensors and Bioelectronics 12(1) :29-41 (1997).

Ehret et al, On-line control of cellular adhesion with impedance measurements using interdigitated electrode structures, Meidcal & Biolgical Engineering and Computing 36:365-370.

Falk et al, A 48-well Micro Chemotaxis Assembly for Rapid and Accurate Measruement of Leukocyte Migration. J Immunol. Meth. 33:239-247 (1980).

Fuhr et al, Positioning and Manipulation of Cells and Microparticles Using Miniaturized Electric Field Traps and Travelling Waves. Sensors and Materials 7(2):131-146 (1995).

Gaiever et al, Monitoring fibroblast behavior in tissue culture with an applied electric field. Proc. Natl. Acad. Sci 81:3761-3764 (1984).

Giaever et al, Micromotion of mammalian cells measured electrically. Proc. Natl. Acad. USA 88: 7896-7900 (1991).

Hadjout et al., Automated Real-Time Measurement of Chemotactic Cell Motility BioTechniques 31: 1130-1138 (2001).

Henning et al, Approach to a multiparametric sensor-chip-based tumor chemosensitivity assay, Anti-Cancer Drugs 12:21-32 (2001).

Hidalgo et al, Charcaterization of the Human Colon Carcinoma Cell Line (Caco-2) as a Model System for Intestinal Epithelial Permeability. Gastroenterology 96:736-749 (1989).

Huang et al., Dielectrophoretic Cell Separation and Gene Expression Profiling on Microelectronic Chip Arrays. Anal. Chem. 74:3362-3371 (2002).

Keese et al, Real-time impedance assay to follow the invasive activities of metastatic cells in culture. Biotechniques 33:842-850 (2002).

Kleinmann et al., Basement Membrane Complexes with Biological Activity. Biochemistry. 26:312-318 (1986).

Kowolenko et al., Measurement of macrophage adherence and spreading with weak electric fields. Journal of Immunological Methods 127: 71-77 (1990).

Larsen et al, Somatic Cell Counting with Silicon Apertures. Micro Total Analysis Systems 103-106 (2000).

Lo et al, Monitoring motion of confluent cells in tissue culture, Experimental Cell Research 204:102-109 (1993).

Lo et al., pH Changes in pulsed $CO_2$ incubators cause periodic changes in cell morphology Experimental Cell Research 213: 391-397 (1994).

Lo et al., Impedance Analysis of MDCK cells measured by electric cell-substrate impedance sensing Biophysical Journal 69: 2800-2807 (1995).

Luong, et al., Monitoring Motility, Spreading, and Mortality of Adherent Insect Cells Using an Impedance Sensor. Analytical Chemistry 73: 1844-1848 (2001).

Mitra et al, Electric measurements can be used to monitor the attachment and spreading of cells in tissue culture. Biotechniques 11 (4):504-510 (1991).

Miyata et al, New Wound-Healing Model Using Cultured Corneal Endothelial Cells. Jpn. J. Ophthalmol. 34:257-266 (1990).

Neher, Molecular biology meets microelectronics Nature Biotechnology 19: 114 (2001).

Nerurkar et al, The Use of Surfactants to Enhance the Permeability of Peptides Through Caco-2 Cells by Inhbition of an Apically Polarized Efflux System. Pharmaceutical Research 13(4):528-534.

Ong et al, Remote Query Resonant-Circuit Sensors For Monitoring of Bacterial Growth: Application to Food Quality Conrol. Sensors 2:219-222 (2002).

Pancrazio et al, Portable cell-based biosensor system for toxin detection. Sensors and Actuators B 53:179-185 (1998).

Patolsky et al, Detection of single-base DNA mutations by enzyme-amplified electronic transduction. Nature Biotechnology 19:253-257 (2001).

Pethig et al, Positive and negative dielectrophoretic collection of colloidal particles using interdigitated castellated microelectrodes. Appl. Phys. 24:881-888 (1992).

Richards et al, A Modified Microchamber Method For Chemotaxis and Chemokinesis. Immunological Communications 13(1):49-62 (1984).

Rishpon et al, An amperometric enzyme-channeling immunosensor, Biosensors & Bioelectronics, 12(3):195-204.

Simpson et al., Whole-cell biocomputing Trends in Biotechnology 19: 317-323 (2001).

Sohn et al, Capacitance cytometry: Measuring biological cells one by one. Proc. Nat. Acad. Sci. 97(20) 10687-10690 (2000).

Stenger et al., Detection of physiologically active compounds using cell-based biosensors. Trends in Biotechnology 19: 304-309 (2001).

Svetlicic et al., Charge displacement by adhesion and spreading of a cell Bioelectrochemistry 53: 79-86 (2000).

Tiruppathi et al, Electrical method for detection of endothelial cell shape change in time: assessment of endothelial barrier function. Proc Natl Acad Sci USA 89: 7919-7923 (1992).

Wang et al, A theoretical method of electrical field analysis for dielectrophoretic electrode arrays using Green's theorem. Appl. Phys. 1649-1660 (1996).

Wang et al, Selective dielectrophoretic confinement of bioparticles in potential energy wells. Appl. Phys. 26:1278-1285 (1993).

Wang et al, Cell Separation by Dielectrophoretic Field-flow-fractionation. Anal. Chem. 72:832-839 (2000).

Wang et al, Dielectrophoretic Manipulation of Cells with Spiral Electrodes. Biophysical Journal 72:1887-1899 (1997).

Wang et al, Separation of Polystyrene Microbeads Using Dielectrophoretic/Graviational Field-Flow-Fractionation. Biophysical Journal 74:2689-2701 (1998).

Wang et al., Electronic Manipulation of Cells on Microchip-Based Devices. In Biochip Technology (eds.) Hardwood Academic Publishers, PA U.S.A. 135-159.

Warburg, Ueber die Polarisationscapacitat des Platins. Ann. Phy. 6:125-135 (1901).

Wegener et al, Electric cell-substrate impedance sensing system (ECIS) as a noninvasive means to monitor the kinetics of cell spreading to artificial surfaces, Experimental Cell Research, 259:158-166 (2000).

Wolf et al, Monitoring of cellular signalling and metabolism with modular sensor-technique: The PhysioControl10Microsystem (PCM). Biosensors & Bioelectronics 13:501-509 (1998).

Xiao et al, An in-depth Analysis of Electric Cell-Substrate Impedance Sensing To Study the Attachment and Spreading of Mammalian Cells, Anal. Chem 74:1333-1339 (2002).

Yang et al, Cell Separation on Microfabricated Electrodes Using Dielectrophoretic/Gravitational Field-Flow Fractionation. Anal. Chem. 71:911-918 (1999).

http://www.neuroprobe.com/protocol/pt_96a.html.

http://www.bdbiosciences.com/discovery_labware/Products/inserts/BD_Falcon_HTS_fluoroblok_inserts/individual_fluoroblok_inserts/index.html.

http://www.tecan.com/migration_intro1.pdf.

New Products page. Science 298:2409 (2002).

Abstract: Real-Time Impedance Assay to Follow the Invasive Activities of Metastatic Cells in Culture. Biotechniques 33: 842 (2002).

http://www.biophysics.com/pages/front.html.

Cady et al., Electrical Impedance Measurements: Rapid Method for Detecting and Monitoring Microorganisms.

Mohr et al., Performance of a thin film microelectrode array for monitoring electrogenic cells in vitro, Sensors and Actuators B34:265-269. 1996.

Bieberich and Guiseppi-Elie, Biosensors and Bioelectronics, 19:923-931 (2004).

Burnett et al., J. Biomo. Screening, 8(6):660-667 (2003).

Ciambrone et al., J. Biomo. Screening, 9(6):467-480 (2004).

Ehret et al., Med. Biol. Eng. Comput. 36:365-370 (1998).

Ehret et al., Biosensors and Bioelectronics, 12(1):29-41 (1996).

Gutmann et al., Pharamceutical Research, 16(3) :402-407.

Hug, Assay and Drug Dev. Tech., 1(1) :479-488 (2003).

Lin and Huang, J. Micromech. Microeng., 11:542-547 (2001).

Lin et al., Min. For Chem., Bio., & Bioeng., 4:104-108 (2004).

Wegener et al., Eur. J. Physiol., 437:925-934 (1999).

Wolf et al., Biosensors and Bioelectronics, 13:501-509 (1998).

Xiao and Luong, Biotechnol. Prog., 19:1000-1005 (2003).

Xiao et al., Anal. Chem., 74:5748-5753 (2002).

Yamauchi et al., Nuc. Acids Res., 32(22):1-8 (2004).

Loffert et al., QIAGENNews, 4:15-18 (1997).

* cited by examiner

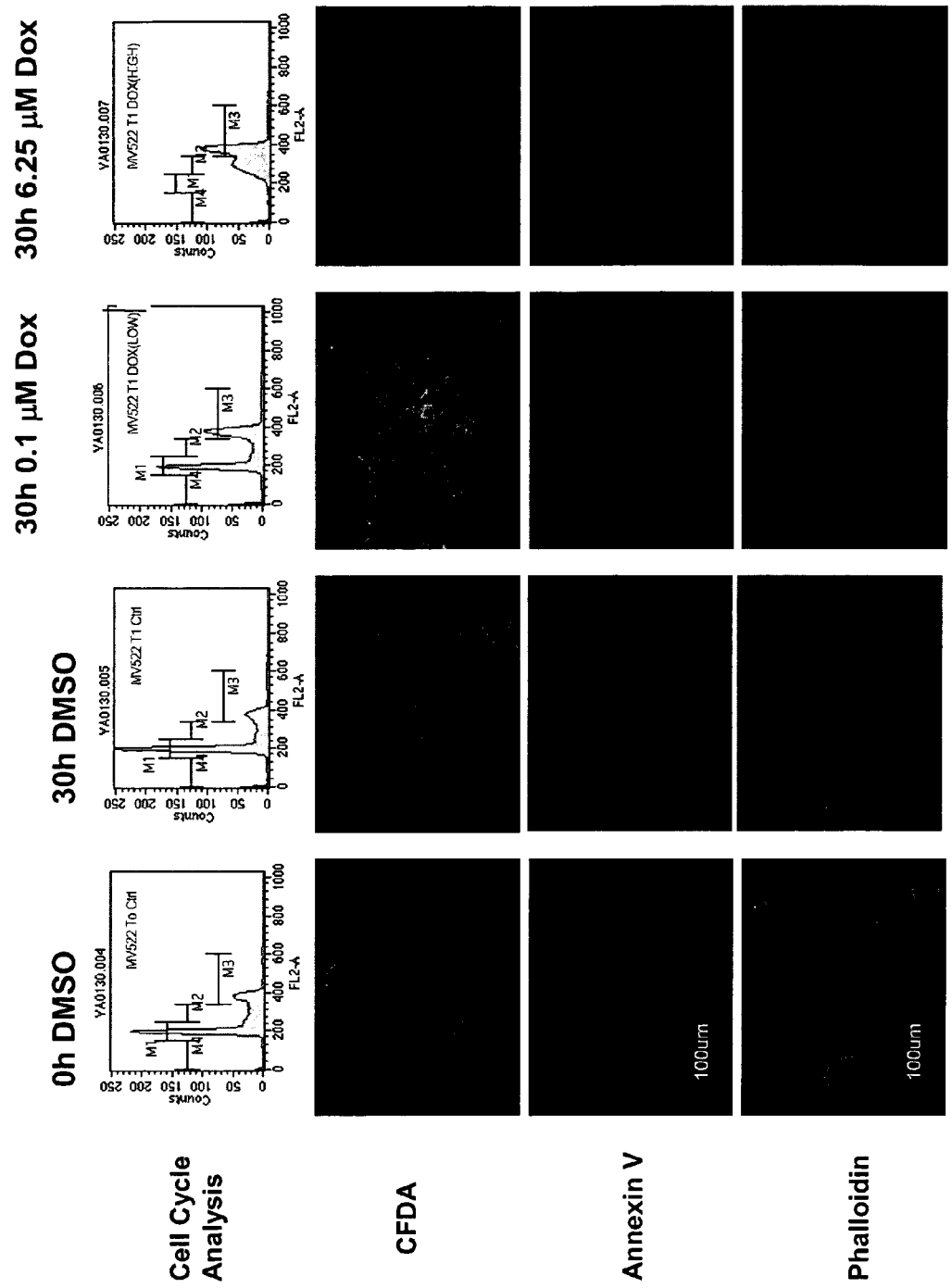
Figure 12.B

Shade-coding Scheme

CCI >> 0.7/DT:

CCI ~ 0.7/DT:

0< CCI < 0.7/DT:

CCI ~ 0:

CCI < 0:

CCI << 0:

REAL TIME ELECTRONIC CELL SENSING SYSTEM AND APPLICATIONS FOR CYTOTOXICITY PROFILING AND COMPOUND ASSAYS

This application is a continuation-in-part of U.S. patent application Ser. No. 10/987,732, entitled "Real time electronic cell sensing system and application for cell based assays" filed Nov. 12, 2004, now U.S. Pat. No. 7,192,752 which claims priority from U.S. Provisional Application 60/519,567, filed Nov. 12, 2003. Parent U.S. patent application Ser. No. 10/987,732 is itself a continuation-in-part of U.S. patent application Ser. No. 10/705,447 filed Nov. 10, 2003, now U.S. Pat. No. 7,470,533 entitled "Impedance Based Devices and Methods for Use in Assays" which claims priority to U.S. Provisional Application 60/397,749, filed Jul. 20, 2002; U.S. Provisional Application 60/435,400, filed Dec. 20, 2002; U.S. Provisional Application 60/469,572, filed May 9, 2003; and PCT application PCT/US03/22557, filed Jul. 18, 2003. All of the applications referred to in this paragraph are incorporated by reference in their entireties herein.

Parent U.S. patent application Ser. No. 10/987,732 is also a continuation-in-part of U.S. patent application Ser. No. 10/705,615, now U.S. Pat. No. 7,459,303 entitled "Impedance Based Apparatuses and Methods for Analyzing Cells and Particles", filed on Nov. 10, 2003, which claims priority to U.S. Provisional Application 60/397,749 filed Jul. 20, 2002; U.S. Provisional Application 60/435,400, filed Dec. 20, 2002; U.S. Provisional Application 60/469,572, filed May 9, 2003; and PCT application PCT/US03/22537, filed Jul. 18, 2003. All of the applications referred to in this paragraph are incorporated by reference in their entireties herein.

This application also claims priority to U.S. Provisional Application 60/542,927 filed Feb. 9, 2004; U.S. Provisional Application 60/548,713, filed Feb. 27, 2004, and U.S. Provisional Application No. 60/614,601, filed Sep. 29, 2004. All of the applications referred to in this paragraph are incorporated by reference in their entireties herein.

BACKGROUND OF THE INVENTION

1. Technical Field

This invention relates to the field of cell-based assays. In particular, the invention provides impedance-based devices, apparatuses and systems for analyzing cells and for conducting cell-based assays.

2. Background Art

Bioelectronics is a progressing interdisciplinary research field that involves the integration of biomatereials with electronic devices. Bioelectronic methods have been used for analyzing cells and assaying biological molecules and cells. In one type of application, cells are cultured on microelectrodes and cell-electrode impedance is measured and determined to monitor cellular changes.

In PCT Application No. PCT/US03/22557, entitled "IMPEDANCE BASED DEVICES AND METHODS FOR USE IN ASSAYS", filed on Jul. 18, 2003, a device for detecting cells and/or molecules on an electrode surface is disclosed. The device detects cells and/or molecules through measurement of impedance changes resulting from the attachment or binding of cells and/or molecules to the electrode surfaces. A number of embodiments of the device is disclosed, together with the apparatuses, system for using such devices to perform certain cell based assays.

In anticancer drug development, the study of the time dependence of cytotoxic and cell proliferation inhibitory effect of a drug is an important element for gaining information to use in the development of clinical dosing strategies. In particular, time dependent IC50's are derived and different time dependent patterns for IC50's are observed (e.g., see Hassan S B, Jonsson E, Larsson R and Karlsson M O in *J. Pharmacology and Experimental Therapeutics,* 2001, Vol. 299, No. 3, pp 1140-1147; Levasseur L M, Slocum H K, Rustum Y M and Greco W R, in *Cancer Research,* 1998, vol. 58, pp 5749-5761.). Typically, these studies used end-point single-measurement assays. Each time point for a dose concentration of drug or compound applied to the cultured cells required a separate experiment. This limits the time resolution and the number of time points of such time-dependent cytotoxicity studies. Thus, new technologies or methods that can provide higher time resolution and permit measurements on many time points are needed.

The present invention further expands the inventions disclosed in PCT Application No. PCT/US03/22557, entitled "IMPEDANCE BASED DEVICES AND METHODS FOR USE IN ASSAYS", filed on Jul. 18, 2003 and disclosed in U.S. patent application Ser. No. 10/705,447, entitled "IMPEDANCE BASED DEVICES AND METHODS FOR USE IN ASSAYS," filed on Nov. 10, 2003. The invention provides a real time cell electronic sensing system for conducting cell-based assays based on measurement of cell-substrate impedance and provides the method for using such a system to perform cell-based assays.

SUMMARY OF THE INVENTION

In one aspect, the present invention is directed to a device for monitoring cell-substrate impedance, which device comprises: a) a nonconducting substrate; b) two or more electrode arrays fabricated on the substrate, where each of the two or more electrode arrays comprises two electrode structures; and c) at least two connection pads, each of which is located on an edge of the substrate. Each electrode array of the device has an approximately uniform electrode resistance distribution across the entire array. The substrate of the device has a surface suitable for cell attachment or growth; where cell attachment or growth on said substrate can result in a detectable change in impedance between or among the electrode structures within each electrode array. In preferred embodiments, each electrode array on the substrate of a device of the present invention is associated with a fluid-impermeable container.

In another aspect, the present invention is directed to a cell-substrate impedance measurement system comprising: a) at least one multiple-well device monitoring cell-substrate impedance, in which at least two of the multiple wells each comprise an electrode array at the bottom of the well; b) an impedance analyzer; c) a device station capable of engaging the one or more multiple-well devices and capable of selecting and electrically connecting electrode arrays within any of the multiple wells in to the impedance analyzer; and d) a software program to control the device station and perform data acquisition and data analysis on impedance values measured by the impedance analyzer. In preferred embodiments of this aspect of the present invention, each electrode array of the multiple-well device is individually addressed.

In yet another aspect, the present invention provides a method for monitoring cell-substrate impedance using a device of the present invention. The method includes: providing a multiple array device of the present invention; connecting said multiple array device to an impedance analyzer; depositing cells on at least one of the two or more arrays of the device; and monitoring cell-substrate impedance on one or more arrays of the device.

In yet another aspect, the present invention provides methods for calculating a Cell Change Index for quantifying and comparing cell-substrate impedance.

In yet another aspect, the present invention provides methods for calculating resistance of electrical traces connecting an array of a cell-substrate monitoring device with a connection pad. Such calculations of electrical trace resistance can be used for calculating Cell Index.

In yet another aspect, the present invention provides a method for monitoring cell-substrate impedance using a cell-substrate impedance measurement system of the present invention. The method includes: providing a cell-substrate impedance measurement system of the present invention, adding cells to at least one well of the multiple-well device that comprises an electrode array, and monitoring cell-substrate impedance from one or more of the wells that comprise cells. Impedance can be monitored at regular or irregular time intervals. In preferred embodiments, cell-substrate impedance is monitored in at least two wells of a multiple-well device.

In yet another aspect, the present invention provides a method for performing real-time cell-based assays investigating the effects of one or more compound on cells, comprising: providing an above described cell-substrate impedance measurement system; introducing cells into at least one well of the system that comprises an electrode array; adding one or more compounds to one or more of the wells containing cells; and monitoring cell-substrate impedance over the electrode array of the one or more wells before and after adding the one or more compounds. Preferably, cell-substrate impedance is monitored at regular or irregular time intervals after adding one or more compounds to the one or more of the wells containing cells. The time dependent impedance change can provide information about time dependent cell status before addition of the compound and about time dependent cell status under the interaction of the compound. This information can be used to determine the effect of a compound on the cells.

In yet another aspect, the present invention provides a method for performing real-time cytotoxicity assays of at least one compound, comprising: providing an above described cell-substrate impedance measurement system; introducing cells into one or more wells of the system that comprise an electrode array; adding one or more compounds to the one or more wells containing cells; and monitoring cell-substrate impedance of the one or more wells before and after adding the one or more compounds, wherein the time dependent impedance change provides information about time dependent cytotoxicity of the compound or compounds. Preferably, cell-substrate impedance is monitored at regular or irregular time intervals after adding one or more compounds to the one or more of the wells containing cells. The time dependent impedance change can provide information about any potential cytotoxic effects of the compound.

In one embodiment of the above methods, multiple wells with same cell types are used, wherein different concentrations of a compound are added to different wells that comprise cells. The method can monitor and quantitate time-dependent and concentration-dependent cellular responses.

In yet another aspect, the present invention provides a method for analyzing and comparing time-dependent effects of a first compound and a second compound on a cell type, comprising: a) performing a real-time assay on a cell type with the first compound using the method described above; b) performing a real-time assay on said cell type with the second compound using the method described above; and c) comparing the time-dependent responses of the first compound and the second compound.

In one embodiment of this method, time-dependent cellular responses are determined for a first compound at multiple dose concentrations. In another embodiment, time-dependent responses are determined for a second compound at multiple dose concentrations. In yet another embodiment, time-dependent cellular responses are determined for both a first compound and a second compound at multiple dose concentrations.

In yet another aspect, the present invention provides methods for cytotoxicity profiling for a compound on multiple cell types, comprising: a) performing real-time cytotoxicity assays on different cell types with the compound using the method described above, and b) analyzing real-time cytotoxic responses of different cell types to the compound to provide a cytotoxicity profile of the compound. In yet another embodiment, the above methods are applied to perform cytotoxicity profiling of multiple compounds on multiple cell types.

BRIEF DESCRIPTION OF THE DRAWINGS

FIG. 12B shows the characterization of the cell biological effect of doxorubicin treatment on MV522 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.

DETAILED DESCRIPTION OF THE INVENTION

A. Definitions

Figure 1A:
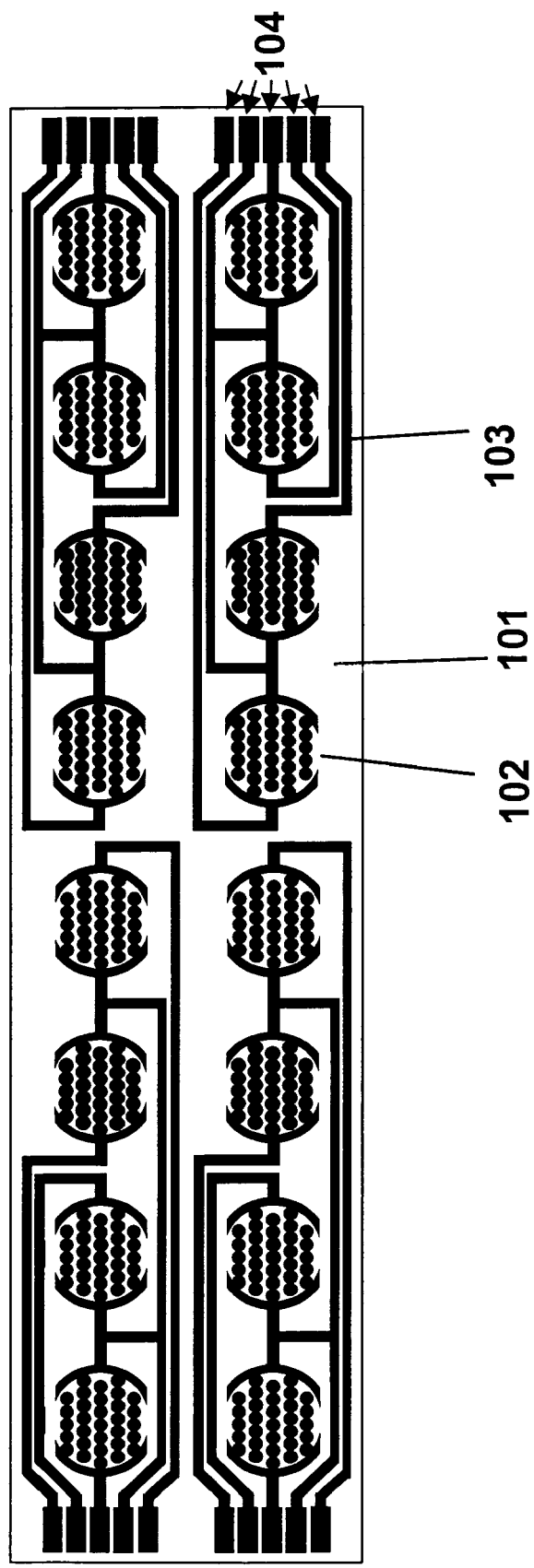
FIG. 1 shows schematic drawings of one design of a cell-substrate impedance measurement device of the present invention. A) depicts the substrate having 16 electrode arrays (or 16 electrode structure units) that are arranged in a 2-row by 8-column configuration on a substrate. B) depicts a single electrode array of a device. C) shows a schematic drawing of an electrode array, illustrating the requirement of approximately uniform distribution of electrode resistance across the array.

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible membrane" means a membrane that does not have deleterious effects on cells, including the viability, attachment, spreading, motility, growth, or cell division.

When a suspension of viable, unimpaired, epithelial or endothelial cells is added to a vessel, a surface of the vessel "is suitable for cell attachment" when a significant percentage of the cells are adhering to the surface of the vessel within twelve hours. Preferably, at least 50% of the cells are adhering to the surface of the vessel within twelve hours. More preferably, a surface that is suitable for cell attachment has surface properties so that at least 70% of the cells are adhering to the surface within twelve hours of plating (i.e., adding cells to the vessel). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a membrane) preferably is suitable for the attachment of cells of the type that are to be used in an assay that uses the biocompatible surface (e.g., membrane), and most preferably, allows the attachment of at least 90% of the cells that contact the biocompatible surface during the assay.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" means that the at least two electrodes are fabricated on the same side of the substrate.

As used herein, "at least two electrodes fabricated to a same plane of said substrate" means that, if the nonconducting substrate has multiple layers, the at least two electrodes are fabricated to the same layer of the substrate.

As used herein, "said . . . electrodes [or electrode structures] have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among said electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the does concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus doss concentration provides information not only about number of cells but also about their physiological status (e.g. cell morphology and cell adhesion). Furthermore, an important advantage offered by the system and devices of the present application is that in a single experiment, one can obtain "dose-response curves" at multiple time points since the system allows for the continuous monitoring of cells and provides impedance measurement at many time points over a time range as short as a few minutes to as long as days or weeks.

As used herein, "the electrodes have, along the length of the microchannel, a length that is substantially less than the largest single-dimension of a particle to be analyzed" means that the electrodes have, along the length of the microchannel, a length that is at least less than 90% of the largest single-dimension of a particle to be analyzed. Preferably, the electrodes have, along the length of the microchannel, a length that is at least less than 80%, 70%, 60%, 50%, 40%, 30%, 20%, 10%, 5% of the largest single-dimension of a particle to be analyzed.

As used herein, "the microelectrodes span the entire height of the microchannel" means that the microelectrodes span at least 70% of the entire height of the microchannel. Preferably, microelectrodes span at least 80%, 90%, 95% of the entire height of the microchannel. More preferably, microelectrodes span at least 100% of the entire height of the microchannel.

As used herein, "an aperture having a pore size that equals to or is slightly larger than size of said particle" means that aperture has a pore size that at least equals to the particle size but less than 300% of the particle size. Here both pore size and particle size are measured in terms of single dimension value.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

A "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc. The structure of a test compound can be known or unknown.

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell viability, cell adhesion, apoptosis, cell differentiation, cell proliferation, cell morphology, cell cycle, IgE-mediated cell activation or stimulation, receptor-ligand binding, cell number, cell quality, cell cycling, etc.

An "impedance value" is the impedance measured for electrodes in a well with or without cell present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

A "Cell Index" or "CI" is a parameter that can derived from measured impedance values and that can be used to reflect the change in impedance values. There are a number of methods to derive or calculate Cell Index.

A "Normalized Cell Index" at a given time point is calculated by dividing the Cell Index at the time point by the Cell Index at a reference time point. Thus, the Normalized Cell Index is 1 at the reference time point.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the 1$^{st}$ order derive of the Cell Index with respect to time, divided by the Cell Index at the time point. In other words, CCI is calculated as $$CCI(t) = \frac{dCI(t)}{CI(t) \cdot dt}.$$

B. Devices and Systems for Monitoring Cell-Substrate Impedance

Devices for Measuring Cell-Substrate Impedance

The present invention includes devices for measuring cell-substrate impedance that comprise a nonconducting substrate; two or more electrode arrays fabricated on the substrate, where each of the two or more electrode arrays comprises two electrode structures; and at least two connection pads, each of which is located on an edge of the substrate. Each electrode array of the device has approximately uniform electrode resistance across the entire array. The substrate of the device has a surface suitable for cell attachment or growth; where cell attachment or growth on said substrate can result in a detectable change in impedance between or among the electrode structures within each electrode array.

An electrode array is two or more electrode structures that are constructed to have dimensions and spacing such that they can, when connected to a signal source, operate as a unit to generate an electrical field in the region of spaces around the electrode structures. An electrode structure refers to a single electrode, particularly one with a complex structure. (For example, an electrode structure can comprise two or more electrode elements that are electrically connected together.) In devices of the present invention, an electrode array comprises two electrode structures, each of which comprises multiple electrode elements, or substructures. In preferred embodiments of the present invention, the electrode structures of each of the two or more electrode arrays of a device have substantially the same surface area. In preferred embodiments of a device of the present invention, each of the two or more electrode arrays of a device comprise two electrode structures, and each electrode structure comprises multiple electrode elements. Each of the two electrode structures of an electrode array is connected to a separate connection pad that is located at the edge of the substrate.

Thus, in devices of the present invention, for each of the two or more electrode arrays of the device, the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time by using switches (such as electronic switches).

Each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

For a device of the present invention, preferred arrangements for the electrode elements, gaps between the electrodes and electrode buses in a given electrode array are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in parent U.S. patent application Ser. No. 10/705,447, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. patent application Ser. No. 10/705,447, herein incorporated by reference for all description and disclosure of the design, features, and manufacture of impedance device comprising electrode arrays.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups.

Descriptions of electrode arrays used for impedance measurement that apply to the devices of the present invention are described in parent U.S. patent application Ser. No. 10/705,447, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure.

Preferably, the electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an array of the present device of the present invention are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

A device of the present invention can include one or more fluid-impermeable receptacles which serve as fluid containers. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in parent U.S. patent application Ser. No. 10/705,447, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in parent U.S. patent application Ser. No. 10/705,447, and also in parent application U.S. patent application Ser. No. 10/987,732, both herein incorporated by reference for disclosure of multiwell impedance measurement devices, including their design, composition, and manufacture. A device of the present invention preferably has between 2 and 1,536 wells, more preferably between 4 and 384 wells, and even more preferably, between 16 and 96 wells, all or less than all or which are associated with electrode arrays.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

Methods of Use

The present invention also includes methods of using a device of the present invention that comprises fluid containers situated over electrode arrays to measure cell-substrate impedance. Such methods include: providing a device of the present invention that comprises fluid containers situated over electrode arrays, attaching an impedance analyzer to a device of the present invention, adding cells to one or more fluid containers of the device, and measuring impedance over one or more arrays of the device. Methods of performing cell assays using impedance measurement devices can be found in parent U.S. patent application Ser. No. 10/987,732 and U.S. patent application Ser. No. 10/705,447, both herein incorporated by reference for all disclosure of methods of using impedance measurement devices, as well as in Sections D and E of the present application.

Cell-Substrate Impedance Measurement Systems

In another aspect, the present invention is directed to a cell-substrate impedance measurement system comprising a) at least one multiple-well cell-substrate impedance measuring device, in which at least two of the multiple wells comprise an electrode array at the bottom of the well; b) an impedance analyzer electronically connected to the multiple-well cell-substrate impedance measuring device; c) a device station capable of engaging the one or more multiple-well devices and comprising electronic circuitry capable of selecting and connecting electrode arrays within any of the multiple wells to the impedance analyzer; and d) a software program connected to the device station and impedance analyzer to control the device station and perform data acquisition and data analysis from the impedance analyzer.

In a cell-substrate impedance measurement system of the present invention, the impedance analyzer engages connection pads of one or more multi-well devices to measure impedance. In one embodiment of the above system, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 0.1 ohm and 103 ohm in frequency range of 100 Hz to 100 kHz.

A cell-substrate measurement system can be used to efficiently and simultaneously perform multiple assays by using circuitry of the device station to digitally switch from recording from measuring impedance over an array in one well to measuring impedance over an array in another well. In one embodiment of the above system, the system under software control is capable of completing an impedance measurement for an individual well at a single frequency within less than ten seconds. In another embodiment, the averaged time used by the system to complete an impedance measurement for an individual well at a single frequency is less than one second.

A multiple-well cell-substrate impedance measuring device in a system of the present invention can be any multiple-well cell-substrate impedance measuring device in which at least two of the multiple wells comprise an electrode array at the bottom of the well, and in which at least two of the multiple wells comprise an electrode array are individually addressed. In one embodiment of the above system, the multi-well device takes the form of a specialized microtiter plate which has microelectronic sensor arrays integrated into the bottom of the wells.

A device used in a system of the present invention, when connected to an impedance analyzer, can measure differences in impedance values that relate to cell behavior. For example, a cell-substrate impedance measuring device used in a system of the present invention can measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes.

Preferred devices that can be part of a cell-substrate impedance monitoring system can be those described in parent U.S. patent application Ser. No. 10/705,447, and in U.S. patent application Ser. No. 10/987,732, both herein incorporated by reference for disclosure of cell-substrate impedance monitoring devices that comprise electrode arrays, including disclosure of their design, composition, and manufacture. Preferred devices that can be part of a cell-substrate impedance monitoring system can also be those described in the present application.

Preferably a multi-well device of a system of the present invention comprises between 4 and 1,536 wells, some or all of which can comprise electrode arrays. In some embodiments of the present invention, a device station can comprise one or more platforms or one or more slots for positioning one or more multiwell devices. The one or more platforms or one or more slots can comprise sockets, pins or other devices for electrically connecting the device to the device station. The device station preferably can be positioned in a tissue culture incubator during cell impedance measurement assays. It can be electrically connected to an impedance analyzer and computer that are preferably located outside the tissue culture incubator.

The device station comprises electronic circuitry that can connect to an impedance monitoring device and an impedance analyzer and electronic switches that can switch on and off connections to each of the two or more electrode arrays of the multiwell devices used in the system. The switches of the device station are controlled by a software program. The software program directs the device station to connect arrays of the device to an impedance analyzer and monitor impedance from one or more of the electrode arrays. During impedance monitoring, the impedance analyzer can monitor impedance at one frequency or at more than one frequency. Preferably, impedance monitoring is performed at more than one time point for a given assay, and preferably, impedance is monitored at at least three time points. The device station can connect individual arrays of a device to an impedance analyzer to monitor one, some, or all of the arrays of a device for a measurement time point. The switches of the device station allow the selected individual arrays to be monitored in rapid succession for each desired monitoring time point. Each monitoring time point is in fact a narrow time frame (for example from less than one second to minutes) of measurement in the assay during which impedance monitoring is performed. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc.

Preferably, the software can also analyze impedance data. In preferred embodiments, the software can calculate a cell index (CI) for one or more time points for one or more wells of the multiwell device. In some preferred embodiments, the software can calculate a cell change index (CCI) from impedance measurements of one or more wells of the multiwell device. The software can preferably generate plots of impedance data and impedance values, such as but not limited to CI or CCI, with respect to time. The software may perform other analysis as well, such as calculate cell number from CI, generate dose-response curves based on impedance data, calculate IC values based on impedance values, and calculate kinetic parameters of cell growth or behavior based on impedance values and impedance value curves. The software of the impedance monitoring system can also store and display analyses of the data, such as calculated impedance values and kinetic parameters derived therefrom, Data can be displayed on a screen, as printed data, or both.

C. Methods for Calculating Cell Index (CI) and Cell Change Index (CCI)

Cell Index

Based on the dependent relationship between the measured impedance, cell number (more accurately, the viable cell number, or attached cell number) and cell attachment status, it is possible to derive a so-called "cell number index" or "cell index" from the measured impedance frequency spectra that provides a useful index for quantitating and comparing cell behavior in the impedance-based assays of the present invention. In some applications of the present invention, "cell index" in the present application is the same as "cell number index" in PCT Application No. PCT/US03/22557, entitled "IMPEDANCE BASED DEVICES AND METHODS FOR USE IN ASSAYS", filed on Jul. 18, 2003 and in U.S. patent application Ser. No. 10/705,447, entitled "IMPEDANCE BASED DEVICES AND METHODS FOR USE IN ASSAYS," filed on Nov. 10, 2003, U.S. patent application Ser. No. 10/987,732, filed Nov. 12, 2004, U.S. patent application Ser. No. 10/705,447 and PCT Application No. PCT/US03/22557 are hereby incorporated by reference for the discussions and disclosures of cell index and cell number index they contain.

Various methods for calculating such a cell number index can be used, some of which are novel methods disclosed herein.

The present invention provides several methods of calculating cell index numbers for cells attached to two or more essentially identical arrays of a cell-substrate impedance device, where the cells are monitored for impedance changes. In preferred embodiments of the present invention, the methods calculate cell index number with better accuracy than previous methods of calculating cell index for cells on two or more arrays of a cell-substrate monitoring device. In some preferred methods of the present invention, methods of calculating a cell index rely on novel methods for calculating the resistances of electrical traces leading to two or more essentially identical arrays. The present invention therefore also includes methods of calculating resistances of electrical traces leading to two or more essentially identical arrays on a substrate.

By "essentially identical electrode arrays" or "essentially identical arrays" is meant that the dimensions and arrangement of electrodes, electrode structures, and electrode elements is the same for the referenced arrays. Thus, two essentially identical electrode arrays will have electrode structures of the same dimensions (length, width, thickness), where the electrode structures have the same number of electrode elements, and the arrangement of electrode structures and electrode elements in each array are the same. By arrangement is meant the distance between structures or elements (gap width), their physical position with respect to one another, and their geometry (angles, degree of curvature, circle-online or castellated geometries, etc.), including the same features of any electrode buses that may be connected to electrode structures or electrode elements. Electrodes of essentially identical arrays also comprise the same materials. For the purposes of calculating trace resistances and cell index number, a substrate can have any number of essentially identical arrays.

The following discussion provides novel methods of calculating cell index of cells adhered to arrays of a cell-substrate impedance monitoring device and novel methods for the calculation of the resistances of the electrical connection traces leading to two or more electrode arrays of a cell-substrate impedance monitoring device.

Impedance (Z) has two components, namely the resistance Rs and reactance Xs. Mathematically, the impedance Z is expressed as follows, $$Z = Rs + j Xs, \qquad (2)$$

where $j = \sqrt{-1}$, depicting that for the (serial) reactance component Xs, the voltage applied over it is 90 degree phased-out from the current going through it. For the (serial) resistance, the voltage applied over it is in phase with the current going through it. As it is well-known in electronic and electrical engineering, the impedance can also be expressed in terms of parallel resistance Rp and parallel reactance Xp, as follows, $$Z = Rp*(j Xp)/(Rp + j Xp), \qquad (3)$$

where $j = \sqrt{-1}$. Nevertheless, these expressions (serial resistance and serial reactance, or parallel resistance and parallel reactance) are equivalent. Those who are skilled in electrical and electronic engineering can readily derive one form of expression from the parameter values in the other expression. For the sake of clarity and consistency, the description and discussion in the present invention utilizes the expression of serial resistance and serial reactance. For simplicity, serial resistance and serial reactance are simply called resistance and reactance.

As described in U.S. patent application Ser. No. 10/705, 447, entitled "Impedance based devices and methods for use in assays", filed on Nov. 10, 2003 and PCT application number PCT/US03/22557, entitled "Impedance based devices and methods for use in assays", filed on Jul. 18, 2003, both of which are herein incorporated by reference for disclosures relating to cell-substrate impedance monitoring, monitoring cell-substrate impedance for detection or measurement of change in impedance can be done by measuring impedance in any suitable range of frequencies. For example, the impedance can be measured in a frequency range from about 1 Hz to about 100 MHz. In another example, the impedance can be measured in a frequency range from about 100 Hz to about 2 MHz. The impedance is typically a function of the frequency, i.e., the impedance values change as frequency changes. Monitoring cell-substrate impedance can be done either in a single frequency or multiple frequencies. If the impedance measurement is performed at multiple frequencies, then a frequency-dependent impedance spectrum is obtained—i.e., there is an impedance value at each measured frequency. As mentioned above, the impedance has two components—a resistance component and a reactance component. A change in either resistance component or reactance component or both components can constitute a change in impedance.

As described in the U.S. patent application Ser. No. 10/705, 447, entitled "Impedance based devices and methods for use in assays", filed on Nov. 10, 2003 and PCT application number PCT/US03/22557, entitled "Impedance based devices and methods for use in assays", filed on Jul. 18, 2003, herein incorporated by reference for disclosure of methods of measuring electrical impedance, the method for the measurement of electrical (or electronic) impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. As it is well-known in electrical and electronic engineering, in such calculations (e.g. divisions mentioned above), the current amplitude and voltage amplitude are expressed in the form of complex numbers, which take into account of how big the current and the voltage are and what the phase difference between the sinusoidal waves of the current and the voltage is. Similarly, the impedance value is also expressed in a complex form, having both resistance and reactance component, as shown in equations above.

As described in the U.S. patent application Ser. No. 10/705, 447, entitled "Impedance based devices and methods for use in assays", filed on Nov. 10, 2003 and PCT application number PCT/US03/22557, entitled "Impedance based devices and methods for use in assays", filed on Jul. 18, 2003, both incorporated herein by reference for disclosure relating to Cell Index or Cell Number Index, the measured cell-substrate impedance can be used to calculate a parameter termed Cell Index or Cell Number Index. Various methods for calculating such a cell number index can be used based on the changes in resistance or reactance when cells are attached to the electrode structures with respect to the cases no cells are attached to the electrode structures. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example (A), the cell index or cell number index can be calculated by:

(A1) at each measured frequency, calculating the resistance ratio by dividing the resistance of the electrode arrays when cells are present and/or attached to the electrodes by the baseline resistance, (A2) finding or determining the maximum value in the resistance ratio over the frequency spectrum, (A3) and subtracting one from the maximum value in the resistance ratio.

Using a mathematically formula, Cell Index is derived as $$\text{Cell Index} = \max_{i=1,2,\ldots N}\left(\frac{R_{cell}(f_i)}{R_b(f_i)} - 1\right) \quad (4)$$

Where N is the number of the frequency points at which the impedance is measured. For example, if the frequencies used for the measurements are at 10 kHz, 25 kHz and 50 kHz, then N=3, $f_1$=10 kHz, $f_2$=25 kHz, $f_3$=50 kHz. $R_{cell}(f_i)$ is the resistance (cell-substrate resistance) of the electrode arrays or electrode structures when the cells are present on the electrodes at the frequency $f_i$ and $R_b(f_i)$ is the baseline resistance of the electrode array or structures at the frequency $f_i$.

The cell index obtained for a given well reflects: 1) how many cells are attached to the electrode surfaces in this well, 2) how well cells are attached to the electrode surfaces in the well._ In this case, a zero or near-zero "cell index or cell number index" indicates that no cells or very small number of cells are present on or attached to the electrode surfaces. In other words, if no cells are present on the electrodes, or if the cells are not well-attached onto the electrodes, $R_{cell}(f_i)$ is about the same as $R_b(f_i)$, leading to Cell Index=0. A higher value of "cell number index" indicates that, for same type of the cells and cells under similar physiological conditions, more cells are attached to the electrode surfaces. In other words, under same physiological conditions, more cells attached on the electrodes, the larger the values $R_{cell}(f_i)$ is, leading to a large value for Cell Index. Thus Cell Index is a quantitative measure of cell number present in a well. A higher value of "cell index" may also indicate that, for same type of the cells and same number of the cells, cells are attached better (for example, cells spread out more, or cell adhesion to the electrode surfaces is stronger) on the electrode surfaces. Thus, for same number of the cells present in the well, change in a cell status will lead to a change in cell index. For example, an increase in cell adhesion or a cell spread leading to large cell/electrode contact area will result in an increase in $R_{cell}(f)$ and a larger Cell Index. On the other hand, a cell death or toxicity induced cell detachment, cell rounding up, will lead to smaller $R_{cell}(f)$ and thus smaller Cell Index.

In another example (B), the cell number index can be calculated by:

(B1) at each measured frequency, calculating the reactance ratio by dividing the reactance of the electrode arrays when cells are present on and/or attached to the electrodes by the baseline reactance, (B2) finding or determining the maximum value in the reactance ratio over the frequency spectrum, (B3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example (C), the cell index can be calculated by:

(C1) at each measured frequency, subtracting the baseline resistance from the resistance of the electrode arrays when cells are present or attached to the electrodes to determine the change in the resistance with the cells present relative to the baseline resistance;

(C2) then finding or determining the maximum value in the change of the resistance.

In this case, "cell-number index" is derived based on the maximum change in the resistance across the measured frequency range with the cells present relative to the baseline resistance. This cell index would have a dimension of ohm.

In yet another example (D), the cell index can be calculated by:

(D1) at each measured frequency, calculating the magnitude of the impedance (equaling to $\sqrt{R_s^2 + X_s^2}$, where $R_s$ and $X_s$ are the serial resistance and reactance, respectively).

(D2) subtracting the magnitude of the baseline impedance from the magnitude of the impedance of the electrode arrays when cells are present or attached to the electrodes to determine the change in the magnitude of the impedance with the cells present relative to the baseline impedance;

(D3) then finding or determining the maximum value in the change of the magnitude of the impedance.

In this case, "cell-number index" is derived based on the maximum change in the magnitude of the impedance across the measured frequency range with the cells present relative to the baseline impedance. This cell index would have a dimension of ohm.

In yet another example (E), the index can be calculated by:

(E1) at each measured frequency, calculating the resistance ratio by dividing the resistance of electrode arrays when cells are present or attached to the electrodes by the baseline resistance, (E2) then calculating the relative change in resistance in each measured frequency by subtracting one from the resistance ratio, (E3) then integrating all the relative-change value (i.e., summing together all the relative-change values at different frequencies).

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

In yet another example (F), the cell index can be calculated by:

(F1) at each measured frequency, subtracting the baseline resistance from the resistance of the electrode arrays when cells are attached to the electrodes to determine the change in the resistance with the cells present relative to the baseline impedance; (here the change in the resistance is given by $\Delta R(f_i) = R_{s\text{-}cell}(f_i) - R_{s\text{-}baseline}(f_i)$ for the frequency $f_i$, $R_{s\text{-}cell}$ and $R_{s\text{-}baseline}$ are the serial resistances with the cells present on the electrode array and the baseline serial resistances, respectively);

(F3) analyzing the frequency dependency of the change of the resistance to derive certain parameters that can quantify such dependency. In one example, such parameters can be calculated as $$\sqrt{\sum_i [\Delta R(f_i)]^2}.$$

In another example, such parameter can be calculated as $$\sum_i |\Delta R(f_i)|.$$

The parameter(s) are used as cell index or cell number index.

In this case, "cell-number index" is derived based on the analysis of the frequency spectrum of the change in the resistance. Depending how the parameters are calculated, the cell index may have a dimension of ohm.

In yet another example (G), the cell index can be calculated by:
- (G1) at each measured frequency, calculating the magnitude of the impedance (equaling to $\sqrt{R_s^2 + X_s^2}$, where $R_s$ and $X_s$ are the serial resistance and reactance, respectively).
- (G2) subtracting the magnitude of the baseline impedance from the magnitude of the impedance of the electrode arrays when cells are attached to the electrodes to determine the change in the magnitude of the impedance with the cells present relative to the baseline impedance; (here, the change in the magnitude of the impedance is given by $\Delta Z(f_i) = |Z_{cell}(f_i)| - |Z_{baseline}(f_i)|$ for the frequency $f_i$, $|Z_{cell}(f_i)| = \sqrt{R_{s\text{-}cell}(f_i)^2 + X_{s\text{-}cell}(f_i)^2}$, $R_{s\text{-}cell}$ and $X_{s\text{-}cell}$ being the serial resistance and reactance with the cells present on the electrode arrays, respectively, $|Z_{cell}(f_i)|$ is the magnitude of the impedance of the electrode array with cells present on the electrode arrays, $|Z_{baseline}(f_i)|$ is the magnitude of the baseline impedance of the electrode array);
- (G3) analyzing the frequency dependency of the change of the magnitude of the impedance to derive certain parameters that can quantify such dependency. In one example, such parameters can be calculated as $$\sqrt{\sum_i [\Delta Z(f_i)]^2}.$$

In another example, such parameter can be calculated as $$\sum_i |\Delta Z(f_i)|.$$

The parameter(s) are used as cell index or cell number index.

In this case, "cell-number index" is derived based on the analysis of the frequency spectrum of the change in the magnitude of the impedance. Depending how the parameters are calculated, the cell index may have a dimension of ohm.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, and U.S. patent application Ser. No. 10/987,732, all herein incorporated by reference for disclosure of Cell Index or Cell Number Index and its calculation, there are different methods for calculating the parameter termed Cell Index or Cell Number Index from the measured cell-substrate impedance (resistance or reactance). Cell Index or Cell Number Index is a quantitative measure of cells in the wells under cell-substrate impedance measurement.

It is worthwhile to point out that it is not necessary to derive such a "cell number index" for utilizing the impedance information for monitoring cell conditions over the electrodes. Actually, one may choose to directly use measured impedance (e.g., at a single fixed frequency; or at a maximum relative-change frequency, or at multiple frequencies) as an indicator of cell conditions. If measured impedance values are directly used for monitoring cell conditions, then resistance, or reactance or both resistance and reactance can be used.

Still, deriving "cell index" or "cell number index" and using such index to monitor cell conditions may have advantages. There are several advantages of using "cell number index" to monitor cell growth and/or attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

As shown above, for some methods of calculating cell index or cell number index, it is important to know the impedance (resistance and/or reactance) of the electrode structures with and without cells present on them. Based on the equation (1), the impedance of the electrode array (with or without cells present on the electrodes) is given by $$Z_{electrode\text{-}array} = Z_{total} - Z_{trace} - Z_{switch} \quad (5)$$

Where $Z_{switch}$ is the impedance of electronic switch at its on stage, $Z_{trace}$ is the impedance of the electrical connection traces (or electrical conductive traces) on the substrate between the connection pads and the electrode buses, $Z_{total}$ is the total impedance measured at the impedance analyzer. By choosing electronic switches with good quality, it is possible to have all the electronic switches have a consistent on-impedance (mainly resistance). For example, the on-resistance of electronic switches can be about 3 ohm (±10%) with the on reactance being negligible (for example, less than 0.2 ohm in the frequency range of interest). Thus, if the trace impedance is determined or calculated, then formula (5) can be used to calculate the impedance of the electrode arrays with or without cells present.

Figure 1B:
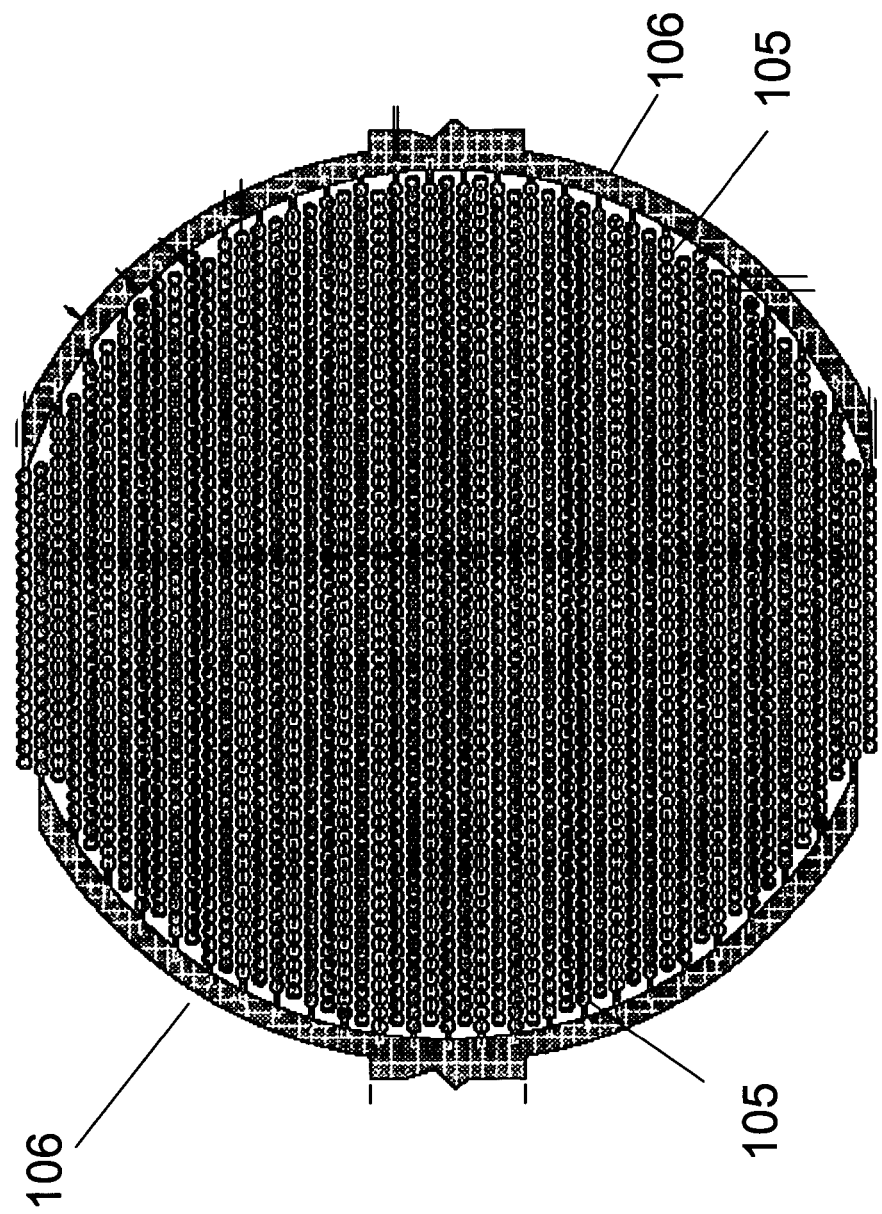
Figure 1C:
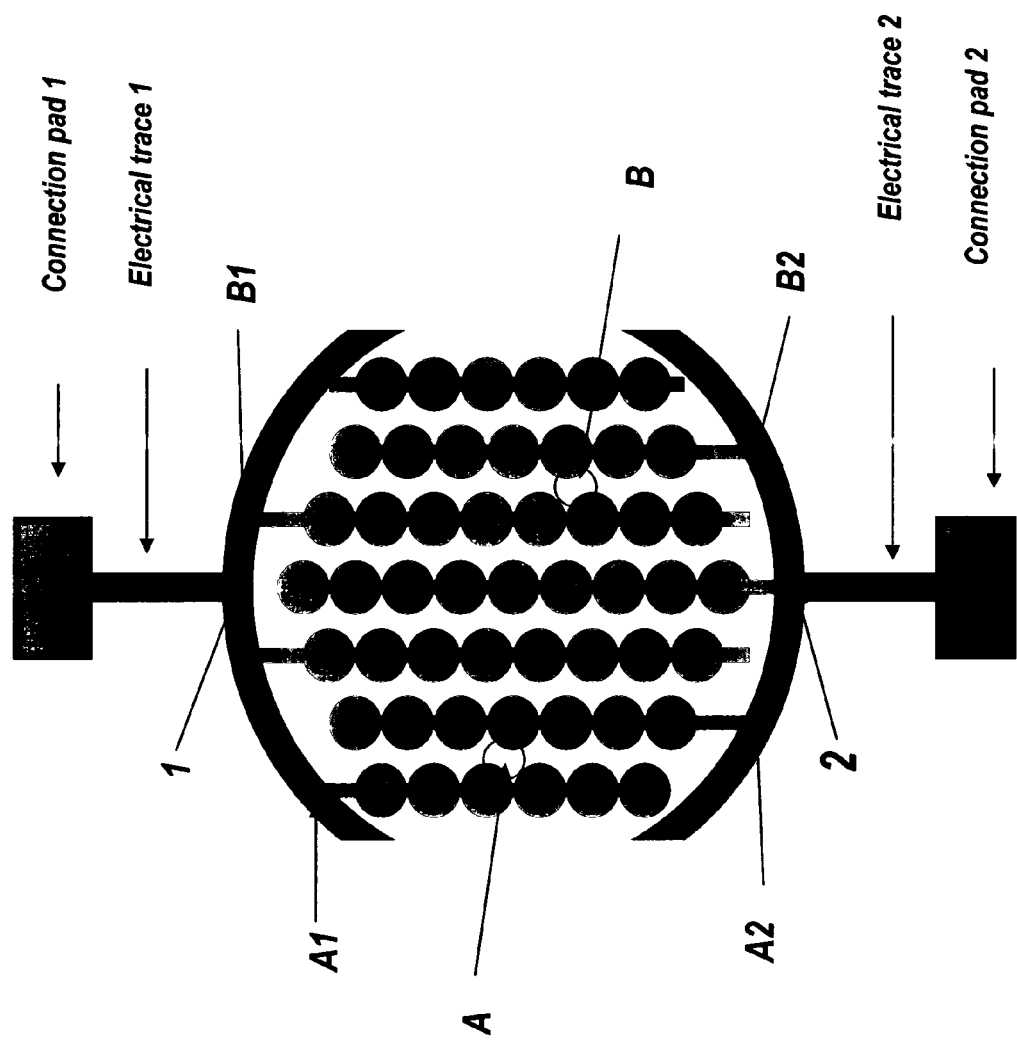

A method is invented in the present application to determine the impedance of electrical conductive (electrical connection) traces (mainly trace resistance, trace reactance is very small for the thin conductive film trace) based on the relationships among two or more essentially identical arrays on a cell-substrate impedance monitoring device. In the following, the four electrode arrays A, B, C and D as indicated in FIG. 1, are used to illustrate this method. The electrical reactance (serial reactance) of the electronic switches and the electrical reactance (serial reactance) of the electrical connection traces are small as compared with the corresponding electrical resistances (serial resistances). Thus, we focus on the analysis of the resistance of the electrical connection traces. The impedance determined from the impedance analyzer does contain both resistance (serial resistance, $R_{total}$) and reactance (serial reactance). For the electrode arrays A-D, the measured total resistance $R_{total}$, the resistance ($R_{trace}$) of electrical conductive (connection) trace, the switch resistance ($R_{switch}$) and the resistance ($R_{e-array}$) of the electrode array satisfy the following equations:

$$R_{e\text{-}array\text{-}A} = R_{total\text{-}A} - R_{trace\text{-}A} - R_{switch\text{-}A} \tag{6A}$$

$$R_{e\text{-}array\text{-}B} = R_{total\text{-}B} - R_{trace\text{-}B} - R_{switch\text{-}B} \tag{6B}$$

$$R_{e\text{-}array\text{-}C} = R_{total\text{-}C} - R_{trace\text{-}C} - R_{switch\text{-}C} \tag{6C}$$

$$R_{e\text{-}array\text{-}D} = R_{total\text{-}D} - R_{trace\text{-}D} - R_{switch\text{-}D} \tag{6D}$$

With chosen electronic switches having consistent switch-on resistance, $R_{switch\text{-}A}$, $R_{switch\text{-}B}$, $R_{switch\text{-}C}$ and $R_{switch\text{-}D}$ have very similar values and can be assumed to be the same, $R_{switch}$. Thus, in above equations, the known parameters are $R_{total\text{-}A}$, $R_{total\text{-}B}$, $R_{total\text{-}C}$ and $R_{total\text{-}D}$, and $R_{switch\text{-}A}$, $R_{switch\text{-}B}$, $R_{switch\text{-}C}$ and $R_{switch\text{-}D}$, and there are eight unknown parameters $R_{e\text{-}array\text{-}A}$, $R_{e\text{-}array\text{-}B}$, $R_{e\text{-}array\text{-}C}$ and $R_{e\text{-}array\text{-}D}$, and $R_{trace\text{-}A}$, $R_{trace\text{-}B}$, $R_{trace\text{-}C}$ and $R_{trace\text{-}D}$. It is impossible to solve these equations for the eight unknown variables from these four equations directly. Additional relationships between these variables are needed to solve for them. Each trace resistance ($R_{trace\text{-}A}$, $R_{trace\text{-}B}$, $R_{trace\text{-}C}$ and $R_{trace\text{-}D}$) depends on the metal film type used, and the geometry of the trace such as the how many rectangular segments the trace has, the film thickness(es) of the segments, the width(s) of the segments, the length(s) of the segment(s). For example, $$R_{trace-A} = \sum_{i=1}^{N} \rho \frac{L_{A-i}}{t_{A-i} * d_{A-i}} \tag{7}$$

where N is the number of the segments of the trace-A, $t_{A-i}$, $d_{A-i}$ and $L_{A-i}$ is the thickness, width and length of the i-th segment of the traces for the electrode array A, and $\rho$ is the resistivity of the thin film. The equation here applies to the film comprising a single type of metal. The equation can be readily modified to be applicable to the film comprising two or more metal types (e.g. gold film over chromium adhesion layer).

If the film thickness is reasonably uniform (for example, less than 10% in thickness variation) across the substrate, then the relationship among the trace resistances is simply determined by the pre-determined geometrical shapes (e.g. the length, width of the segments). For example, it would be straightforward to calculate the ratio $\alpha_{A\text{-}D}$ between the resistance of the electrically conductive traces for the electrode array A to the resistance of the electrically conductive traces for the electrode array D as below, where the film thickness is assumed to be the same everywhere on these traces and the resistivity is also the same everywhere on these traces, $$\alpha_{A-D} = \frac{R_{trace\_A}}{R_{trace\_D}} = \frac{\sum_{i=1}^{N} \rho \frac{L_{A-i}}{t_{A-i} * d_{A-i}}}{\sum_{i=1}^{M} \rho \frac{L_{D-i}}{t_{D-i} * d_{D-i}}} = \frac{\sum_{i=1}^{N} \frac{L_{A-i}}{d_{A-i}}}{\sum_{i=1}^{M} \frac{L_{D-i}}{d_{D-i}}}. \tag{8}$$

Similarly, one can determine the ratio $\alpha_{B\text{-}D}$ and $\alpha_{C\text{-}D}$ based on the pre-determined geometrical relationships for the traces of the electrode arrays B, C and D. Note that above equations can be similarly derived for the cases where the thin film in these traces comprises more than one metal type. Thus, based on the equalities $$R_{switch\text{-}A} = R_{switch\text{-}B} = R_{switch\text{-}C} = R_{switch\text{-}D} = R_{switch}, \tag{9A}$$

$$R_{trace\text{-}A} = \alpha_{A\text{-}D} \cdot R_{trace\text{-}D}, \tag{9B}$$

$$R_{trace\text{-}B} = \alpha_{B\text{-}D} \cdot R_{trace\text{-}D}, \tag{9C}$$

and $R_{trace\text{-}C} = \alpha_{C\text{-}D} \cdot R_{trace\text{-}D}$ \hfill (9D)

equations (6A)-(6D) can be re-written in the following format:

$$R_{e\text{-}array\text{-}A} = R_{total\text{-}A} - \alpha_{A\text{-}D} \cdot R_{trace\text{-}D} - R_{switch} \tag{10A}$$

$$R_{e\text{-}array\text{-}B} = R_{total\text{-}B} - \alpha_{B\text{-}D} \cdot R_{trace\text{-}D} - R_{switch} \tag{10B}$$

$$R_{e\text{-}array\text{-}C} = R_{total\text{-}C} - \alpha_{C\text{-}D} \cdot R_{trace\text{-}D} - R_{switch} \tag{10C}$$

$$R_{e\text{-}array\text{-}D} = R_{total\text{-}D} - R_{trace\text{-}D} - R_{switch\text{-}D} \tag{10D}$$

For equations (10A) through (10D), there are five unknown variables, $R_{e\text{-}array\text{-}A}$, $R_{e\text{-}array\text{-}B}$, $R_{e\text{-}array\text{-}C}$, and $R_{e\text{-}array\text{-}D}$ and $R_{trace\text{-}D}$. Mathematically, these unknown variables cannot be determined from these equations. Additional information is needed to solve for these variables $R_{e\text{-}array\text{-}A}$, $R_{e\text{-}array\text{-}B}$, $R_{e\text{-}array\text{-}C}$, and $R_{e\text{-}array\text{-}D}$ and $R_{trace\text{-}D}$.

One approach is invented and described in the present invention. In this approach, same biological or chemical solutions or suspensions are applied to the electrode-arrays A through D. Because the electrode arrays A through D have essentially identical electrode structures, the electrode array resistances $R_{e\text{-}array\text{-}A}$, $R_{e\text{-}array\text{-}B}$, $R_{e\text{-}array\text{-}C}$ and $R_{e\text{-}array\text{-}D}$ should be of same, or very similar value for such a condition when all the electrode arrays are exposed to the same biological or chemical solutions or suspensions, i.e.: $R_{e\text{-}array\text{-}A} \approx R_{e\text{-}array\text{-}B} \approx R_{e\text{-}array\text{-}C} \approx R_{e\text{-}array\text{-}D}$. If we assume the averaged electrode array resistance is $R_{e\text{-}array}$, then these approximate relationship exists $R_{e\text{-}array\text{-}A} \approx R_{e\text{-}array\text{-}B} \approx R_{e\text{-}array\text{-}C} \approx R_{e\text{-}array\text{-}D} \approx R_{e\text{-}array}$. Thus, equations (10A-10D) can be changed to the following:

$$R_{e\text{-}array} \approx R_{total\text{-}A} - \alpha_{A\text{-}D} \cdot R_{trace\text{-}D} - R_{switch} \tag{11A}$$

$$R_{e\text{-}array} \approx R_{total\text{-}B} - \alpha_{B\text{-}D} \cdot R_{trace\text{-}D} - R_{switch} \tag{11B}$$

$$R_{e\text{-}array} \approx R_{total\text{-}C} - \alpha_{C\text{-}D} \cdot R_{trace\text{-}D} - R_{switch} \tag{11C}$$

$$R_{e\text{-}array} \approx R_{total\text{-}D} - R_{trace\text{-}D} - R_{switch\text{-}D} \tag{11D}$$

Thus, we would need to find $R_{trace\text{-}D}$ and $R_{e\text{-}array}$ that satisfy the above approximate equality as close as possible. One mathematical approach is to find $R_{trace\text{-}D}$ and $R_{e\text{-}array}$ that would result in the minimum value for the following expression—an expression that quantifies the differences between the two sides of the approximate equality in (11A, 11B, 11C and 11D), $$F(R_{trace-D}, R_{e-array}) = [R_{e-array} - (R_{total-A} - \alpha_{A-D}R_{trace-D} - R_{switch})]^2 +$$

$$[R_{e-array} - (R_{total-B} - \alpha_{B-D}R_{trace-D} - R_{switch})]^2 +$$

$$[R_{e-array} - (R_{total-C} - \alpha_{C-D}R_{trace-D} - R_{switch})]^2 +$$

$$[R_{e-array} - (R_{total-D} - R_{trace-D} - R_{switch})]^2 \quad (12)$$

The expression $F(R_{trace-D}, R_{e-array})$ is the sum of the squared-differences between the two-sides of the approximate equality in (11A, 11B, 11C and 11D). The smaller $F(R_{trace-D}, R_{e-array})$, the closer the two sides of the approximate equality (11A, 11B, 11C and 11D). Thus, values of $R_{trace-D}$ and $R_{e-array}$ that result in the minimum value of $F(R_{trace-D}, R_{e-array})$ should be determined. Mathematical approach involves in the calculation of the first order derivative of $F(R_{trace-D}, R_{e-array})$ to $R_{trace-D}$ and to $R_{e-array}$, and let such first order derivatives equal to zero. The values of $R_{trace-D}$ and $R_{e-array}$ that result in zero for these first-order-derivatives are those that result in the minimum value of $F(R_{trace-D}, R_{e-array})$. The first order derivatives are as follows:

$$\frac{\partial [F(R_{trace-D}, R_{e-aaray})]}{\partial R_{trace-D}} = \quad (13A)$$

$$2 \cdot \alpha_{A-D} \cdot [R_{e-array} - (R_{total-A} - \alpha_{A-D}R_{trace-D} - R_{switch})] +$$
$$2 \cdot \alpha_{B-D} \cdot [R_{e-array} - (R_{total-B} - \alpha_{B-D}R_{trace-D} - R_{switch})] +$$
$$2 \cdot \alpha_{C-D} \cdot [R_{e-array} - (R_{total-C} - \alpha_{C-D}R_{trace-D} - R_{switch})] +$$
$$2 \cdot [R_{e-array} - (R_{total-D} - R_{trace-D} - R_{switch})] = 0;$$

$$\frac{\partial [F(R_{trace-D}, R_{e-aaray})]}{\partial R_{e-array}} = \quad (13B)$$

$$2 \cdot [R_{e-array} - (R_{total-A} - \alpha_{A-D}R_{trace-D} - R_{switch})] +$$
$$2 \cdot [R_{e-array} - (R_{total-B} - \alpha_{B-D}R_{trace-D} - R_{switch})] +$$
$$2 \cdot [R_{e-array} - (R_{total-C} - \alpha_{C-D}R_{trace-D} - R_{switch})] +$$
$$2 \cdot [R_{e-array} - (R_{total-D} - R_{trace-D} - R_{switch})] = 0.$$

Equations (13A) and (13B) can be re-written as $$R_{e-array} \cdot [\alpha_{A-D} + \alpha_{B-D} + \alpha_{C-D} + 1] + R_{trace-D} \cdot [\alpha_{A-D}^2 + \alpha_{B-D}^2 + \alpha_{C-D}^2 + 1] =$$

$$\alpha_{A-D} \cdot [R_{total-A} - R_{switch}] + \alpha_{B-D} \cdot [R_{total-B} - R_{switch}] +$$

$$\alpha_{C-D} \cdot [R_{total-C} - R_{switch}] + [R_{total-D} - R_{switch}] \quad (14A)$$

$$4 \cdot R_{e-array} + R_{trace-D} \cdot [\alpha_{A-D} + \alpha_{B-D} + \alpha_{C-D} + 1] =$$

$$[R_{total-A} - R_{switch}] + [R_{total-B} - R_{switch}] + [R_{total-C} - R_{switch}] + [R_{total-D} - R_{switch}] \quad (14B)$$

Thus, we can solve for $R_{trace-D}$ as follows:

$$R_{trace-D} = \frac{4 \cdot S_1 - A_{11} \cdot S_2}{4 \cdot A_{12} - A_{11} \cdot B_{12}} \quad (15)$$

where $A_{11} = [\alpha_{A-D} + \alpha_{B-D} + \alpha_{C-D} + 1]$;

$A_{12} = [\alpha_{A-D}^2 + \alpha_{B-D}^2 + \alpha_{C-D}^2 + 1]$;

$S_1 = \alpha_{A-D} \cdot [R_{total-A} - R_{switch}] + \alpha_{B-D} \cdot [R_{total-B} - R_{switch}] +$ $\alpha_{C-D} \cdot [R_{total-C} - R_{switch}] + [R_{total-D} - R_{switch}]$;

-continued $B_{12} = [\alpha_{A-D} + \alpha_{B-D} + \alpha_{C-D} + 1]$;

$S_2 = [R_{total-A} - R_{switch}] + [R_{total-B} - R_{switch}] +$ $[R_{total-C} - R_{switch}] + [R_{total-D} - R_{switch}]$.

Thus, with the determined $R_{trace-D}$, the trace resistances of $R_{trace-A}$, $R_{trace-B}$, and $R_{trace-C}$ can be calculated using equations (9B), (9C) and (9D). Furthermore, the electrode array resistance $R_{e-array-A}$, $R_{e-array-B}$, $R_{e-array-C}$ and $R_{e-array-D}$ can be calculated from the measured resistance $R_{total-A}$, $R_{total-B}$, $R_{total-C}$ and $R_{total-D}$ respectively using equations (10A), (10B), (10C) and (10D).

Thus, one aspect of the present invention is directed to a method of calculation of the resistances of the electrical connection traces s from the measured, total resistances for two or more essentially identical electrode arrays (such as, for example arrays A-D in FIG. 1), comprising the following steps:

(1) exposing the electrode arrays to the solutions having same or similar solutions or suspensions;

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1), and the resistance of the electrode array with the solutions or suspensions present;

(3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$.

Another aspect of the present invention is directed to a method of calculating the resistance of the electrode arrays from the measured, total electrode resistances for two or more essentially identical electrode arrays (such as, for example arrays A-D in FIG. 1) if the same or similar solutions or suspensions are added to be in contact with the electrode assays, comprising the following steps:

(1) exposing the electrode arrays to the solutions having same or similar solutions or suspensions;

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1) and the resistance of the electrode arrays with the solutions or suspensions present;

(3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$;

(4) calculating the resistances of the electrode arrays using equations (10A, 10B, 10C and 10D)).

In many applications, the solutions or suspensions (for example, cell suspension) applied to each electrode array may have different compositions. For example, cell suspensions of different cell numbers may be used so that the suspensions applied to each electrode array are quite different. Under such cases, the determination of the resistance of the electrode arrays with the cells present would require the determination of the resistance of the electrical connection traces by performing a "reference run" or "calibration run" in which the electrode arrays are exposed to a same, reference solution. From the "reference run", the resistances of the electrical connection traces can be determined. In a separate test, the electrode arrays are exposed to the solutions or cell suspensions of interest and the resistances for the electrode arrays under such conditions are measured with an impedance analyzer or impedance measuring circuit. The resistance of the electrode arrays with such cell suspensions present can be determined (or continuously determined) from the measured resistance by subtracting the sum of the resistance of the electronic switches and the resistance of the electrical connection traces for corresponding electrode arrays from the measured resistances.

Thus, another aspect of the present invention is directed to a method of calculating the resistance of the electrode arrays from the total electrical resistances measured at an impedance analyzer for essentially identical electrode arrays (such as electrode arrays A-D in FIG. 1 used as an example) if different solutions or suspensions of interest are applied to the electrode assays, comprising the following steps:

(1) exposing the electrode arrays to the solutions having same or similar solutions or suspensions (reference solutions);
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1) and the resistance of the electrode arrays with the reference solutions present;
(3) solving for the resistances of electrical connection traces using equation (15) and equations (9B), (9C) and (9D), noting in the calculation with equation (15), the geometrical relationships between the electrode arrays of FIG. 1 are used to determine the factor $\alpha_{A-D}$, $\alpha_{B-D}$ and $\alpha_{C-D}$;
(4) applying the solutions or suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the solutions or suspensions of the interest present,
(5) Calculating the resistance of the electrode arrays using equations (10A), (10B), (10C) and (10D) by subtracting the electronic switch resistances and the resistances of electrical connection traces from the measured resistances in the step (4).

Note that in above method, the steps of exposing the electrode arrays to reference solutions for the determination of the resistances of electrically conductive traces (step (1), (2) and (3)) may be performed before or after the steps of applying the solutions or suspensions of interest to the electrode arrays and measuring the total electrical resistance (step (4)). For example, step (4) may be performed first. After that, the solutions or suspensions of the interest may be removed from the electrode array. The reference solutions can then be added to the electrode arrays (step (1)). Step (2) and step (3) can be then performed to determine the resistances of electrical connection traces. Finally, Step (5) can be done.

In another approach, step (1) and (2) can be performed ahead of step (4).

Another aspect of the present invention is directed to a method of determining the resistance of the electrode arrays with the cells present for a cell-based assay based on the total electrical resistance measured at an impedance analyzer for essentially identical electrode arrays. In this method, the electrode arrays are exposed to a same, reference solution (for example, a same cell culture medium that does not contain any cells) and electrical measurement is conducted to determine the resistance of electrical connection traces. With the resistances of the electrical connection traces determined, electrical resistances of the electrode arrays with cell suspensions added to electrode arrays can be calculated from the total electrical resistances measured at an impedance analyzer. Such total electrical resistance would include the resistance of the electrode arrays with cells present, the resistance of electronic switches and the resistance of electrical connection traces. The method comprises following steps (1) exposing the electrode arrays to the solutions having same or similar solutions or suspensions (reference solutions);
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1) and the resistance of the electrode arrays with the reference solutions present;
(3) solving for the resistances of electrical connection traces using equation (15) and equations (9B), (9C) and (9D), noting in the calculation with equation (15), the geometrical relationships between the electrode arrays in FIG. 1 are used to determine the factor $\alpha_{A-D}$, $\alpha_{B-D}$ and $\alpha_{C-D}$;
(4) applying the cell suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the cell suspensions of the interest present,
(5) Calculating the resistance of the electrode arrays using equations (10A), (10B), (10C) and (10D) by subtracting the electronic switch resistances and the resistances of electrical connection traces from the measured resistances in step (4).

Note that in above method, the steps of exposing the electrode arrays to reference solution for the determination of the electrical resistance of electrically conductive traces (step (1), (2) and (3)) may be performed before or after the steps of applying the solutions of interest or cell suspensions of interest to the electrode arrays and measuring the total electrical resistance (step (4)). For example, step (4) may be performed first, followed by steps (1) and (2). In one approach, after step (4), the cell suspensions of the interest may be removed from the electrode array. Then reference solutions can be added to the electrode arrays. In another approach, after step (4), the cells are all lysed with some cell lysis solutions so that the electrodes are exposed to the same, reference solutions for the measurement and calculation of step (2) and (3). And then, step (5) is performed to determine the electrical resistance of electrode arrays with the cell suspensions of interest present.

The determination of the resistances of the electrical conductive traces for the electrode arrays that essentially identical electrode arrays may be, or may not be, part of the monitoring of cell-substrate impedance for cell-based assays. It depends on how the impedance data (measured at a single frequency or multiple frequencies, measured at multiple time points) of the electrode arrays is analyzed.

In some assays, one is interested in the relative change in the resistance or impedance of the electrode arrays with the cells present relative to the baseline resistance or impedance. For such cases, it is preferred to determine the resistance (or impedance) of the electrode arrays from the total, measures resistance (or impedance) by subtracting the resistance of the electrical conductive traces and the resistance of electronic switches. Thus, determination of the resistances or impedance of the electrically conductive traces may be required.

In some other assays, one is interested in the absolute changes in the resistance (or impedance) of the electrode arrays with cells present relative to the baseline resistance (or impedance). In these cases, one can directly subtract the measured resistance or impedance for the baseline condition from the measured resistance or impedance for the condition that the cells are present on the electrode arrays. The contribution of the resistance (or impedance) of the electronic switches and the resistance (or impedance) of the electrically conductive traces to the total measured resistance (or impedance) values is cancelled out in such subtractions. Thus, there is no need for determining the resistances of the electrically conductive traces.

In some assays, one is interested in calculating the Cell Index or Cell Number Index based on the monitored impedance values. Depending on which method is used for calculating the Cell Index, it may, or may not, be necessary to determine the resistances of the electrically conductive traces. For example, for the Cell Index calculation method (A) described above, the resistances of the electrically conductive traces are needed, in order to remove the effect of the resistance of the electrically conductive traces on the analysis of the relative change of the resistance or impedance. In another example, for the Cell Index calculation method (F) described above, there is no need to determine the resistances of the electrically conductive traces since the effect of the resistance of the electrically conductive traces is canceled out in the calculations.

The monitoring of the cell-substrate impedance may be or may not be based on the change with respect to the baseline impedance (or resistance). For example, a cell-based assay is performed to assess the effect of a test compound on the cells. One method in performing such an assay is by monitoring of the cell-substrate impedance and determining the change in the cell-substrate impedance before and after the addition of the test compound to the cells. The monitoring of cell-substrate impedance can be performed at a single frequency point or multiple frequency points, at a single time point or multiple time points after drug addition. For example, the impedance is first measured at a single frequency or multiple frequencies for the electrode arrays with the cells present just before addition of test compound. The test compound is then added to the cells. The impedance is then measured again at the same single frequency or multiple frequencies for the electrode arrays with the cells after the addition of test compound. Such post-compound addition measurement may be performed for many time points continuously in a regular or irregular time intervals. The change in the cell-substrate impedances can be determined or quantified by subtracting the impedance(s) (resistance and/or reactance) measured before addition of the test compound from the impedance(s) (resistance and/or reactance) measured after addition of the test compound. If the measurement is done at multiple frequencies, a single parameter or multiple parameters may be further derived for each time point after compound addition based on the calculated change in the cell-substrate impedances. Such parameters are used to quantify the cell changes after compound addition. Such approaches can be used further to analyze the responses of the cells to a test compound at multiple concentrations to derive dose-dependent response curves.

Normalized Cell Index, Delta Cell Index

A "Normalized Cell Index" at a given time point is calculated by dividing the Cell Index at the time point by the Cell Index at a reference time point. Thus, the Normalized Cell Index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

A "delta cell index" at a given time point is calculated by subtracting the cell index at a standard time point from the cell index at the given time point. Thus, the delta cell index is the absolute change in the cell index from an initial time (the standard time point) to the measurement time.

Cell Change Index

The time-dependent cellular response (including cytotoxicity response) may be analyzed by deriving parameters that directly reflect the changes in cell status. For example, time dependent cellular response may be analyzed by calculating the slope of change in the measured impedance responses (that is equivalent to the first order derivative of the impedance response with respect to time, impedance response here can be measured impedance data or derived values such as cell index, normalized cell index or delta cell index). In another example, the time-dependent cellular responses (including cytotoxicresposnes) responses may be analyzed for their higher order derivatives with respect to time. Such high order derivatives may provide additional information as for how cells responding to different compounds and as for the mechanisms of compound action.

As an example, we describe how one can to derive a parameter, called Cell Change Index, based on the real time, quantitative information (i.e., cell index, CI) about biological status of cells in the wells provided from RT-CES system. This new parameter, Cell Change Index (CCI), can effectively link time dependent cell index I with cell status, is calculated as, $$CCI(t) = \frac{dCI(t)}{CI(t) \cdot dt}. \tag{5}$$

Thus CCI is the normalized rate of change in cell index. CCI values can be used to quantify the cell status change. For cells in an exponential growth under regular cell culture condition, the cell index determined by a cell-substrate impedance monitoring system described herein is expected to be a proportionate measure of the cell number in the well since the cell morphology and average extent of cell adhesion to the electrode surfaces among the whole cell population do not exhibit significant changes over time. Thus, the cell index (CI) increase with time following an exponential function, such that $$CI(t) = CI(0) * 2^{\frac{t}{DT}} \qquad (6)$$

where DT is the cell doubling time. For such exponential growth culture, CCI(t) is a constant, giving $$CCI(t) = \frac{0.693}{DT} \approx \frac{0.7}{DT}. \qquad (7)$$

Thus, several types of CCI(t) can be classified as:
 (1) If CCI is about 0.7/DT, cell index increases in the same rate as that expected for an exponential growth of the cells.
 (2) If CCI>>0.7/DT, cell index increases faster than that expected for an exponential growth (or log growth) of the cells. This indicates that cells may grow faster than regular exponential growth, or cells may exhibit some morphology change (e.g. cell spreading out or adhering better to the electrode surfaces), leading to large impedance signal, or both of above effects, or there may be other cell behaviors occurring particular to the assay or culture conditions.
 (3) If CCI is more than zero but somewhat smaller than 0.7/DT, then cell index increases in the rate slowed than that expected for an exponential growth. This indicates that cell growth rate may be slowed down relative to exponential growth, or cell growth may be somewhat inhibited by chemical compounds added to the culture media or by other cell culture parameters, or that certain populations of cells are dying off and detaching from the electrode surfaces, or there may be other cell behaviors occurring particular to the assay or culture conditions.
 (4) If CCI is about zero, then cell index shows a near constant value. This may indicate that the cell growth is nearly-completely inhibited. For example, all the cells are arrested at certain points of cell cycle and are not progressing further. Or, this may indicate that the number of cells dying off in the culture is nearly as the number of newly-divided cells. Alternatively this may indicate that cells reach stationary phase of cell culture. Alternatively this may indicate that number of cells are above the detection upper limit of the cell-substrate impedance monitoring system. There is also the possibility of other cell behaviors occurring particular to the assay or culture conditions.
 (5) If CCI is negative, then the cell index is decreasing with time, showing the cells losing attachment to the electrode surface or changing their morphology.
 (6) If CCI is very negative, then the cell index decreases rapidly with time, showing that either cells lose attachment to the electrode surfaces quickly or cells change their morphology very quickly.

D. Methods for Performing Real-Time Cell-Based Assays

The present invention provide cell-based assays that can be performed in real time to assess cell proliferation, cell growth, cell death, cell morphology, cell membrane properties (for example, size, morphology, or composition of the cell membrane) cell adhesion, and cell motility. Thus the assays can be cytotoxicity assays, proliferation assays, apoptosis assays, cell adhesion assays, cell activation or stimulation assays, anti-cancer compound efficacy assays, receptor-ligand binding or signal transduction analysis, assays of cytoskeletal changes, assays of cell structural changes (including but not limited to, changes in cell membrane size, morphology, or composition), cell quantification, cell quality control, time-dependent cytotoxicity profiling, assays of cell differentiation or de-differentiation, detection or quantitation of neutralizing antibodies, specific T-cell mediated cytotoxic effect assays, assays of cell adhesivity, assays of cell-cell interactions, analysis of microbial, viral, or environmental toxins, etc.

The assays are real-time assays in the sense that cell behavior or cell status being assayed can be assessed continuously at regular or irregular intervals. Cell behaviors, cell responses, or cell status can be assayed and the results recorded or displayed within seconds to minutes of their occurrence. The cell response during an assay can be monitored essentially continuously over a selected time period. For example, a culture can be monitored every five to fifteen minutes for several hours to several days after addition of a reagent. The interval between impedance monitoring, whether impedance monitoring is performed at regular or irregular intervals, and the duration of the impedance monitoring assay can be determined by the experimenter.

Thus, the cell-based impedance assays of the present invention avoid inadvertently biased or misleading evaluation of cell responses due to the time point or time points chosen for sampling or assaying the cells. In addition, the assays do not require sampling of cell cultures or addition of reagents and thus eliminate the inconvenience, delay in obtaining results, and error introduced by many assays.

Descriptions of cell-substrate monitoring and associated devices, systems and methods of use have been provided in U.S. provisional application No. 60/379,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, entitled "Impedance based devices and methods for use in assays", filed on Jul. 18, 2003; PCT application number PCT/US03/22537, entitled "Impedance based apparatuses and methods for analyzing cells and particles", filed on Jul. 18, 2003; U.S. patent application Ser. No. 10/705,447, entitled "Impedance based devices and methods for use in assays", filed on Nov. 10, 2003; U.S. patent application Ser. No. 10/987,732 U.S. patent application Ser. No. 10/705,615, entitled "Impedance based apparatuses and methods for analyzing cells and particles", filed on Nov. 10, 2003, all incorporated herein by reference for their disclosure of cell-substrate impedance devices, systems, and methods of use. Additional details of cell-substrate impedance monitoring technology is further disclosed in the present invention.

In brief, for measurement of cell-substrate or cell-electrode impedance using the technology of the present invention, cell-substrate impedance monitoring devices are used that have microelectrode arrays with appropriate geometries fabricated onto the bottom surfaces of wells such as microtiter plate wells, or have a similar design of having multiple fluid containers (such as wells) having electrodes fabricated on their bottom surfaces facing into the fluid containers. Cells are introduced into the fluid containers of the devices, and make contact with and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue electronic readout signals can be measured automatically and in real time, and can be converted to digital signals for processing and for analysis.

Preferably, cell-substrate impedance assays are performed using a system of the present invention that comprises a device of the present invention, an impedance monitor, a device station that comprises electronic circuitry and engages the device and the impedance analyzer, and a software program that controls the device station and records and analyzes impedance data.

Using a system of the present invention, a cell index can optionally be automatically derived and provided based on measured electrode impedance values. The cell index obtained for a given well reflects: 1) how many cells are attached to the electrode surfaces in this well, and 2) how well (tightly or extensively) cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

In one aspect of the present invention, a method is provided for performing cell-based assays, comprising: a) providing a cell-substrate impedance monitoring device of the present invention that comprises two or more electrode arrays, each of which is associated with a fluid container of the device; b) attaching the device to an impedance monitor; c) introducing cells into one or more fluid containers of the device; and d) monitoring cell-substrate impedance of at least one of the fluid containers that comprises an electrode array and cells. Preferably, impedance is monitored from the at least one fluid container to obtain impedance measurements at at least three time points. Preferably, impedance measurements or impedance values derived from impedance measurements from at least three time points are plotted versus time to generate one or more impedance curves for the one or more fluid containers.

In a related aspect of the present invention, a method is provided for performing cell-based assays in an impedance-monitoring system, comprising: a) providing a cell-substrate impedance monitoring system of the present invention that comprises a device having two or more electrode arrays, each of which is associated with a well of the device; b) introducing cells into one or more wells of the device; and c) monitoring cell-substrate impedance of at least one of the wells that comprises an electrode array and cells. Preferably, impedance is monitored from the one or more wells of the device to obtain impedance measurements at at least three time points. Preferably, impedance measurements or impedance values derived from impedance measurements from at least three time points are plotted versus time to generate one or more impedance curves for the one or more wells.

The method can be used to assay cell status, where cell status includes, but is not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. The cell-based assays that be performed with above methods include, but are not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, and cell-based assays for screening and measuring ligand-receptor binding.

In preferred embodiments of this aspect of the present invention, cells are added to at least two fluid containers of a device, each of which comprises an electrode array, and impedance is monitored from at least two wells that comprise cells and an electrode array.

The cells used in the assay can be primary cells isolated from any species or cells of cell lines. Primary cells can be from blood or tissue. The cells can be engineered cells into which nucleic acids or proteins have been introduced. In some embodiments, different cell types are added to different wells and the behavior of the cell types is compared.

An impedance monitoring assay can be from minutes to days or even weeks in duration. Preferably, impedance is monitored at three or more time points, although this is not a requirement of the present invention. Impedance can be monitored at regular or irregular time intervals, or a combination of irregular and regular time intervals. In one embodiment of a cell-based impedance assay, the cell-substrate impedance is monitored at regular time intervals. In some embodiments of the present invention, impedance is monitored at irregular intervals and then at regular intervals during a particular time window of the assay. Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

In yet another aspect, the present invention provides a method for performing real-time cell-based assay investigating the effect of a compound on cells, comprising: a) providing an above described system; b) seeding the cells to the wells of multiple-well devices; c) adding the compound to the wells containing cells; d) monitoring cell-substrate impedance before and after adding the compound at a regular or irregular time interval; wherein the time dependent impedance change provides information about time dependent cell status before addition of the compound and about time dependent cell status under the interaction of the compound. Information about cell status includes, not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

In one embodiment of the above cell-based assay, the cell-substrate impedance is monitored at regular time intervals. In exemplary embodiments, the impedance is measured at a regular 2 hour, 1 hour, 30 min or 15 min time interval before and after adding the compound. In the present application, a real-time assay means that one can perform the measurement on cell-substrate impedance with various time resolutions, for example, measurement taking place at a longer time interval such as every hour or every two hours, or at a shorter time interval every minute or a few minutes. Real-time assay does not mean that the measurements are provided in a continuous, uninterrupted fashion. In another word, real-time assay does not mean that the measurements are performed at every single moment.

Figure 2:
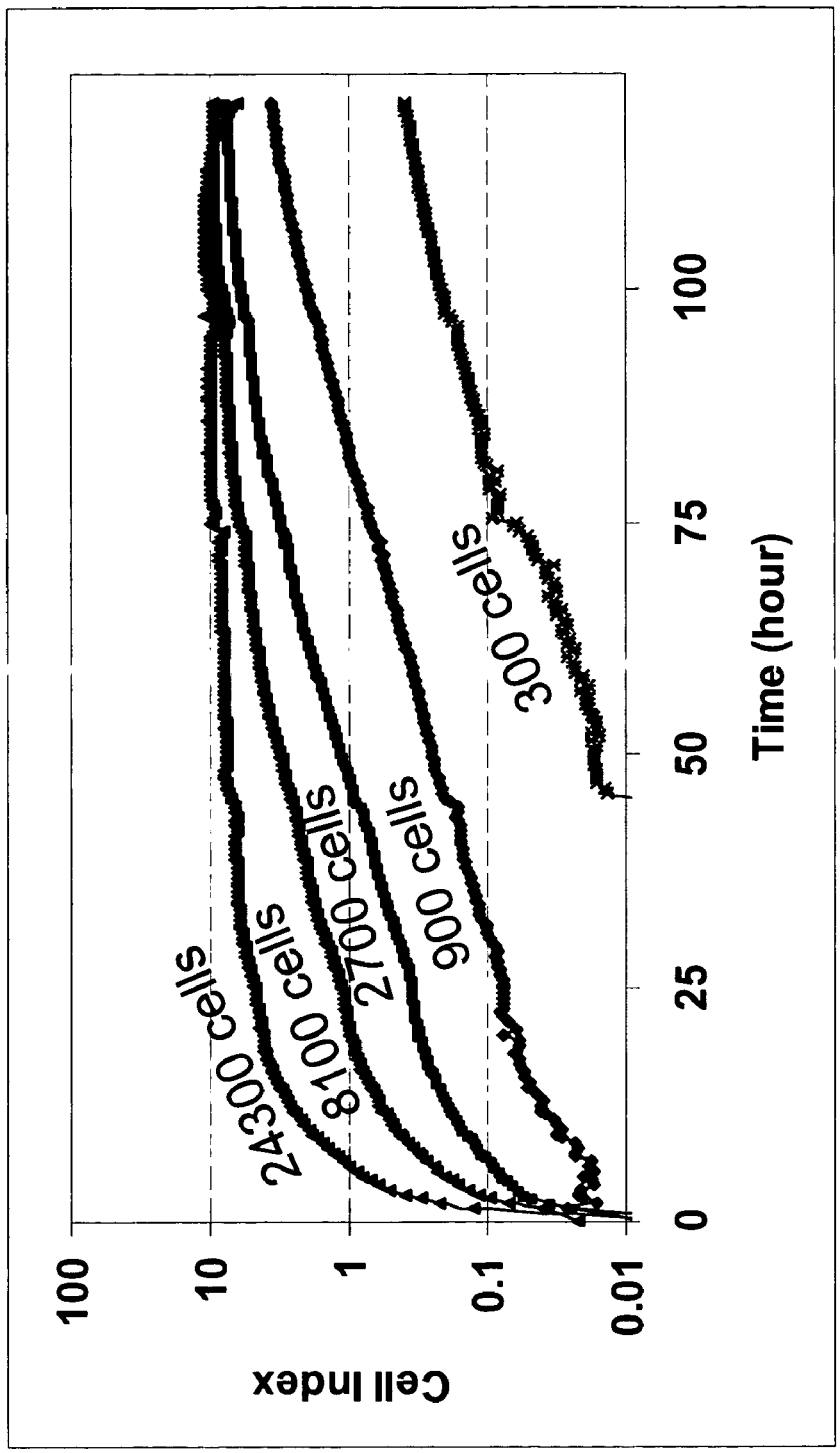
FIG. 2 shows real-time monitoring of proliferation of H460 cells seeded at different initial cell seeding numbers on a cell substrate impedance monitoring system of the present invention. The cell proliferation was continuously recorded every 15 minutes for over 125 hours. The cell growth curves in the log scale show exponential cell growth or cells in the stationary phase.

FIG. 2 depicts results of the use of methods of the present invention to monitor cell proliferation. In this experiment, H460 cells were introduced into wells of a 16 well device of a cell-substrate impedance monitoring system of the present invention, with different wells receiving different initial cell seeding numbers. The device was engaged with a device station of the system that was in a tissue culture incubator that kept a temperature of 37 degrees C and an atmosphere of 5% $CO_2$. Cell-substrate impedance was monitored at 15 minute intervals for 125 hours. The cell index was calculated by the system for each time point and displayed as a function of time to give cell growth (proliferation) curves for each cell seeding number. The cell growth curves were plotted on a log scale showing exponential growth phases and stationary phases.

Figure 3:
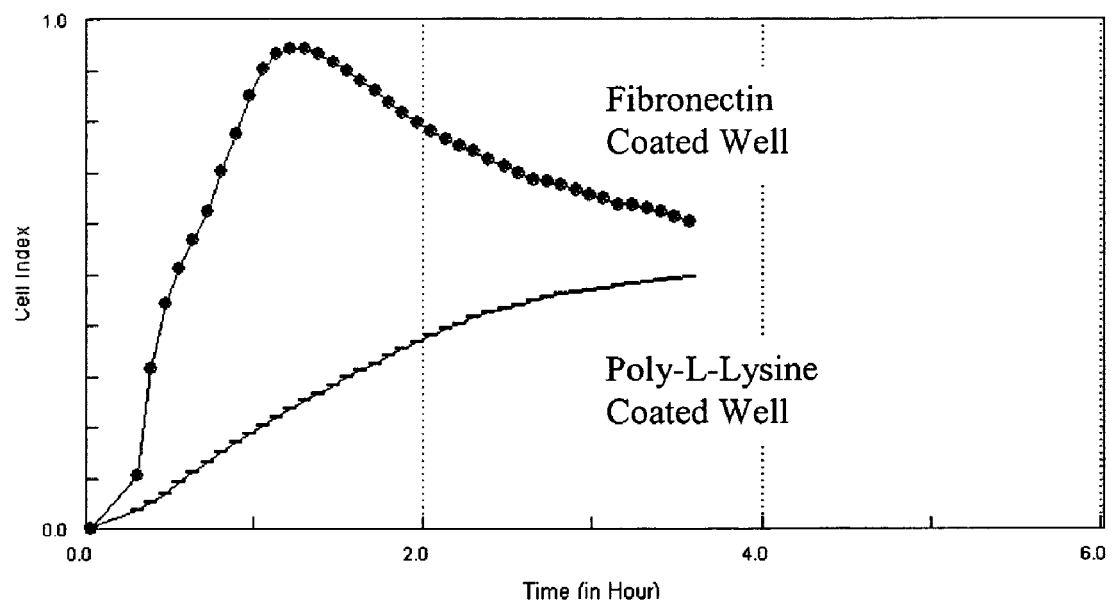
FIG. 3 shows real time monitoring of cell attachment and spreading of NIH3T3 cells using a cell-substrate impedance monitoring system of the present invention. The cells were seeded onto devices coated with either poly-L-lysine or fibronectin. The cell attachment and cell spreading processes on the different coating surfaces were monitored every 3 minutes for over 3 hours in real time.

FIG. 3 depicts results of real-time monitoring of cell attachment and spreading of NIH3T3 cells. The cells were seeded onto cell-substrate impedance monitoring devices of the present invention that were coated with either poly-L-lysine or fibronectin. The device was connected to a device station that was in a tissue culture incubator that kept a temperature of 37 degrees C. and an atmosphere of 5% $CO_2$. Cell attachment and cell spreading on the difference coating surfaces were monitored by measuring impedance on the cell-substrate monitoring system. Impedance was monitored in real time every 3 minutes for 3 hours. The cell index for each time point was calculated by the impedance monitoring system and plotted as a function of time.

Figure 4:
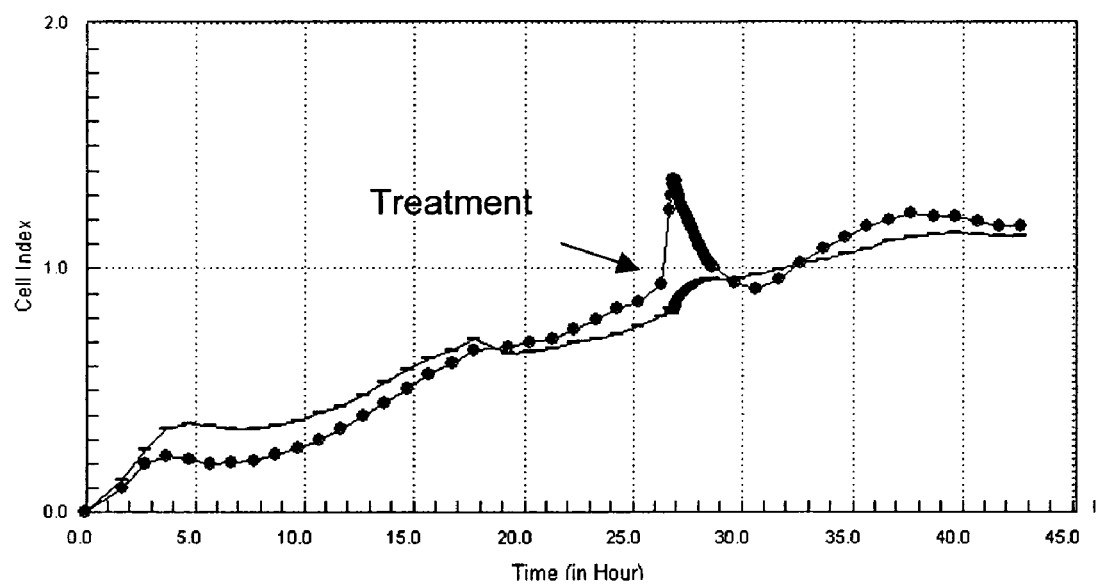
FIG. 4 shows real-time monitoring of morphological changes in Cos-7 cells using a cell-substrate impedance monitoring system of the present invention. The cells were serum starved for 8 hours and stimulated with or without 50 ng/mL EGF. Changes in cell morphology were monitored at 3 min intervals for 2 hours and then 1 hour interval for 14 hours. The initial jump in the signal in EGF-treated cells is due to membrane ruffling and actin dynamics in response to EGF. The arrow indicates the point of EGF stimulation.

FIG. 4 shows the results of an experiment monitoring morphological changes in Cos-7 cells in response to stimulation with epidermal growth factor (EGF). Cells were seeded in wells of a 16 well monitoring device of the present invention that engaged a device station of a cell-substate monitoring system. The device station was positioned in an incubator held at 37 degrees C. and 5% $CO_2$. The cells were serum starved for 8 hours and then stimulated with 50 nanograms/mL of EGF. Control cells did not receive EGF. Impedance was monitored at 3 minute intervals for 2 hours and then at 1 hour intervals for 14 hours. The cell index was calculated by the system and plotted as a function of time. An initial jump in cell index is seen in EGF-treated cells due to membrane ruffling and actin dynamics in response to EGF. The arrow indicates the point of EGF addition.

D.1. Cell Proliferation Assays

The present invention provides methods for performing cell proliferation assays. In these assays, an increase in monitored impedance is indicative of an increases cell number. The impedance measurements or impedance values derived from impedance measurements can be plotted versus time to obtain growth curves for cells growing in a fluid container of a cell-substrate monitoring device of the present invention.

The present invention provides a method of generating at least one cell growth curve, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at three or more time points after adding the cells to the one or fluid containers; and plotting the impedance measurements or values for the three or more time points versus time to generate at least one growth curve for the cells in the one or more fluid containers.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells to one or more wells of the system; monitoring impedance from the one or more wells to obtain impedance measurements at three or more time points after adding cells to the one or more wells; and plotting impedance measurements or impedance values for the three or more time points versus time to generate a growth curve for the cells in the one or more wells.

Preferably, using a device or system of the present invention, impedance is monitored at four or more time points, in which at least one of the four or more time points is measured from a fluid container prior to adding cells to the fluid container. Preferably, impedance is monitored at regular or irregular time intervals for an assay period of from minutes to days. In many cases, proliferation assays can be performed by monitoring impedance for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

A growth curve can be generated by plotting impedance measurements versus time, or by plotting cell index values that are calculated from impedance measurements, such as normalized cell index values or delta cell index values versus time. The impedance measurement or cell index axis (typically the y-axis) can optionally use a log scale.

An impedance value can be any indices of impedance derived from impedance measurement, including, as nonlimiting examples, a cell index, a normalized cell index or a delta cell index. In certain embodiment, impedance value can also be a "raw" measured or monitored impedance value. Cell index (including normalized and delta cell index) can be a useful value for plotting growth curves, as it relates impedance measurements to cell number. For cell growth curves, a delta cell index for a given time point can be derived by subtracting the cell index at a baseline point, such as a time point after cell attachment and just before log phase growth, from the cell index measurement at the given time point. Preferably, determinations of impedance values and generating growth curves based on impedance measurements or values can be performed by software, and preferably by software that interfaces directly with the impedance analyzer. For example, where the growth assays are performed by a system of the present invention, impedance values (where used) can be measured or derived or calculated and growth curves generated by a software program that controls and receives data from the impedance analyzer.

A growth curve generated from impedance measurements or cell index values (including normalized cell index values and delta cell index values) can optionally be used to calculate one or more kinetic parameters of cell growth or behavior. For example, a growth curve can be used to calculate the length of a lag phase, cell attachment time, cell attachment rate, or a cell doubling time.

FIG. 2 shows real-time monitoring of proliferation of H460 cells seeded at different initial cell seeding numbers on a cell substrate impedance monitoring system of the present invention. The cell proliferation was continuously recorded every 15 minutes for over 125 hours. The cell growth curves in the log scale show exponential cell growth or cells in the stationary phase. The cell index curve shown here can be used to calculate cell doubling time (DT). For example, taking the cell index for initial seeding density of 900 cells. It took approximately 57 hrs (from about 55 hr to about 112 hr) for cell index to increase from 0.3 to 3.0. Thus, the cell index doubling time is about 17.2 hrs (=log(2)*57). Assuming that there is a linear correlation between cell number and cell index in this range, then cell doubling time is the same as the cell index doubling time. Thus, the cell doubling time (DT) is about 17.2 hrs. Another simple method to calculate the cell index doubling time is just to figure out how long t takes cell index to double. For example, for the cell index curve with initial seeding density of 900 cells. It took about 17 hrs for cell index to change from 1.0 (at about 82 hrs) to 2.0 (at about 99 hrs). Thus the cell index doubling time is 17 hrs.

FIG. 3 shows real time monitoring of cell attachment and spreading of NIH3T3 cells using a cell-substrate impedance monitoring system of the present invention. The cells were seeded onto devices coated with either poly-L-lysine or fibronectin. The cell attachment and cell spreading processes on the different coating surfaces were monitored every 3 minutes for over 3 hours in real time. Using the cell index curve showing in FIG. 3, we can calculate the cell attachment time and cell attachment rate. Initial cell index increase immediately following cell addition to the ells (at time=0 in FIG. 3) reflects the cell spreading and attachment process. The time it takes for cell index to increase from zero to a maximum value or a some-what constant value (assuming that there is no cell division or growth in this initial time period following cell seeding) is the cell attachment time. For NIH3T3 cells, cell attachment time in a fibronectin coated well is about 1.2 hrs, as compared with the attachment time of about 3.5 hrs for the same cells in a poly-L-lysine coated well. Cell attachment rate is defined as 1 over the cell attachment time. Thus, cell attachment rate is about 0.83 $hr^{-1}$ and about 0.29 $hr^{-1}$ respectively, for NIH3T3 cells attaching to a fibronectin-coated well and a poly-L-lysine coated well.

FIG. 4 shows real-time monitoring of morphological changes in Cos-7 cells using a cell-substrate impedance monitoring system of the present invention. The cells were serum starved for 8 hours and stimulated with or without 50 ng/mL EGF. Changes in cell morphology were monitored at 3 min intervals for 2 hours and then 1 hour interval for 14 hours. The initial jump in the signal in EGF-treated cells is due to membrane ruffling and actin dynamics in response to EGF. The arrow indicates the point of EGF stimulation. Using the cell index curve showing in FIG. 4, we can calculate the cell attachment time and cell attachment rate. Initial cell index increase immediately following cell addition to the ells (at time=0 in FIG. 4) reflects the cell spreading and attachment process. The time it takes for cell index to increase from zero to a maximum value or a some-what constant value (assuming that there is no cell division or growth in this initial time period following cell seeding) is the cell attachment time. For Cos-7 cells shown here, the cell attachment time is about 4 hrs. Cell attachment rate, as defined: 1 over the cell attachment time, is about 0.25 $hr^{-1}$ for Cos-7 cells. Furthermore, we can also calculate the length of lag phase. The lag phase corresponds to the time it takes for cells to enter the growth phase after the completion of cell attachment process. Based on the cell index curve in Figure, cell attachment was complete at about 4 hrs. The cells showed significant increase in cell index—indicating cell growth, at around 9 hrs. Thus, the length of lag phase is about 5 hrs (=9 hr–4 hr).

Comparing Growth Curves of Two of More Cell Types

Two or more cell types can be seeded to separate wells in a proliferation assay using the methods of the present invention to generate growth curves of the two or more cell types. The growth curves or kinetic parameters derived from the growth curves of the cell types can be compared.

In this aspect, the invention includes a method of generating growth curves for at least two cell types, comprising: providing a device of the present invention having two or more electrode arrays, each of which is associated with a fluid container of the device; attaching the device to an impedance analyzer; adding cells of two or more cell types to two or more fluid containers of the device, in which at least one of the two or more fluid containers receives one cell type and at least one other of the two or more fluid containers receives a different cell type, to provide two or more fluid containers comprising two or more different cell types; monitoring impedance from the two or more fluid containers comprising different cell types at three or more time points after adding the two or more cell types to the two or more fluid containers; and plotting impedance measurements or impedance values for the three or more time points versus time to generate a growth curve for the two or more cell types.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells of two or more cell types to two or more wells of the device, in which at least one of the two or more wells receives one cell type and at least one other of the two or more wells receives a different cell type, to provide two or more wells comprising two or more different cell types; monitoring impedance from the two or more wells comprising different cell types at three or more time points after adding the two or more cell types to the two or more wells; and plotting impedance measurements or impedance values for the three or more time points versus time to generate a growth curve for the two or more cell types.

As, described above for proliferation assays, impedance is preferably monitored using an impedance monitoring device or system at four or more time points, in which at least one of the four or more time points is measured from fluid containers prior to adding cells to the fluid containers. Preferably, impedance is monitored at regular or irregular time intervals for an assay period of from minutes to days, for example, for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

Growth curves for different cell types can be generated as described above. Impedance or impedance values, such as cell index, normalized cell index, or delta cell index can be plotted versus time. The impedance measurement or cell index axis (typically the y-axis) can optionally use a log scale.

A growth curve generated from impedance measurements or cell index values (including normalized cell index values and delta cell index values) can optionally be used to calculate one or more kinetic parameters of cell growth or behavior. For example, a growth curve can be used to calculate the duration of a lag phase, cell attachment time, cell attachment rate, or a cell doubling time.

Preferably, the growth curves of the two or more different cell types, or kinetic parameters derived from the growth curves of the two or more different cell types, are compared to determine differences among the cell types in proliferation patterns or rates, or in kinetic parameters that can be derived from growth curves. The different cell types used can be any cell types, including primary cells isolated from blood or tissue of an animal or human, or cells from cell lines. For example, proliferation rates of two types of primary cancer cell can be compared, or of primary cancer cells of the same type but different grades. In another example, primary cells of individuals of different genotypes can be compared. In another example, proliferation rates of primary or cell line stem cells can be compared. In yet another example, growth curves or parameters of control and genetically modified cells of a cell line can be compared. In yet another example, growth curves or parameters of cells infected with virus and control cells can be compared.

D.2. Quantifying Cells Using Cell-Substrate Impedance Devices

The present invention also includes a method of quantifying cells, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at one or more time points after adding the cells to the one or more fluid containers; deriving a cell index for the one or more time points; and using the cell index to determine the number of cells in the one or more fluid containers at at least one of the one or more time points. The cell index is used to determine the number of cells using a formula that relates cell index to cell number, in which the formula is obtained by: providing a device for cell-substrate monitoring, attaching the device to an impedance monitor; adding cells to one or more fluid containers of the device; measuring impedance of the one or more fluid containers comprising cells; calculating a cell index from the impedance measurements; determining the number of cells of said at least one fluid container at the time of impedance monitoring by a means other than impedance monitoring; and deriving a formula that relates the number of cells of the one or more fluid containers at the two or more time points with the impedance measurements at the two or more time points.

In the embodiment of above method for obtaining the formula, sometime, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemacytometer counting, flow cytometry, or Coulter counting.

The method can also be practiced using an impedance monitoring system of the present invention, where the system includes a multi-well cell-substrate impedance monitoring device, an impedance analyzer, a device station, and a software program. The method includes; providing a multi-well cell-substrate impedance measuring system; adding cells one or more wells of the system; monitoring impedance from the one or more wells comprising cells at one or more time points after adding the cells to the one or more wells; deriving a cell index for the one or more time points; and using the cell index to determine the number of cells in said at least well at at least one of said one or more time points.

The cell index is used to determine the number of cells using a formula that relates cell index to cell number, in which the formula is obtained by: providing a system for cell-substrate monitoring, where the system comprises at least one multi-well cell-substrate impedance monitoring device, adding cells to one or more wells of a device of the system; measuring impedance of the one or more wells comprising cells at two or more time points; calculating a cell index from the impedance measurement at the two or more time points; determining the number of cells of the one or more wells at the two or more time points by a means other than impedance monitoring; and deriving a formula that relates the number of cells of the one or more wells at the two or more time points with the impedance measurements at the two or more time points.

In the embodiment of above method for obtaining the formula, sometime, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemacytometer counting, flow cytometry, or Coulter counting.

Formulas relating cell index (including normalized cell index and delta cell index, which can also be used) to cell number for a given cell type can be used to quantitate cells of that type in assays using a cell-substrate impedance monitoring device, such as a device described herein. Generally, for a give cell type and for cells under similar physiological conditions, the derived formulas relating cell index to cell number can be used in subsequent assays. There is no need to obtain the formula each time when an assay is performed. However, it is worthwhile to point that the formula can only be valid as long as the cells are under same physiological conditions in the assays where the formula was derived and where the formula is used. If the cell condition is different, for example, the composition of culture media is changed, or the cell attachment surface is altered, then the formula will not hold. In another example, if cells are in log-growth phase in one assay and are in stationary phase in another assay, then the formula may not hold. Another point worth mentioning here is that relates the fact the derived cell index or impedance also depends on cell attachment quality on the surface as well as cell morphology. If cell morphology or cell attachment changes during an assay, then one need to distinguish between the changes caused by change in cell number or in cell morphology or in cell attachment.

Figure 8:
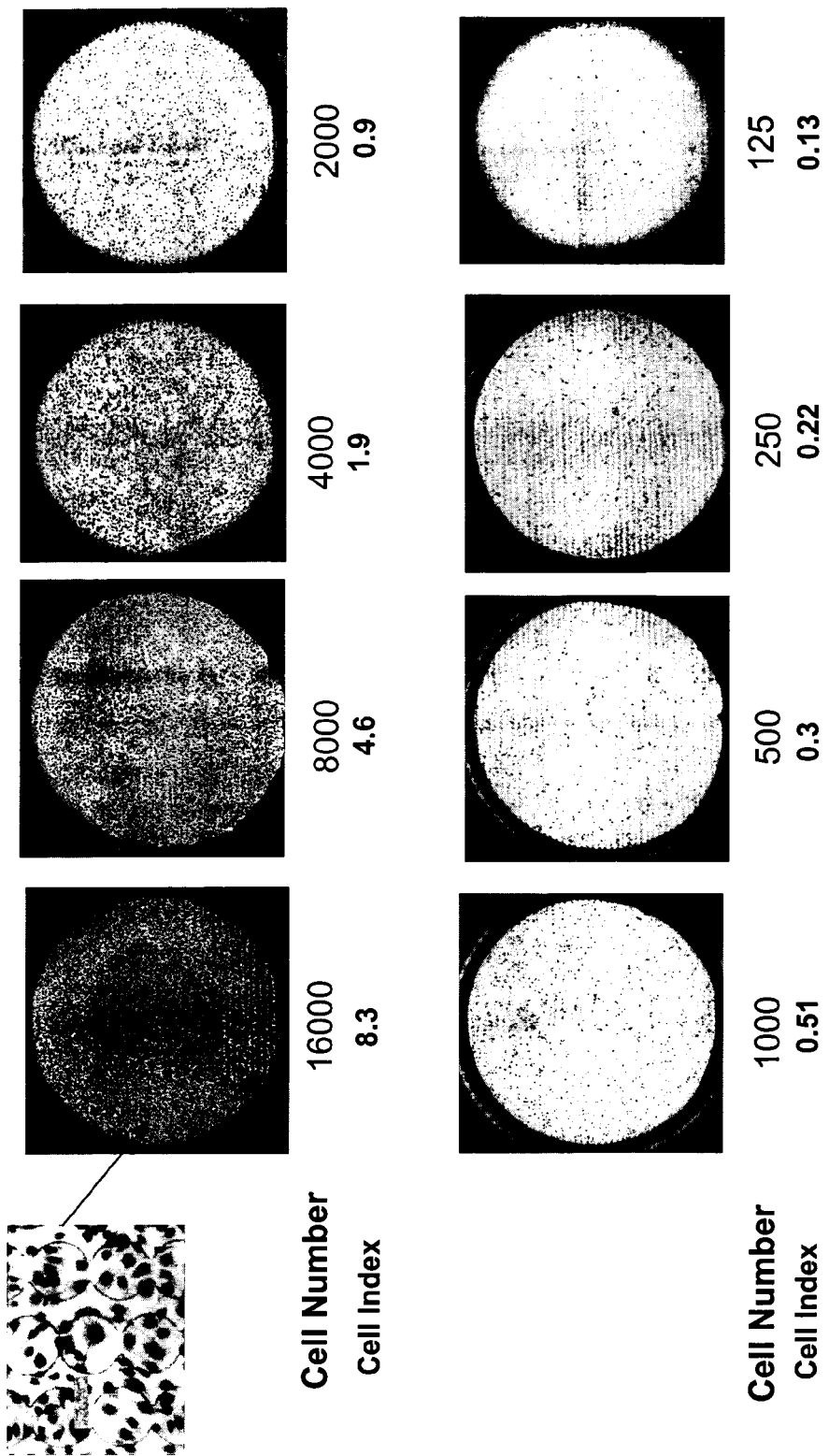
FIG. 8 shows titration of NIH3T3 cells on the devices of the present invention. The indicated cell number of cells were seeded into microtiter devices fabricated with electronic sensor arrays shown in FIG. 1B. The electronic sensor arrays were-precoated with fibronectin. Two hours after seeding, the cell index number was determined using a cell-substrate impedance monitoring system of the present invention.

As an example, we can derive the correlation formula between cell index and cell number for NIH3T3 cells under the experimental conditions. The formula for converting cell index to cell number for this particular case is: Cell number=2000*Cell index−145. To test this formula, we found the error in estimating cell number based on the cell index data shown in FIG. 8 as compared to the seeded cell number is less than 20%.

D.3. Cell-Based Assays to Test the Effects of Compounds on Cells

In yet another aspect, the present invention provides a method for performing a cell-based assay investigating the effect of one or more test compounds on cells, comprising: providing a device of the present invention having two or more electrode arrays, each of which is associated with a fluid container of the device; attaching the device to an impedance analyzer; introducing cells into two or more fluid containers of the device that comprise an electrode array; adding at least one test compound to at least one of the one or more of the fluid containers comprising cells and an electrode array to provide at least one test compound fluid container; providing at least one control fluid container to which cells are added that does not receive test compound; and monitoring cell-substrate impedance of the one or more test compound fluid containers and the one or more control fluid containers at at least three time points after adding the one or more test compounds, and analyzing impedance measurements from the one or more test compound fluid containers and the one or more control fluid containers at at least three time points after adding the one or more test compounds, in which changes in impedance can provide information about cell responses to the one or more test compounds.

In a related aspect the present invention also provides a method for performing a cell-based assay investigating the effect of one or more test compounds on cells, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes; providing a multi-well cell-substrate impedance measuring system; introducing cells into two or more wells of the device; adding at least one test compound to at least one of the one or more of the wells comprising cells to provide at least one test compound well; providing at least one control well to which cells are added that does not receive test compound; monitoring cell-substrate impedance of the one or more test compound wells and the one or more control wells at at least three time points after adding the one or more test compounds; and analyzing impedance measurements from the one or more test compound wells and the one or more control wells at at least three time points after adding the one or more test compounds, in which changes in impedance can provide information about cell responses to the one or more test compounds.

A test compound can be any compound, including a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc. The structure of a test compound can be known or unknown.

Information about cell responses to the one or more test compounds includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance.

The cells used in the assay can be primary cells isolated from any species or can be cells of cell lines. The cells can be genetically engineered cells (For example, cells from a genetically modified organism, such as for example from a "gene knockout" organism, or cells that have been engineered to over-express an endogenous gene or a transgene, or cells whose normal gene expression has been manipulated by use of antisense molecules or silencing RNA.) In some embodiments, different cell types are added to different wells and the behavior of the different cell types in response to one or more compounds is compared.

The cell-based assays that be performed with above methods include, but are not limited to, cell adhesion, apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral, bacterial, or environmental toxin mediated cell pathologic changes or cell death, detection or quantification of neutralizing antibodies, specific T-cell mediated cytotoxic effect, and cell-based assay for screening or measuring ligand-receptor binding.

In the methods of the present invention that investigate test compound effects on cells, impedance is preferably monitored from at least one test compound well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

It is preferable to perform replicate test compound assays in which more than one fluid container of cells receives the same compound at the same concentration. In this case, impedance measurements or values can be averaged for the assayed time points for replicate wells. Preferably, a standard deviation for the averaged values is also calculated.

In the methods of the present invention, analyzing impedance can comprise plotting cell impedance versus time to obtain at least one test compound impedance curve and at least one control impedance curve. Preferably, at least one test compound impedance curve and said at least one control impedance curve are compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Preferably, data from impedance monitoring of a well that comprises cells and a test compound is compared with data from impedance monitoring of a well that comprises cells in the absence of a test compound, however, this is not a requirement of the present invention. For example, it is also possible to compare impedance measurements from one or more time points prior to the addition of compound to compare impedance measurements from one or more time points after the addition of compound. Such comparisons can be used directly to assess the cells' response to a compound. It is also possible to calculate a cell index (or cell number index) using the impedance values obtained.

Methods of calculating a cell index (cell number index) are disclosed herein as well as in parent application U.S. patent application Ser. No. 10/705,447, U.S. patent application Ser. No. 10/987,732, both herein incorporated by reference for disclosures relating to cell number index and its calculation. The cell index calculated from impedance measurements of wells receiving compound can be compared with the cell index calculated from impedance measurements of control wells to assess the effect of a compound on cells. Alternatively, cell index calculated from impedance measurements of wells from one or more time points after the addition of a compound can be compared with the cell index calculated from impedance measurements of wells from one or more time points prior to the addition of a compound to assess the effect of a compound on cells. In some preferred embodiments, the cell index can be used as an indicator of cytotoxicity.

The derivation of cell index from impedance measurements is provided in Section C of the present application. Cell index values (including normalized cell index values and delta cell index values) from at least three time points from at least one test compound well and at least one control well can be plotted versus time to obtain one or more test compound cell index curve and one or more control cell index curves. The one or more test compound cell index curves and the one or more control cell index curves can be compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Cell index values at three or more assay time points for one or more test compound wells and one or more control wells can be used to derive cell change index (CCI) values or a second order derivatives of cell index at three or more assay time points. The calculation of cell change index is provided in Section C of the present application. The value of CCI at a give time point can be determined to be either approximately equal to 0.7, much greater than 0.7, greater than zero and less than 0.7, approximately equal to zero, less than zero, or much less than zero. These values can indicate cell behavior at an assay time point, as CCI approximately equal to 0.7 indicates log rate growth, a CCI much greater than 0.7 indicates faster than log rate growth, a CCI greater than zero and less than 0.7 indicates slower than log rate growth, a CCI approximately equal to zero indicates no growth (a constant cell index), a CCI less than zero indicates cells are detaching from the substrate, and a CCI much less than zero indicates cell are detaching rapidly from the substrate.

For a given assay time point, differences in CCI value between control and compound treated wells can indicate a time at which the compound has an effect on cells, as well as providing information on the type of effect the compound has.

The CCI can further be used to obtain information on the effect of a test compound by plotting CCI versus time for at least three assay time points to obtain a cell change index curve (CCI curve) for at least one control container or well and at at least one test compound container or well. One or more test compound CCI curves can be compared with one or more control CCI curves to obtain information on cell status or behavior in response to said at least one test compound, wherein said cellular status or behavior is at least one of: cell attachment or adhesion status; cell growth or proliferation status; the number of viable cells or dead cells; cytoskeleton change or re-organization; or the number of cells going through apoptosis or necrosis.

Cell-Based Assays with More Than One Cell Type

The present invention also provides methods of comparing the effects of a compound on two or more cell types. In one aspect, the method comprises: providing a device of the present invention having two or more electrode arrays, each of which is associated with a fluid container of the device; attaching the device to an impedance analyzer; introducing cells into two or more fluid containers of the device that comprise an electrode array, wherein at least one of the two or more fluid containers receives one cell type and at least one other of the two or more fluid containers receives a different cell type; adding a test compound to the one or more fluid containers receiving one cell type and adding the test compound to the one or more fluid containers receiving a different cell type to provide at least two test compound fluid containers that comprise cells of different types; providing at least two control fluid containers that do not receive test compound, in which at least one of the control fluid containers receives cells of the one type and at least one of the control fluid containers receives cells of the different type; monitoring cell-substrate impedance of the two or more test compound fluid containers that comprise different cell types and the one or more control fluid containers at at least three time points after adding the one or more test compounds; and analyzing impedance measurements from the two or more test compound fluid containers comprising different cell types and from the one or more control fluid containers at at least three time points after adding the one or more test compounds, in which changes in impedance can provide information about cell responses to the one or more test compounds.

In a related aspect the present invention also provides a method for performing a cell-based assay investigating the effect of one or more test compounds on cells using a cell-substrate impedance monitoring system of the present invention, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes: providing a multi-well cell-substrate impedance measuring system; introducing cells into two or more wells of the device that comprise an electrode array, wherein at least one of the two or more wells receives one cell type and at least one other of the two or more wells receives a different cell type; adding a test compound to the one or more wells receiving one cell type and adding the test compound to the one or more wells receiving a different cell type to provide at least two test compound wells that comprise cells of different types; providing at least two control wells that do not receive test compound, in which at least one of the wells receives cells of the one type and at least one of the control wells receives cells of the different type; monitoring cell-substrate impedance of the two or more test compound wells that comprise different cell types and the one or more control wells at at least three time points after adding the one or more test compounds; and analyzing impedance measurements from the two or more test compound wells comprising different cell types and from the one or more control wells at at least three time points after adding the one or more test compounds, in which changes in impedance can provide information about cell responses to the one or more test compounds.

In the methods of the present invention that investigate test compound effects on cells, impedance is preferably monitored from at least two test compound wells comprising different cell types at at least one time point before adding test compound to the at least one two compound wells. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

As disclosed in an earlier section on compound assays, a test compound can be any compound whose effect on cells can be investigated. A test compound used in assays comparing cell responses can be a compound whose effect on one or more of the cell types to be assayed is known, or can be a compound whose effects on any of the cell types to be assayed are unknown. In preferred methods of the present invention, cells are introduced into at least three wells of the device that each comprise an electrode array, and at least one well that comprises an electrode array and comprises cells does not receive a test compound. A control well that does not receive a test compound can be monitored, and its impedance data can be compared with that of wells that receive a compound to determine the effect of the test compounds on cells.

As disclosed in a previous section for compound assays, the cell types used in the assay can be primary cells isolated from any species or can be cells of cell lines. In some preferred embodiments, the different cell types are the same type of cell from different individuals, and thus have different genotypes. One or more of the cell types can be genetically engineered (For example, cells from a genetically modified organism, such as for example from a "gene knockout" organism, or cells that have been engineered to overexpress an endogenous gene or a transgene, or cells whose normal gene expression has been manipulated by use of antisense molecules or silencing RNA.) In these cases, genetically modified cells can be compared with control cells. In another example the cells can be, for example, stem cells from different stages of differentiation or of different genotypes whose response to growth factors is being compared. In other examples the cells can be cancer cells where the test compound is tested for its cytotoxic effects. The cells can be primary cancer cells of the same type isolated from different individuals, for example, or different cancer cell lines, or cancer cells of the same type but of different grades. In some embodiments, three or more different cell types are added to different wells and the behavior of the three or more different cell types in response to one or more compounds is compared. In preferred embodiments of the present invention, for each cell type tested there is a control performed in which the control does not receive test compound.

A variety of assays can be employed, where the effect of a test compound on the behavior of two or more cell types in the assay is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Preferably, time-dependent responses of the first and second types of cells are compared to see how similar or different the responses from the two types of cells are. In one method of the present invention, impedance from a first cell type well is plotted versus time to give a first cell type impedance curve and impedance from a second cell type well is plotted versus time to give a second cell type impedance curve. Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration of a cells response to a compound are similar or different. Preferably, impedance curves or cell index curves generated from control wells comprising each cell type in the absence of compound are compared with the test compound curves to assess the compound-specific effects on each cell type. The effects of the compounds on one or more of the two or more cell types can be effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect of a compound on at least one of the cell types used in the assay may be known. The mechanism of action of a compound on at least one of the cell types used in the assay may be known. In such cases, comparison of the compound response of one or more different cell types with the compound response of a cell type whose response to the compound is characterized can give information as to the similarity or difference in response of a different cell type to the compound.

In one preferred embodiment of this method, time-dependent cytotoxic responses of particular cell types to a compound are compared. Cytotoxicity assays can provide information on the sensitivity of one or more cell type to a compound.

Figure 9A:
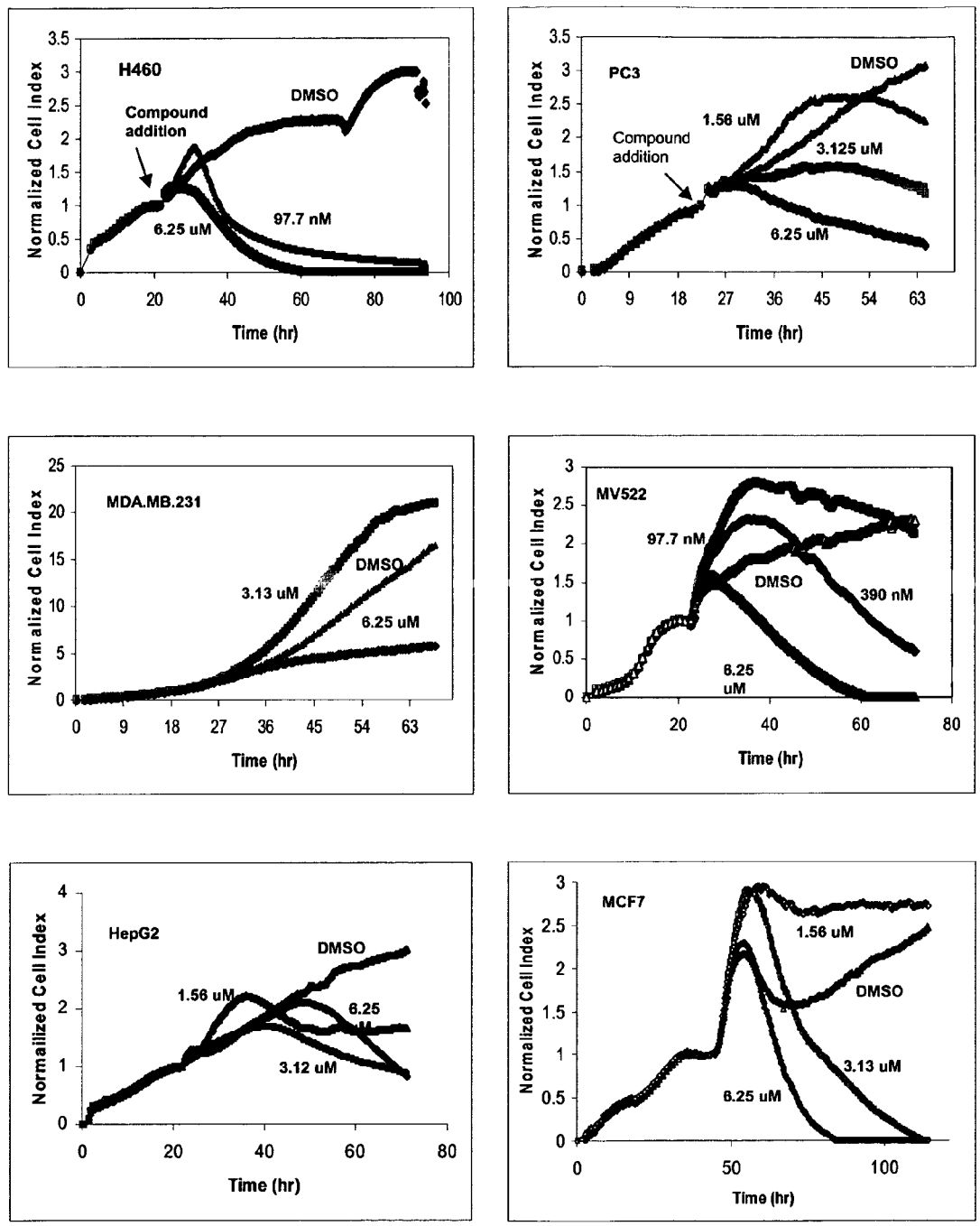
FIGS. 9A and B shows the responses of various cell types (listed in Table 1) to doxorubicin treatment as monitored using a cell-substrate impedance monitoring system of the present invention. The indicated cell lines were seeded onto microtiter devices fabricated with electronic sensor arrays shown in FIG. 1B. The cellular responses were continuously monitored at 15 or 30 or 60 minutes time interval before and after treatment with doxorubicin.
Figure 9B:
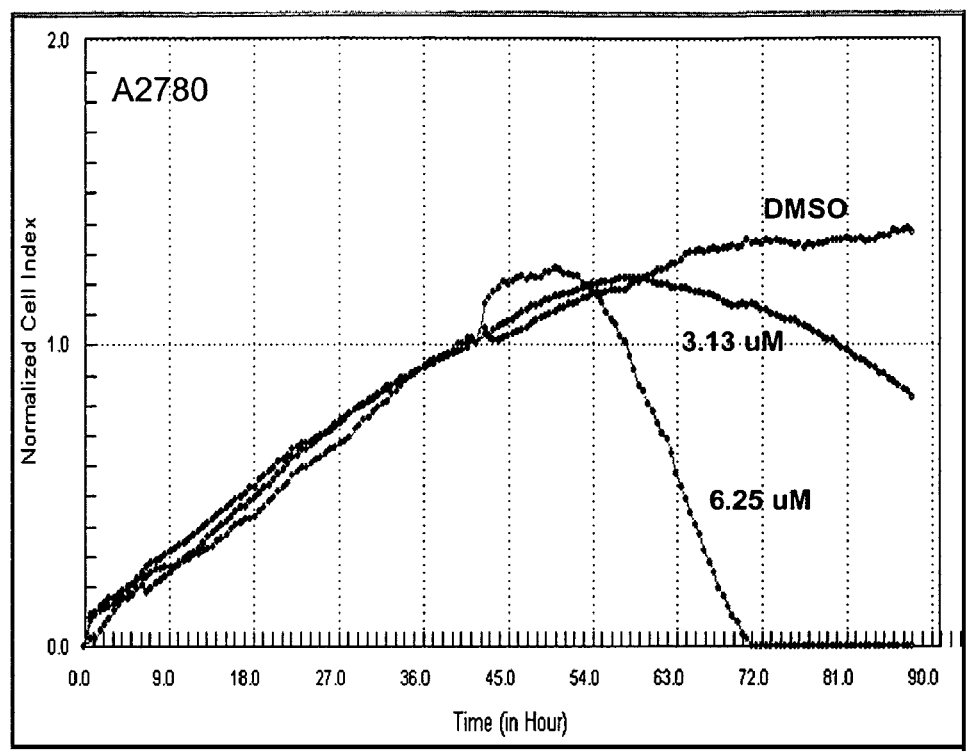
Figure 10A:
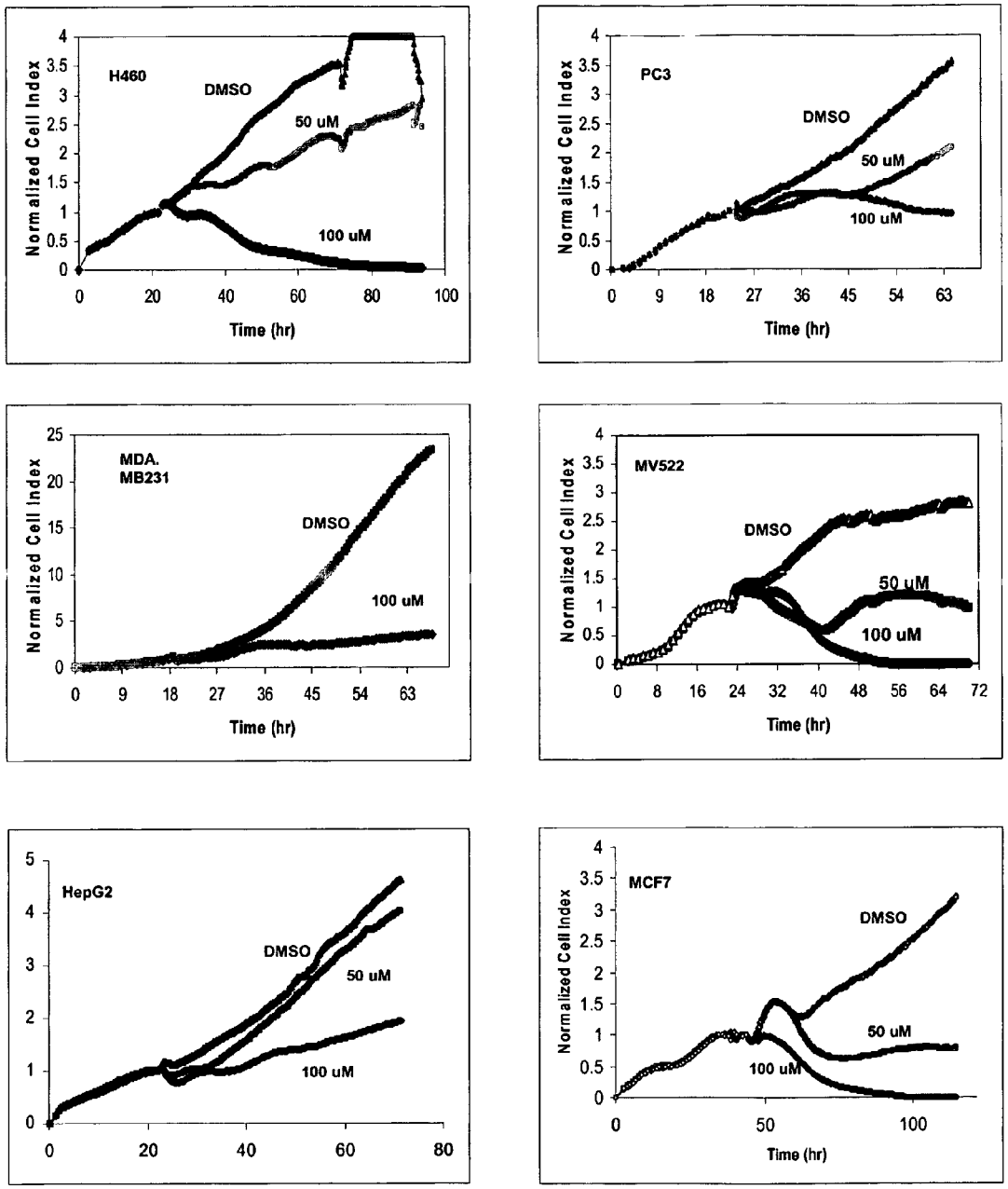
FIGS. 10A and B shows the responses of various cell types (listed in Table 1) to olomoucine treatment as monitored using a cell-substrate impedance monitoring system of the present invention. The indicated cell lines were seeded onto microtiter devices fabricated with electronic sensor arrays shown in FIG. 1B. The cellular responses were continuously monitored at 15 or 30 or 60 minutes time interval before and after treatment with olomoucine.
Figure 10B:
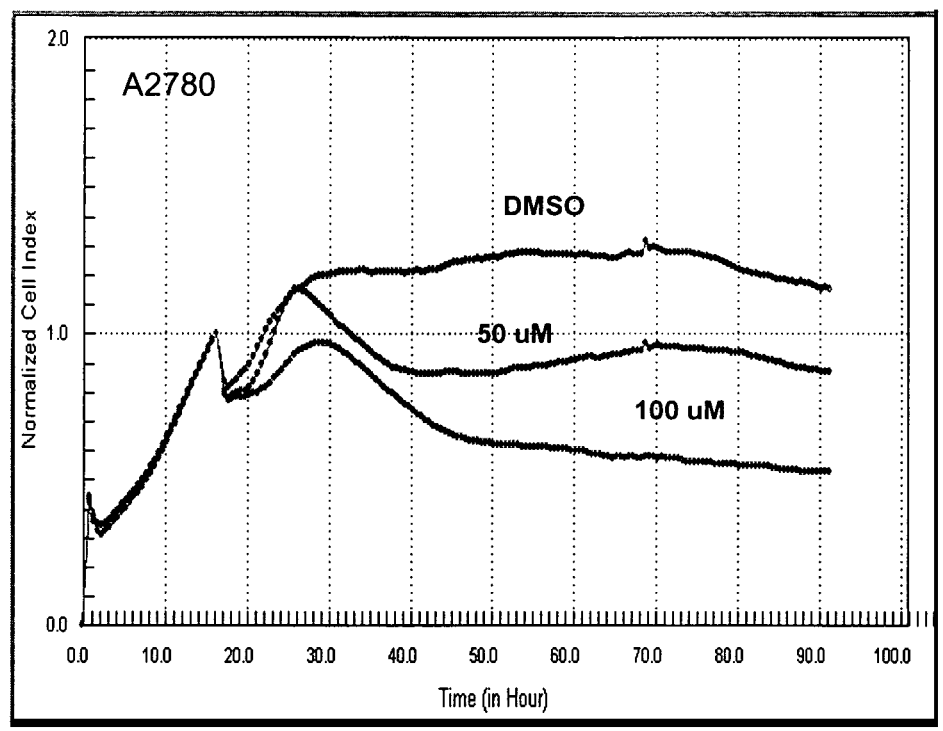

FIGS. 10A and B show the responses of various cell types (listed in Table 1) to olomoucine treatment as monitored using a cell-substrate impedance monitoring system of the present invention. The indicated cell lines were seeded onto microtiter devices fabricated with electronic sensor arrays shown in FIG. 1. The cellular responses were continuously monitored at 15 or 30 or 60 minutes time interval before and after treatment with olomoucine. Comparison among these cell index curves showed that certain similarity does exist. Take the treatment of olomoucine at 100 uM as an example. For a significant number of cell types tested, olomoucine treatment resulted in a near-constant cell index for some length of time (for example: 10, 20 or 30 hrs) a long time. This relates to the fact olomoucine is a cell cycle resting compound and for some time period following compound addition, cells do not divide any more and so cell number does not change but cells remain "live". Thus, for such time period, cell index did not change with time. The "near-constant" cell index curves were also observed for cells treated with roscovitine, which is another compound causing cell cycle arrest. The cell index curves shown in FIGS. 10A and 10B are strikingly different from the cell index curves shown in FIGS. 9A and 9B, and FIGS. 11A and 11B, where compounds follow different mechanism of compound action.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

Cell-Based Assays with More Than One Compound

The present invention also provides methods of comparing the effects of two or more different compounds on cells. In one aspect, the method comprises: providing a device of the present invention having three or more electrode arrays, each of which is associated with a fluid container of the device; attaching the device to an impedance analyzer; introducing cells into three or more fluid containers of the device that comprise an electrode array; adding at least one test compound to at least one of the three or more fluid containers comprising cells and adding at least one different test compound to at least one other of the three or more fluid containers comprising cells to provide at least two different test compound fluid containers; providing as a control fluid container at least one of the three or more fluid containers, in which the control fluid container receives cells but does not receive compound; attaching an impedance analyzer to the device; monitoring cell-substrate impedance of the two or more different test compound fluid containers that comprise different compounds and the one or more control fluid containers at at least three time points after adding the one or more test compounds; and analyzing impedance measurements from the two or more different test compound fluid containers and from the one or more control fluid containers at at least three time points after adding the one or more test compounds, in which changes in impedance can provide information about cell responses to the one or more test compounds.

In a related aspect, the present invention provides a method for performing a cell-based assay investigating the effect of two or more test compounds on cells using a cell-substrate impedance monitoring system. The method includes: a) providing a cell-substrate impedance monitoring system of the present invention; b) introducing cells into at least two wells of the device that each comprise an electrode array; c) adding to at least one well of the device comprising cells and an electrode array a first test compound; d) adding to at least one other well of the device comprising cells and an electrode array a second test compound; and e) monitoring cell-substrate impedance of at least one well comprising cells and a first compound and at least one well comprising cells and a second compound, in which changes in impedance can provide information about cell responses to the first and second compounds.

Preferably, time-dependent responses of cells to the first compound and the second compound are compared to see how similar or different the responses from the two compounds are. In one preferred embodiment of this method, time-dependent cytotoxic responses are compared.

The cells and test compound that can be used in the assay can be any as described above for assays testing effects of test compounds.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Impedance monitoring can be as described above for assays testing effects of test compounds. Preferably impedance is monitored from the at least two different test compound wells and at least one control well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

Preferably, data from impedance monitoring of wells that comprise different test compounds are compared.

In one embodiment, for at least two different compound wells, impedance at three or more assay time points can be plotted versus time. Preferably, for a control well that does not receive compound, impedance at the same three or more assay time points is also plotted versus time. The impedance curves of different compound wells can be compared with the control impedance curve to determine whether the compounds have a similar or different effect on cells.

Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration the response of cells to different compounds are similar or different. Preferably, impedance curves or cell index curves generated from one or more control wells comprising cells in the absence of compound are compared with the test compound curves to assess the compound-specific effects of each compound. The effects of the compounds on cells can be for example, effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect on cells of one or more of the compounds used in the assay may be known. The mechanism of action of one or more compounds used in the assay may be known. In such cases, comparison of the responses of cells to other test compounds used in the assay with cellular responses to the one or more compounds whose effects are characterized can give information as to the similarity or difference in response of different compounds to a known compound.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

A plurality of compounds can be assayed with multiple cell types. In one preferred embodiment of this method, time-dependent cytotoxic responses of different cell types to a set of compounds are compared.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

For example, the time frame, magnitude, and duration of a difference in response as evidenced by the curves can indicate a difference in efficacy or mechanism of compounds. The impedance differences can reflect differences in, for example, cell attachment or adhesion, cell growth or proliferation; the number of viable cells or dead cells; cytoskeleton organization or function; or the number of cells going through apoptosis or necrosis in response to a test compound.

A variety of assays can be employed, where the effect of two or more test compound on the behavior cells is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In one preferred embodiment of this method, time-dependent cytotoxic responses of cells to a set of compounds are compared. "Cytotoxicity profiling" in which the impedance responses of cells in response to a plurality of potentially cytotoxic compounds are compared, can provide information on the efficacy and mechanism of a test compound. Cytotoxicity profiling can be performed by comparing any combination of impedance plots, kinetic parameters derived from impedance plots, CI plots, CCI values, and CCI plots.

In one embodiment of the method, analyzing the cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Evaluating the Effect of Different Concentrations of a Compound on Cells

The present invention also includes methods of performing assays to test the effect of different concentrations of one or more test compounds on cells.

In one aspect, a method for testing different concentrations of a test compound on cells comprises: providing a device of the present invention having three or more electrode arrays, each of which is associated with a fluid container of the device; attaching the device to an impedance analyzer; introducing cells into at least two of the three or more fluid containers of the device that comprise an electrode array; adding different concentrations of a test compound to the two or more fluid containers of the device that comprise cells; providing a control fluid container that comprises cells but does not receive compound; monitoring cell-substrate impedance of the two or more different test compound fluid containers that comprise different concentrations of a test compound and of the one or more control fluid containers at at least three time points after adding a test compound; and analyzing impedance measurements from the two or more different test compound fluid containers and one or more control fluid containers at at least three time points after adding a test compound, in which changes in impedance can provide information about cell responses to the test compounds.

In a related aspect, the present invention provides a method for performing a cell-based assay investigating the effect of two or more concentrations of a test compound on cells using a cell-substrate impedance monitoring system. The method includes: providing a cell-substrate impedance monitoring system of the present invention; introducing cells into at least two of the three or more wells of the device that comprise an electrode array; adding different concentrations of a test compound to the two or more wells of the device that comprise cells; providing a control well that comprises cells but does not receive test compound; monitoring cell-substrate impedance of the two or more different test compound wells that comprise different concentrations of a test compound and the one or more control wells at at least three time points after adding a test compound; and analyzing impedance measurements from the two or more different test compound wells and the one or more control wells at at least three time points after adding a test compound, in which changes in impedance can provide information about cell responses to the test compounds.

The cells and test compound that can be used in the assay can be any as described above for assays testing effects of test compounds.

Impedance monitoring can be as described above for assays testing effects of test compounds. Preferably impedance is monitored from the at least two different test compound wells and at least one control well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurements taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

In one embodiment, for at least two different compound concentrations, impedance or, preferably, cell index (including normalized cell index or delta cell index), at three or more assay time points is be plotted versus time. Preferably, for a control well that does not receive compound, impedance at the same three or more assay time points is also plotted versus time. An impedance curve or cell index curve can give an indication of the time frame at which a compound affects cell response. In some preferred embodiments, the cell index can be used as an indicator of cytotoxicity.

FIGS. 9A and B shows the responses of various cell types (listed in Table 1) to doxorubicin treatment as monitored using a cell-substrate impedance monitoring system of the present invention. The indicated cell lines were seeded onto microtiter devices fabricated with electronic sensor arrays shown in FIG. 1. The cellular responses were continuously monitored at 15 or 30 or 60 minutes time interval before and after treatment with doxorubicin. Comparison among these cell index curves showed that certain similarity does exist. Take the treatment of doxoorubincin at 3.13 uM as an example. For most of cell types tested, initially after the treatment, cell index increased with time in similar way to the cell index from DMSO control wells. After 10-20 hrs, depending on cell type, the cell index reached a peak and started decreasing with time. From that time on, the cell index monotonically decreases. Such cell index curves—characterized by "going up first and then going down"-were also observed for the cells treated with 5-Fluorouracil. Both Doxorubicin and 5-Fluorouracil act on cells through effects on DNA replication or topology.

Figure 9B:
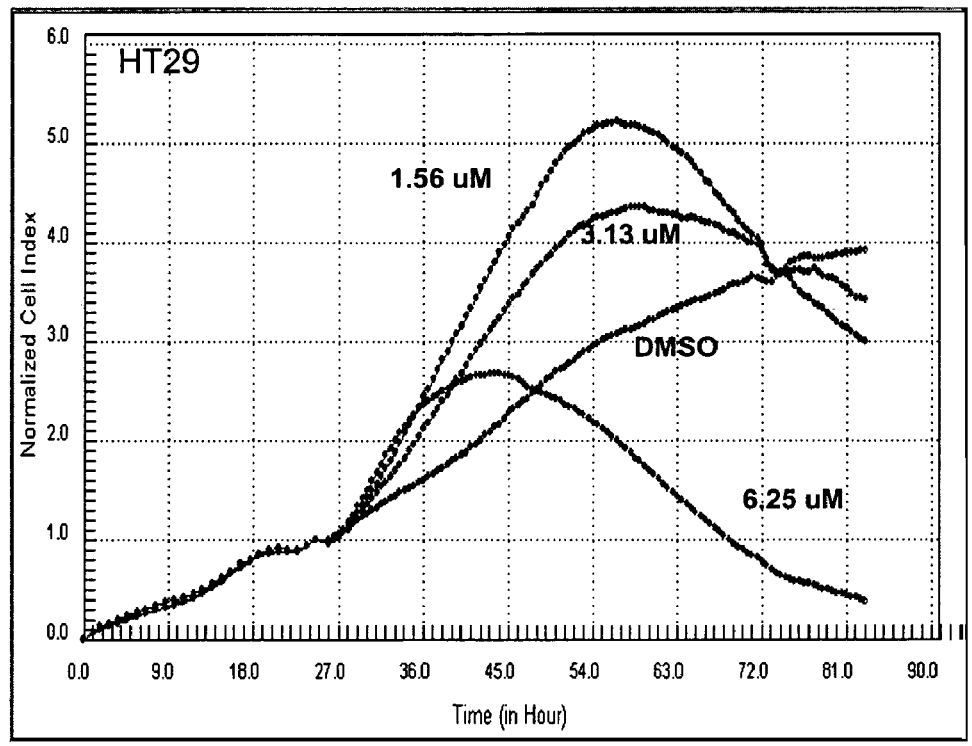

Furthermore, such cell index curves are strikingly different from the cell index curves shown in FIGS. 10A and 10B, where 100 uM of olomoucine resulted in a nearly constant cell index value for 10, 20 even 30 hrs after compound addition. The cell index curves shown in FIG. 9 are also strikingly different from the cell index curves in FIG. 11, where nM concentration of paclitaxel caused an initial cell index decrease for about 15 hrs (it varies between cell types) and then a cell index increase. These dynamic changes in cell index curves reflect the fact that these different compounds interacts with the cells differently. Compounds that interact with cells in similar way or following same mechanism would result in a similar cell index response curves. One application of this is to investigate the mechanism of compound action based on the observed cell index curves. If cell index responses follow a certain pattern, then one may be able to deduce the mechanism of compound action. Alternatively, if two compounds showed similar, dynamic cell index response curves, then these two compounds may act on the cells with similar or same mechanism of compound action.

Figure 11A:
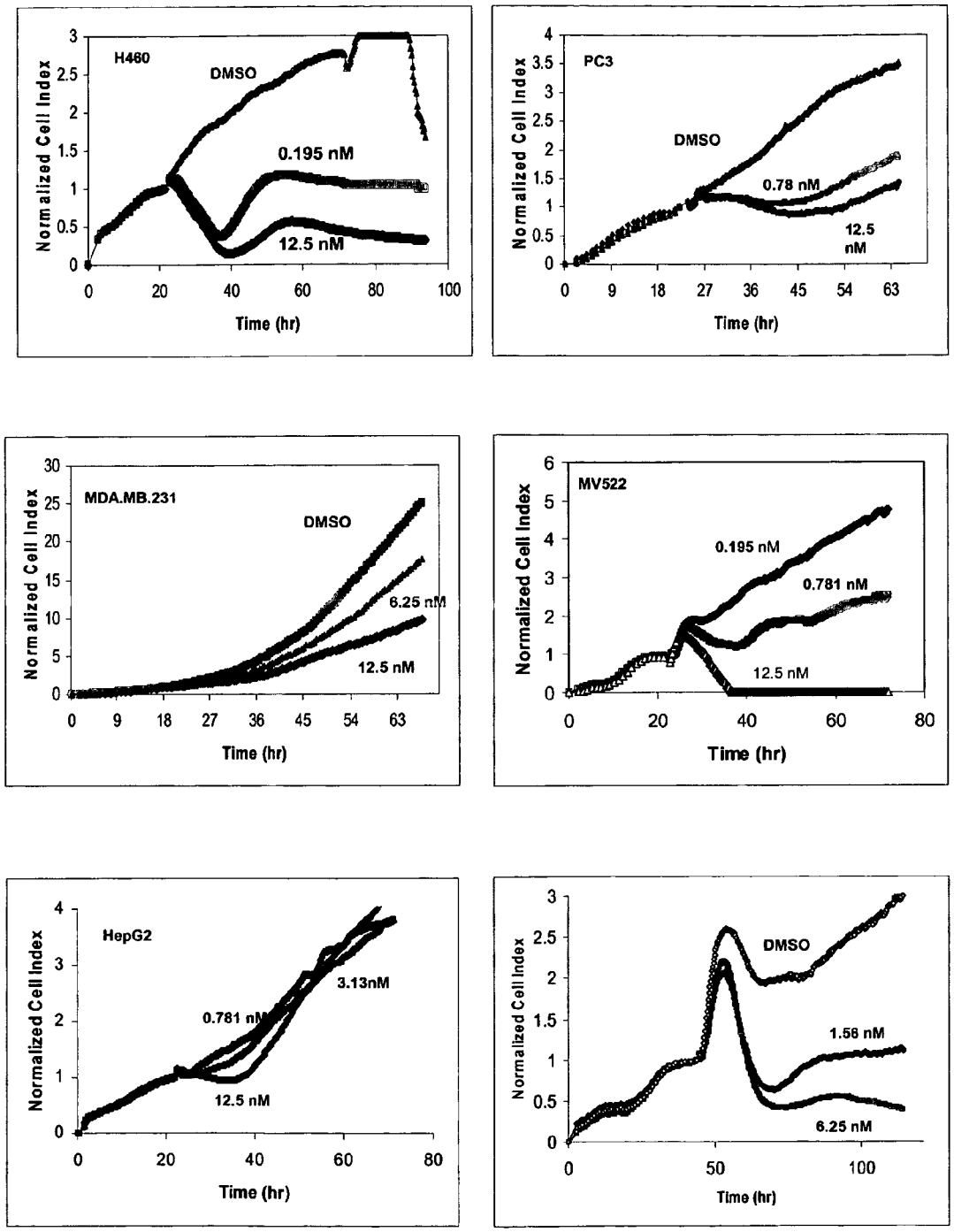
FIGS. 11A and 11B show the responses of various cell types (listed in Table 1) to paclitaxel treatment as monitored using a cell-substrate impedance monitoring system of the present invention. The indicated cell lines were seeded onto microtiter devices fabricated with electronic sensor arrays shown in FIG. 1B. The cellular responses were continuously monitored at 15 or 30 or 60 minutes time interval before and after treatment with paclitaxel.
Figure 11B:
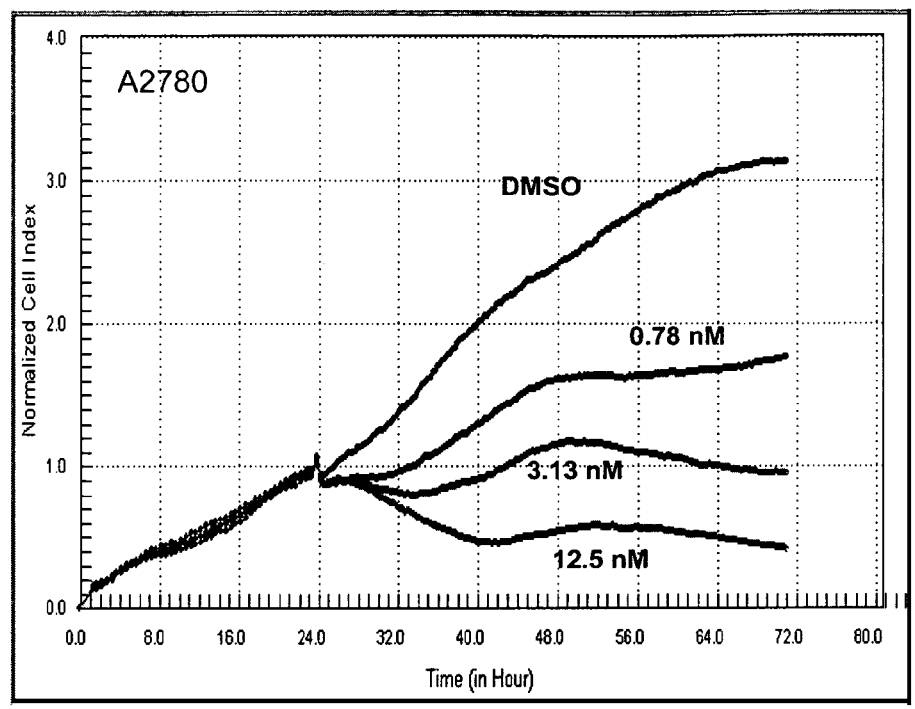
Figure 11B:
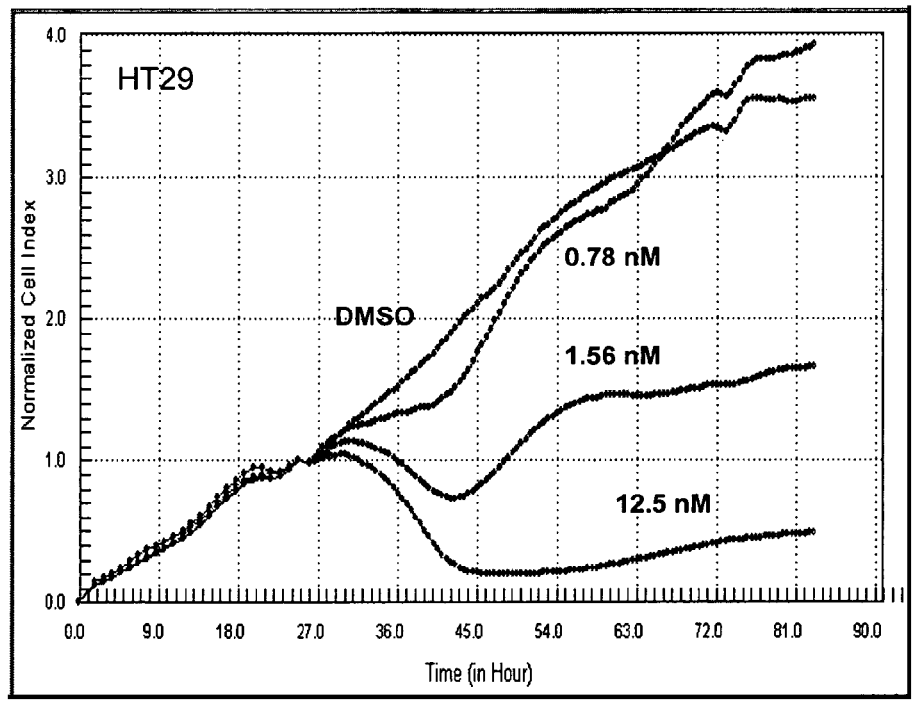
Figure 16A:
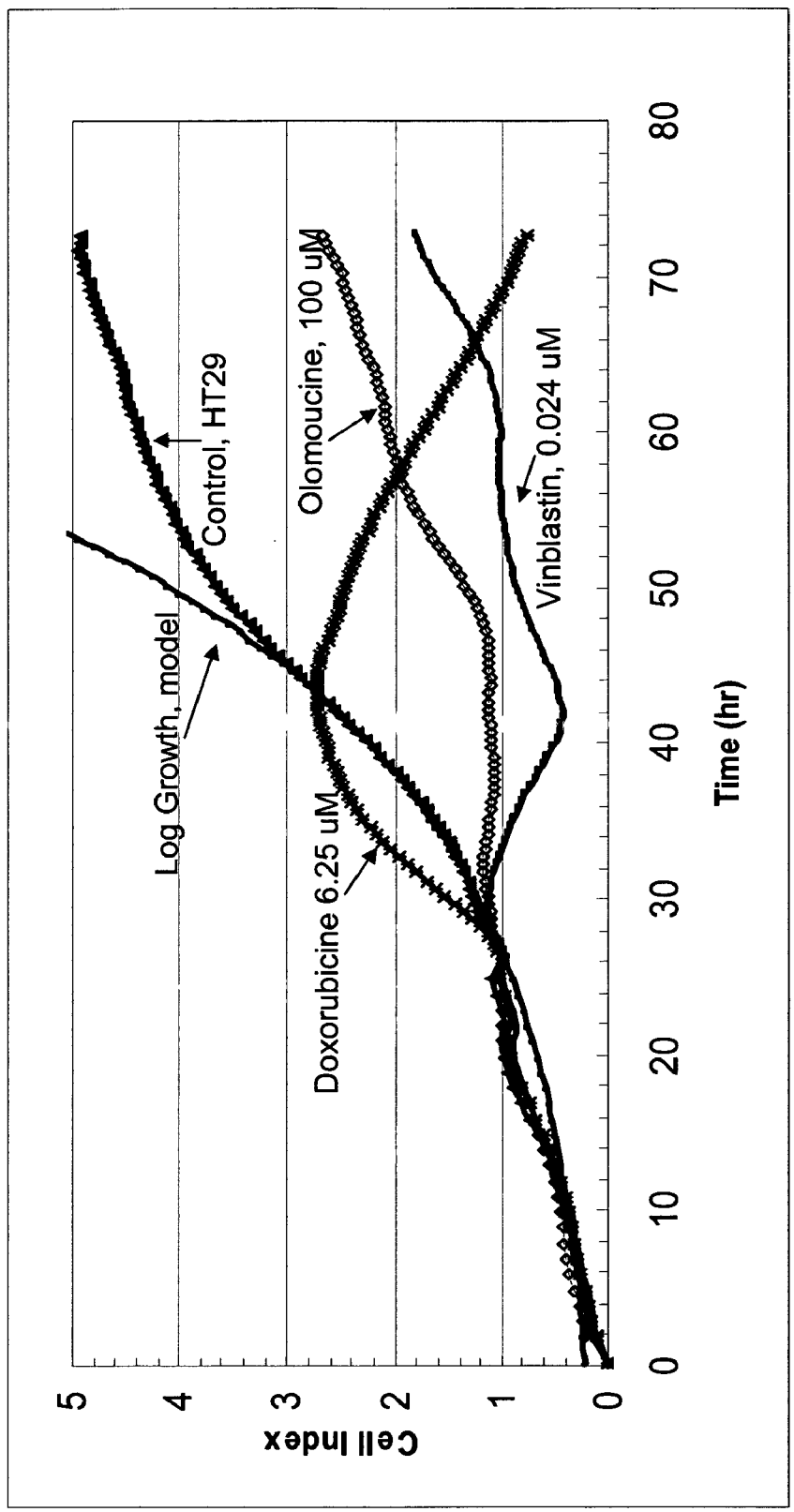
FIG. 16A shows the cell index curves of HT29 cells before and after treatment with various compounds. Also shown is an theoretical exponential increase of cell index with time (labeled as "Log-growth, model") and cells treated with DMSO vehicle control (labeled as "Control, HT29").
Figure 22:
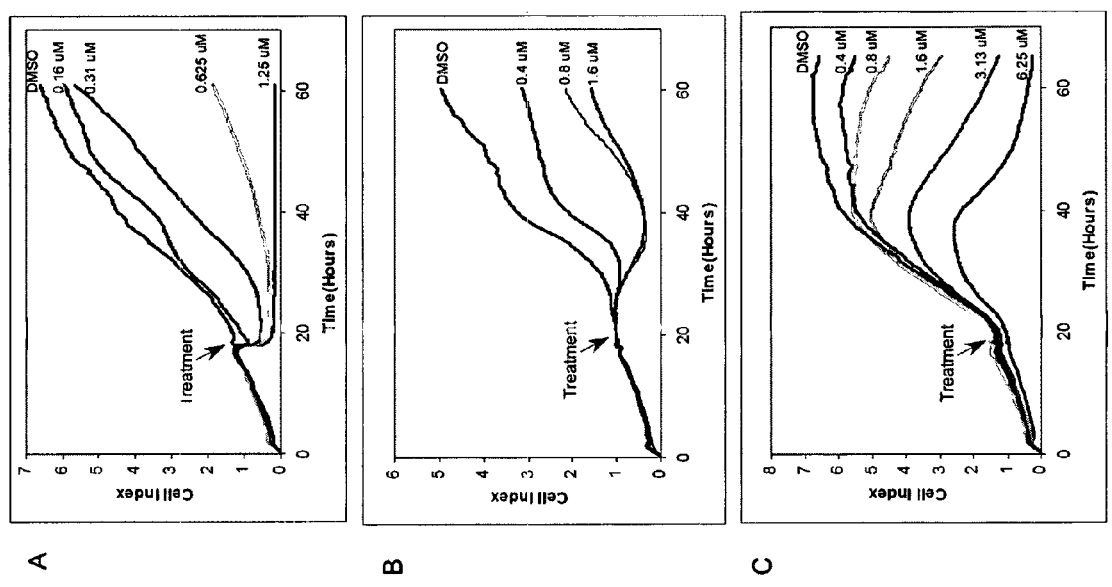
FIG. 22. Dynamic monitoring of cytotoxic compounds with target cells using a cell-substrate impedance monitoring system of the present invention. A549 cells were seeded in a device of the present invention and continuously monitored using the RT-CES system. The cells were treated with the indicated final concentrations of (A) staurosporine, (B) vinblastine and (C) 5-fluorouracil.

FIGS. 11A and 11B shows the responses of various cell types (listed in Table 1) to paclitaxel treatment as monitored using a cell-substrate impedance monitoring system of the present invention. The indicated cell lines were seeded onto microtiter devices fabricated with electronic sensor arrays shown in FIG. 1. The cellular responses were continuously monitored at 15 or 30 or 60 minutes time interval before and after treatment with paclitaxel. Comparison among these cell index curves showed that certain similarity does exist. Take the treatment of paclitaxel at 0.78-12.5 nM range as examples. Typically, such nM paclitaxel treatment resulted in an initial decrease in cell index for about 15-20 hrs. For one particular cell index curve, after the cell index reached a minimum, it then reversed its decreasing trend and started to increase. Such "going down and then going up" feature in cell index curves was also observed in cell index curves for cells treated with vinblastin or colcemid. Examples of cell index curve for vinblastin-treated cells are shown in FIG. 16A and FIG. 22. All these compounds—i.e., paclitaxel, vinblastin and colcemid, are so called mitotic poisons and follow similar mechanism of drug action. For example, both vinblastin and paclitaxel act on microtubule dynamics within a cell.

In addition, for a given assay time point, cell index (including normalized cell index or delta cell index), can be plotted versus compound concentration. Such dose response relationships can be used to derive a time-dependent IC5, IC10, IC20, IC30, IC40, IC50, IC60, IC70, IC80, IC90, or IC95. In some preferred embodiments, a time-dependent IC50 is calculated for a compound. Determining a range of time-dependent IC50s for a compound provides information on when the effect of the compound on cells is maximal.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

For example, the time frame, magnitude, and duration of a difference in response as evidenced by the curves can indicate a difference in efficacy or mechanism of compounds. The impedance differences can reflect differences in, for example, cell attachment or adhesion, cell growth or proliferation; the number of viable cells or dead cells; cytoskeleton organization or function; or the number of cells going through apoptosis or necrosis in response to a test compound.

Preferably, data from impedance monitoring of wells that comprise different cell types are compared. In one preferred embodiment impedance monitoring is performed for different cell types exposed to multiple dose concentrations of a compound. In some embodiments, multiple compounds can be tested with multiple cell types. In some embodiments, multiple compounds at multiple concentrations can be tested with multiple cell types.

Cytotoxicity Profiling

In another aspect, the present invention provides a method for performing real-time cytotoxicity assay of a compound, comprising: a) providing an above described system; b) seeding cells to the wells of multiple-well devices; c) adding the compound to the wells containing cells; d) monitoring cell-substrate impedance before and after adding the compound at a regular or irregular time interval; wherein the time dependent impedance change provides information about time dependent cytotoxicity of the compound. In one embodiment, the cell-substrate impedance is monitored at regular time intervals. In exemplary embodiments, the impedance is measured at a regular 2 hour, 1 hour, 30 min or 15 min time interval before and after adding the compound.

In one embodiment of the above method, multiple wells with same cell types are used, wherein each well is added with the compound of different concentrations. The method provides the time-dependent and concentration-dependent cytotoxic responses.

In yet another aspect, the present invention provides a method for analyzing and comparing time-dependent cytotoxic effects of a first compound and a second compound on a cell type, comprising: a) performing a real-time cytotoxicity assay on a cell type with the first compound using the method described above; b) performing a real-time cytotoxicity assay on said cell type with the second compound using the method described above; c) comparing the time-dependent cytotoxic responses of the first compound and the second compound to see how similar or different the responses from the two compounds are. In one embodiment of this method, time-dependent cytotoxic responses are determined for the first compound at multiple dose concentrations. In another embodiment, time-dependent cytotoxic responses are determined for the second compound at multiple dose concentrations. In yet another embodiment, time-dependent cytotoxic responses are determined for both first compound and second compound at multiple dose concentrations.

In another embodiment of above methods, the first compound is a compound with a known mechanism for its cytotoxic effect and the second compound is a compound with an unknown mechanism for its cytotoxic effect. If the time dependent cytotoxic responses from the second compound are similar to that of the first one, the second compound may follow a similar mechanism for its cytotoxic effect to the first compound.

Various approaches may be used in comparing the cytotoxic responses of the compounds. A cell index (or cell number index) can optionally be calculated using the impedance values obtained. In one embodiment of the method described above, time dependent IC50 may be derived for the compounds and comparison between their cytotoxic responses is done by comparing their time dependent IC50 curves based on cell index values. If the IC50 curves follow a similar time-dependent trend, the two compounds may follow a similar mechanism for inducing cytotoxicty effects. In another embodiment of the method described, direct comparison of time-dependent cytotoxic responses of two compounds are done where the concentrations for the two compounds may be the same or may be different. Direct comparison between time-dependent cytotoxic responses may be done by analyzing the slope of change in the measured responses (that is equivalent to the first order derivative of the response with respect to time) and comparing the time-dependent slopes for the two compounds. In another approach, the time-dependent cytotoxic responses may be analyzed for their higher order derivatives with respect to time. Comparing such high order derivatives may provide additional information as for the mechanisms of compound-induced cytotoxicity.

In one embodiment of the method, analyzing real-time cytotoxicity response may include the derivation of time-dependent IC50 values for the compound on the multiple cell types. In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

In yet another embodiment, the above methods are applied to perform cytotoxicity profiling of multiple compounds on multiple cell types.

In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Some examples of compound assays that can be performed using a cell-substrate impedance system of the present invention are provided by way of illustration with reference to the figures. In these examples, cell index is calculated using the same method as the Cell Index calculation method (A) as described in Section C of the present application. In some of the figures of the present application, Normalized Cell Index was plotted. The Normalized Cell Index at a given time point is calculated by dividing the Cell Index at the time point by the Cell Index at a reference time point. Thus, the Normalized Cell Index is 1 at the reference time point.

As described in the present application, if the cell attachment conditions remain unchanged or exhibit little change over the course of an assay that uses impedance monitoring, then the larger the cell index, the larger the number of the cells in the wells. A decrease in cell index suggests that some cells are detaching from the substrate surface or dying under the influence of the compound. An increase in cell index suggests that more cells are attaching to the substrate surfaces, indicating an increase in overall cell number.

Figure 5:
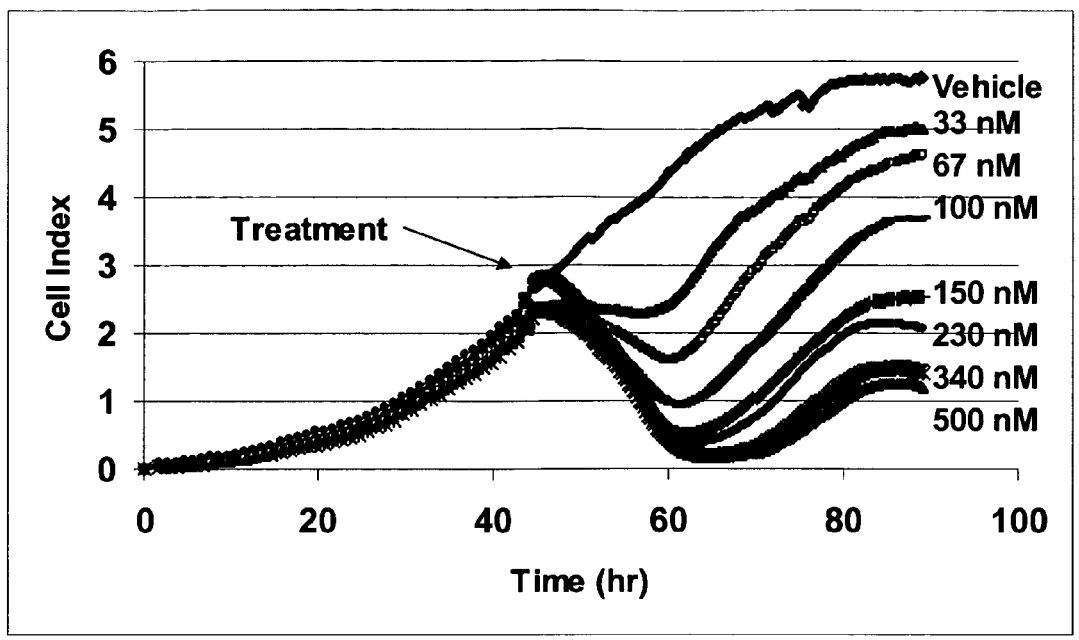
FIG. 5 shows time-dependent cell index for H460 cells treated by anticancer drug paclitaxel. Different wells of cultured H460 cells were treated at their exponential growth phase with different concentrations of Paclitaxel. The dynamic response of the cells to different doses of paclitaxel was monitored in real time every 15 minutes for 50 hours after treatment using a cell-substrate impedance monitoring system of the present invention. For paclitaxel concentration between 67 nM and 500 nM, H460 cells exhibited a gradual decrease in cell index initially after the compound addition. However, the cell index reached a minimum at a time dependent on the compound concentration between about 15 hours and 20 hours after compound addition. After that point, the cell index exhibited a gradual increase in cell index. The cell index for compound concentration of 33 nM exhibited a near-constant value for time up to about 15 hours after compound addition. After 15 hours following the compound addition, the cell index exhibited a gradual increase in cell index.

FIG. 5 shows curves that represent the time-dependent cell index for H460 cells treated with different concentrations of the anticancer drug paclitaxel. In this experiment, H460 cells were introduced into wells of a 16× cell-substrate impedance monitoring device. The device was positioned on a device station that was located in an incubator maintaining conditions of 37 degrees C. and 5% $CO_2$. The cells were cultured and treated at their exponential growth phase with different concentrations of paclitaxel. The dynamic response of the cells to different doses of paclitaxel was monitored by monitoring cell-substrate impedance in real time every 15 minutes for 50 hours after treatment using a cell-substrate impedance monitoring system. The cell-substrate impedance monitoring system calculated the cell index at each time point monitored and plotted the cell index as a function of time. For paclitaxel concentrations between 67 nanomolar and 500 nanomolar, H460 cells exhibited a gradual decrease in cell index after compound addition. However, the cell index reached a minimum at a time dependent on the compound concentration, between about 15 hours and 20 hours after compound addition. After that point, there was a gradual increase in cell index in these wells. The cell index for compound concentration of 33 nanomolar exhibited a near-constant value for up to about 15 hours after compound addition. After 15 hours following compound addition, the cell index exhibited a gradual increase.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

Figure 6:
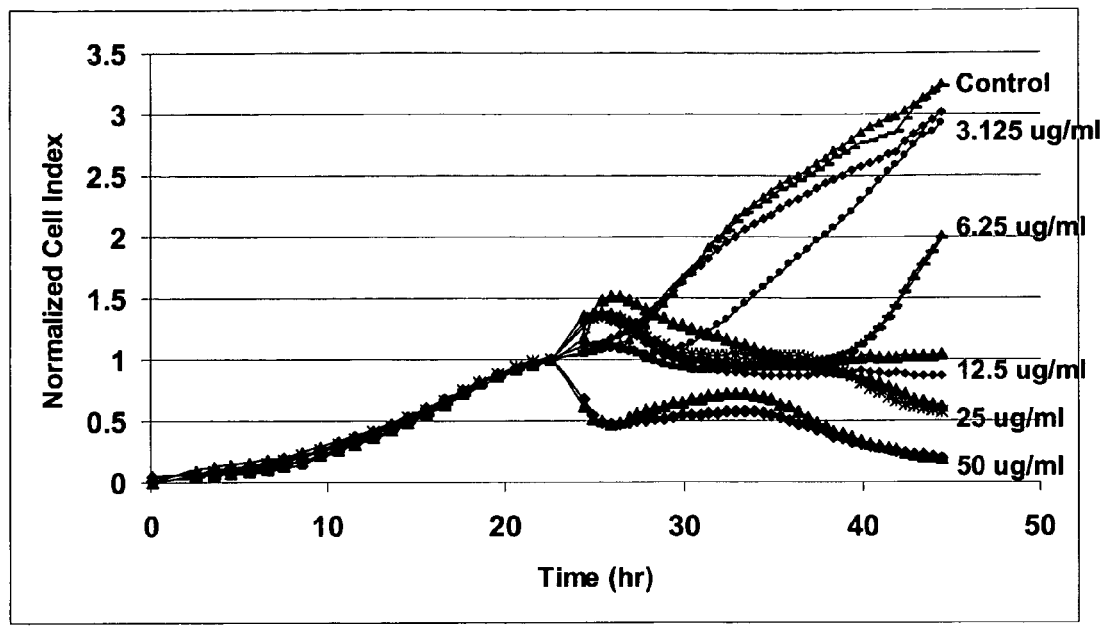
FIG. 6 shows time-dependent cell index for H460 cells treated by anticancer drug AC101103. Different wells of cultured H460 cells were treated at their exponential growth phase with different concentrations of AC101103. The dynamic response of the cells to different doses of AC101103 was monitored in real time every 30 minutes for about 20 hours on a cell substrate impedance monitoring system of the present invention. The time-dependent cell index in FIG. 6 is significantly different from those shown in FIG. 5. For compound concentrations at 3.125 ug/ml, 6.25 ug/ml and 12.5 ug/ml, the cell index exhibited a near-constant value for about 5 hrs, about 15 hrs and >20 hrs respectively. For compound concentrations at 3.125 ug/ml and 6.25 ug/ml, the cell index started to increase after about 5 hrs and about 15 hrs following compound addition. For the compound concentration of 25 ug/ml, there was a gradual, yet slow decrease in the cell index after compound addition. For the compound concentration of 50 ug/ml, there was an about 10 hr time period over which the cell index remained near-constant, and after that, the cell index decreased steadily.

FIG. 6 shows curves that represent the time-dependent cell index for H460 cells treated with anticancer drug AC101103. H460 cells were introduced into wells of a 16× cell-substrate impedance monitoring device. The device was positioned on a device station that was located in an incubator maintaining conditions of 37 degrees C. and 5% $CO_2$. The cells were cultured and treated at their exponential growth phase with different concentrations of AC101103. The dynamic response of the cells to different doses of AC101103 was monitored by measuring impedance in real time every 30 minutes for about 20 hours after treatment on the cell-substrate monitoring system.

Notably, the time-dependent cell index in FIG. 6 is significantly different from those shown in FIG. 5. For compound concentrations at 3.125 microgram/ml, 6.25 microgram/ml and 12.5 microgram/ml, the cell index exhibited a near-constant value for about 5 hrs, about 15 hrs and >20 hrs respectively. For compound concentrations at 3.125 microgram/ml and 6.25 microgram/ml, the cell index started to increase after about 5 hrs and about 15 hrs following compound addition. For the compound concentration of 25 microgram/ml, there was a gradual, yet slow decrease in the cell index after compound addition. For the compound concentration of 50 microgram/ml, there was an about 10 hr time period over which the cell index remained near-constant, and after that, the cell index decreased steadily.

Figure 7:
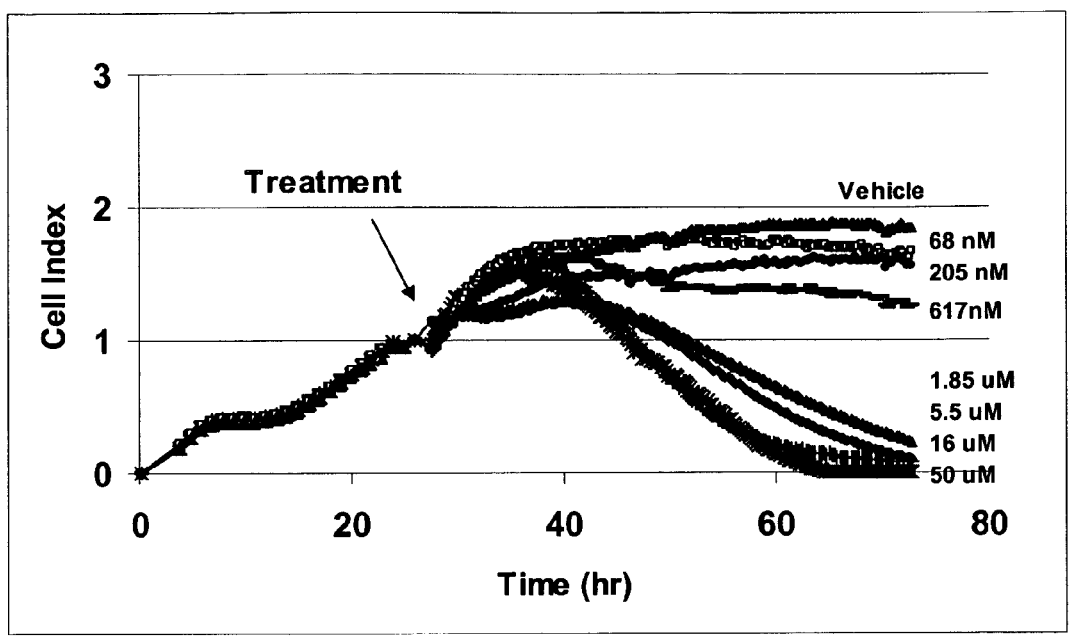
FIG. 7 shows dynamic drug response curves of A549 cells treated with doxorubicin. 10,000 A549 cells were seeded in each well of a 16× device. The cell attachment and cell growth were monitored on the cell-substrate impedance monitoring system of the present invention in real time before treatment. When the cells were in exponential growth phase, doxorubicin at different concentration was added to the cells. Same volume of a solvent used for dissolve the drug was served as vehicle control. The time, and drug dose dependent cell response to doxorubicin was recorded in real time.

FIG. 7 shows dynamic drug response curves of A549 cells treated with doxorubicin. 10,000 A549 cells were seeded into each well of a 16× device. The device was positioned on a device station that was located in an incubator maintaining conditions of 37 degrees C. and 5% $CO_2$. Cell attachment and cell growth were monitored on a cell-substrate impedance system in real time before treatment by monitoring impedance at regular intervals. When the cells were in exponential growth phase, doxorubicin at different concentrations was added to the wells. The same volume of the solvent used to dissolve the drug was added to some wells as a control. The time, and drug dose dependent cell response (calculated as cell index) to doxorubicin was recorded in real time on the cell-substrate impedance monitoring system as shown in this figure.

EXAMPLE 1

Figure 10B:
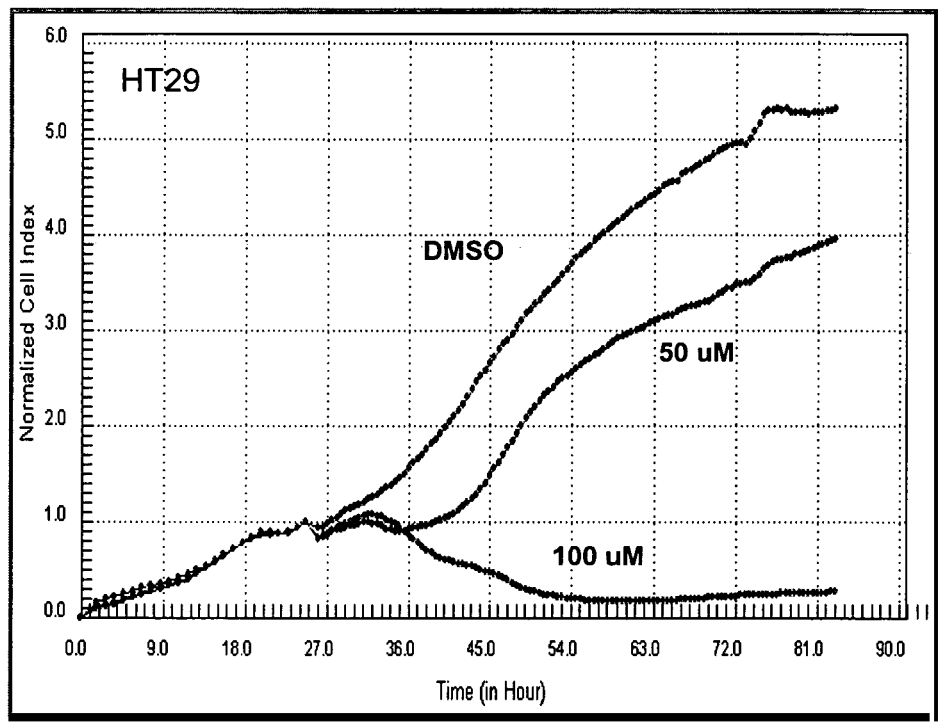
Figure 12A:
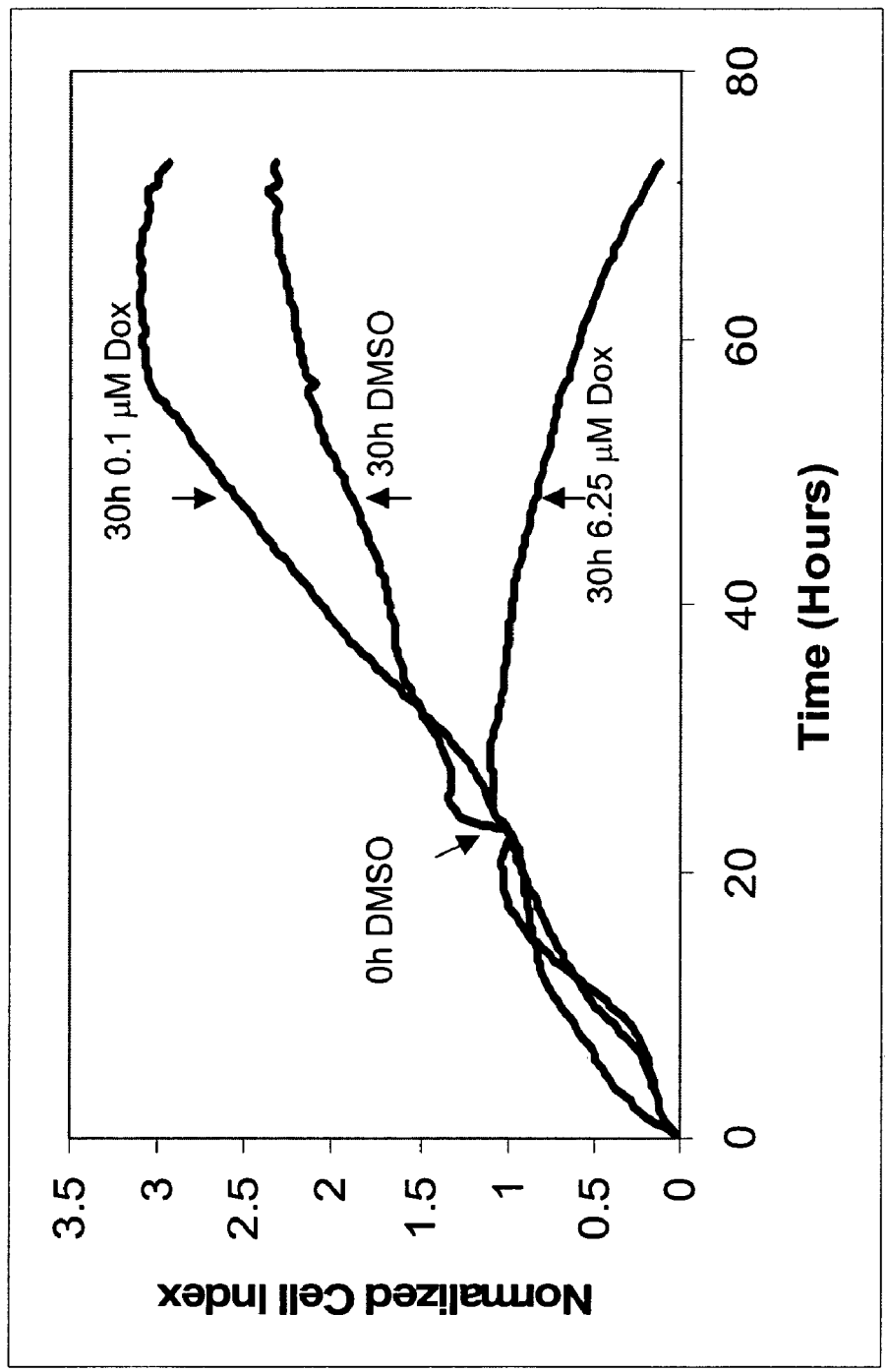
FIG. 12A shows the response of MV522 cells to doxorubicin treatment as monitored using a cell-substrate impedance monitoring system of the present invention. MV522 cells were seeded onto microtiter devices fabricated with electronic sensor arrays shown in FIG. 1B and were treated with either DMSO or doxorubicin at the indicated time and concentration.
Figure 13A:
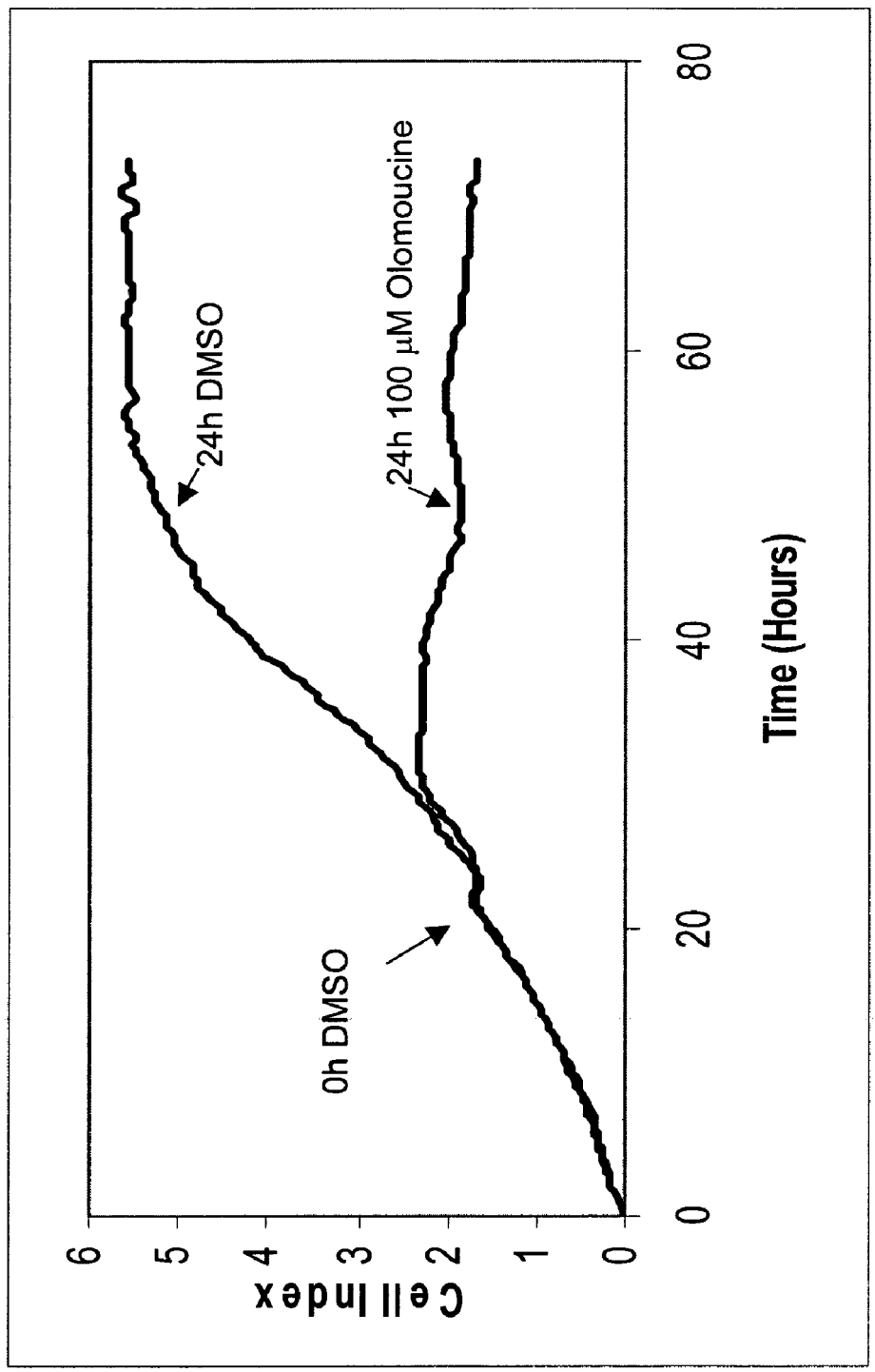
FIG. 13A shows the response of A549 cells to olomoucine treatment as monitored using a cell-substrate impedance monitoring system of the present invention. A549 cells were seeded onto microtiter devices fabricated with electronic sensor arrays shown in FIG. 1B and were treated with either DMSO or olomoucine at the indicated time and concentration.
Figure 13B:
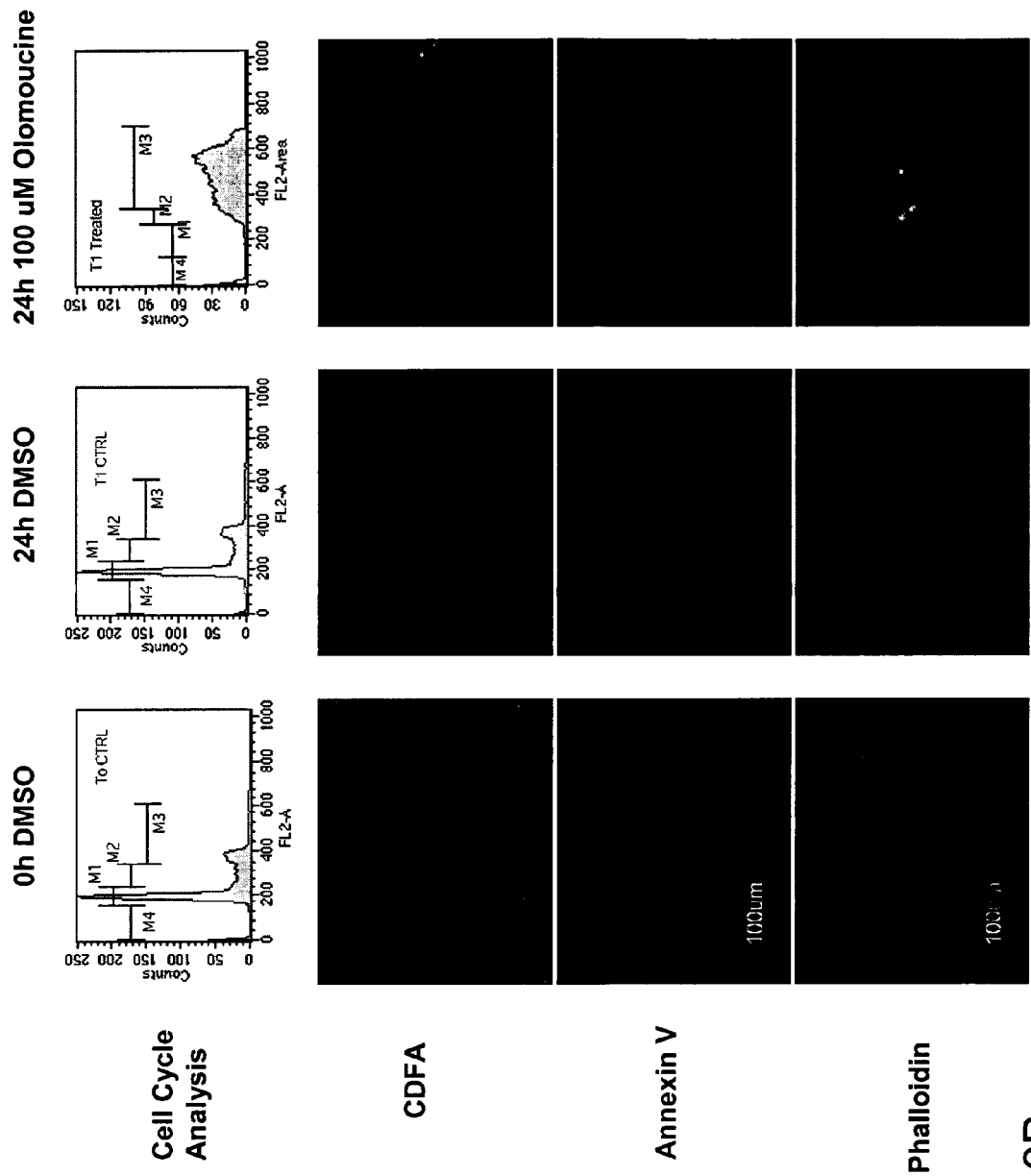
FIG. 13B shows the characterization of the cell biological effect of olomoucine treatment on MV522 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 14A:
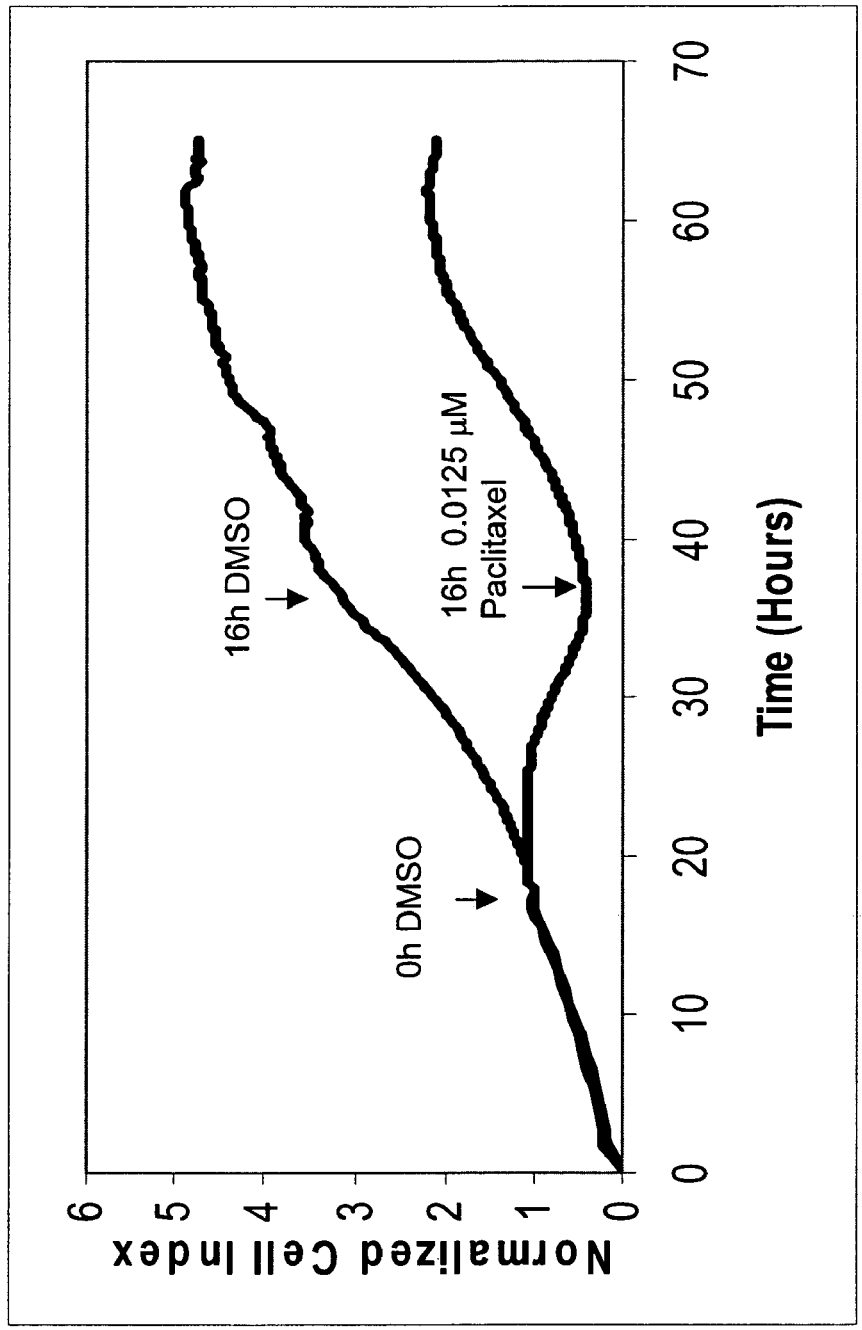
FIG. 14A shows the response of A549 cells to paclitaxel treatment as monitored using a cell-substrate impedance monitoring system of the present invention. A549 cells were seeded onto microtiter devices fabricated with electronic sensor arrays shown in FIG. 1B and were treated with either DMSO or paclitaxel at the indicated time and concentration.
Figure 14:
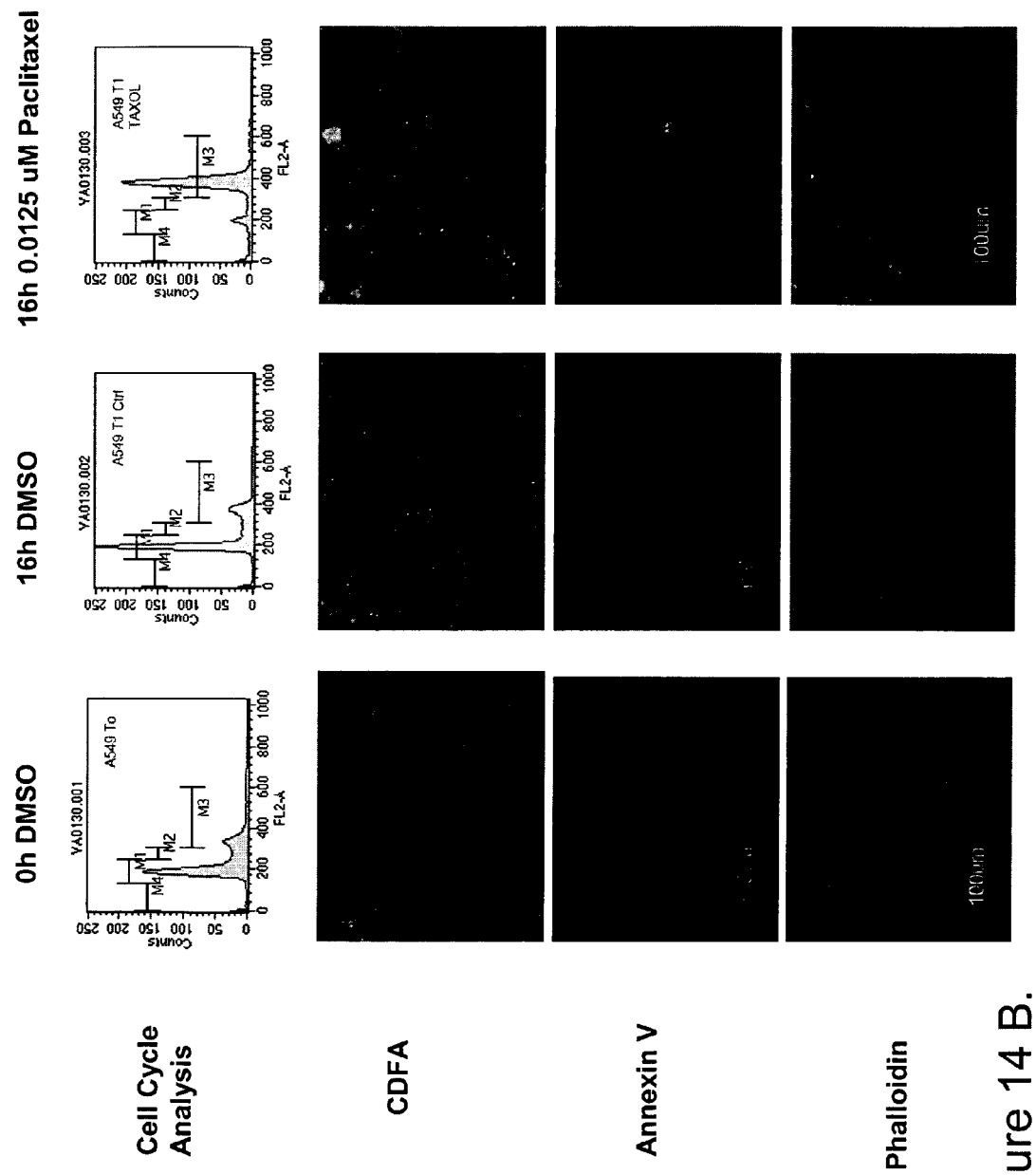
FIG. 14B shows the characterization of the cell biological effect of paclitaxel n treatment on A549 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 15A:
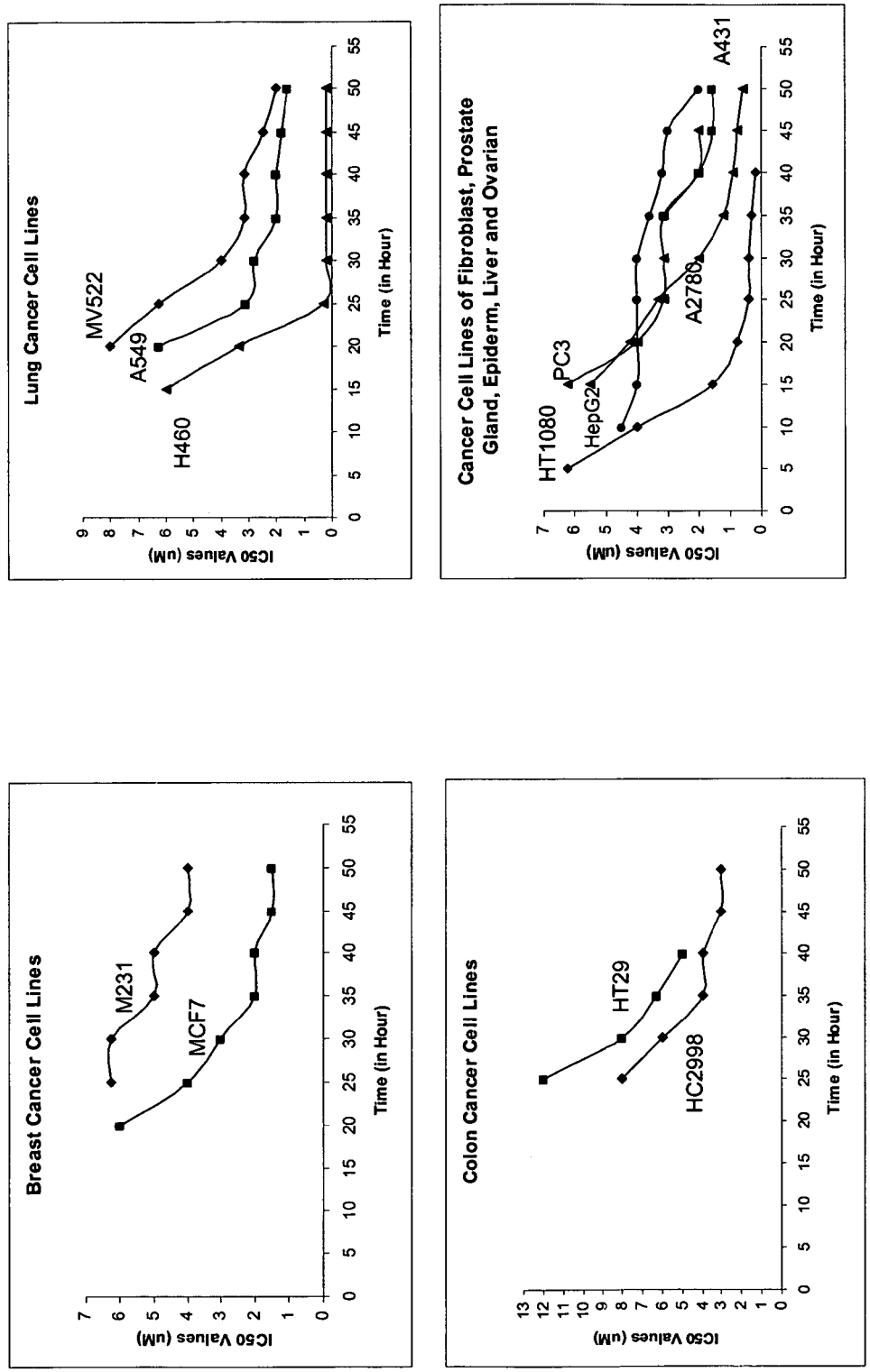
FIG. 15. The time dependent IC values for each compound (15A: Doxorubicin; 15B: Paclitaxel; 15C: Olomoucine; 15D: Tamoxifan) for the indicated cell lines as estimated at 5 hr intervals from the cell index curves obtained using a cell-substrate impedance monitoring system of the present invention.
Figure 15B:
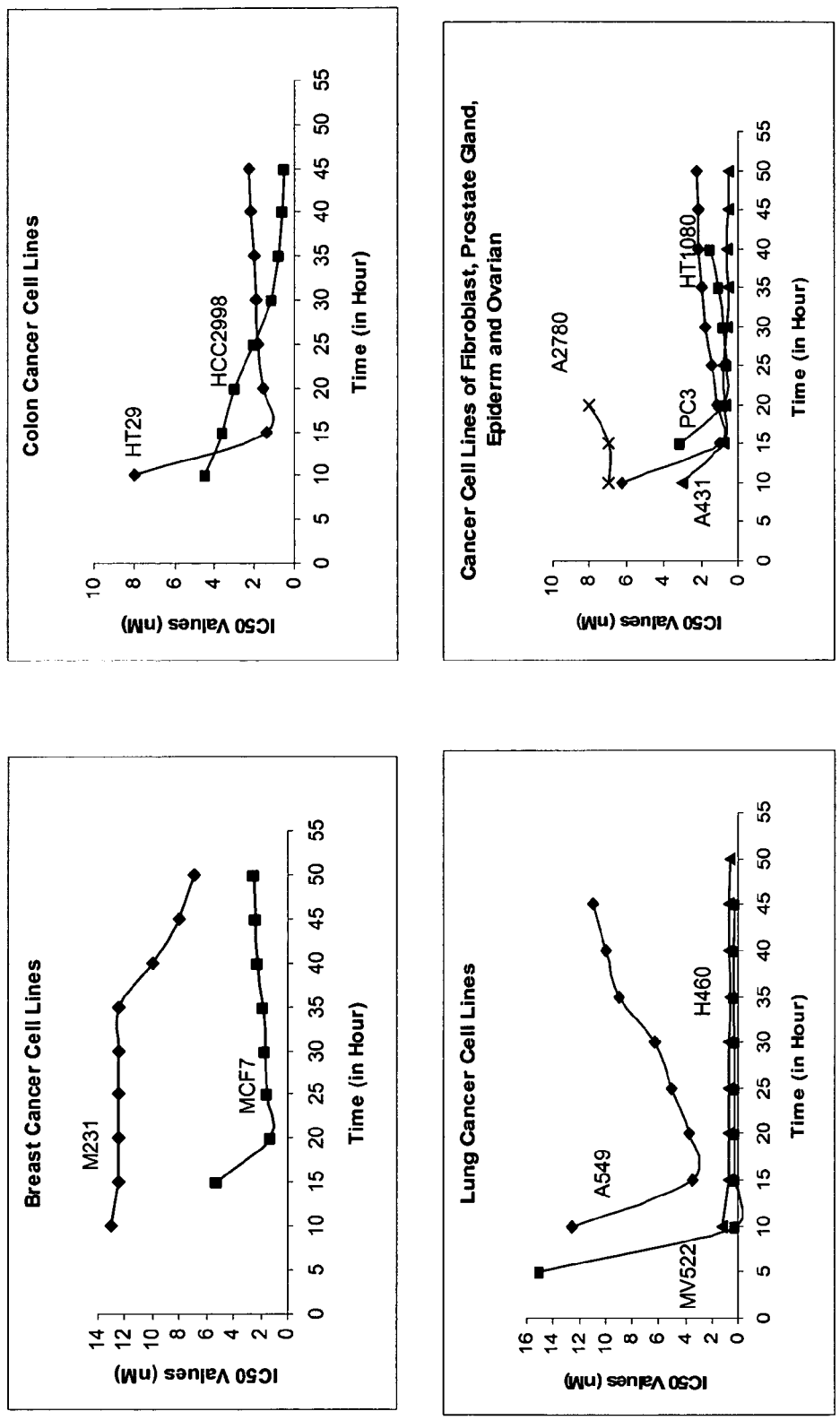
Figure 15C:
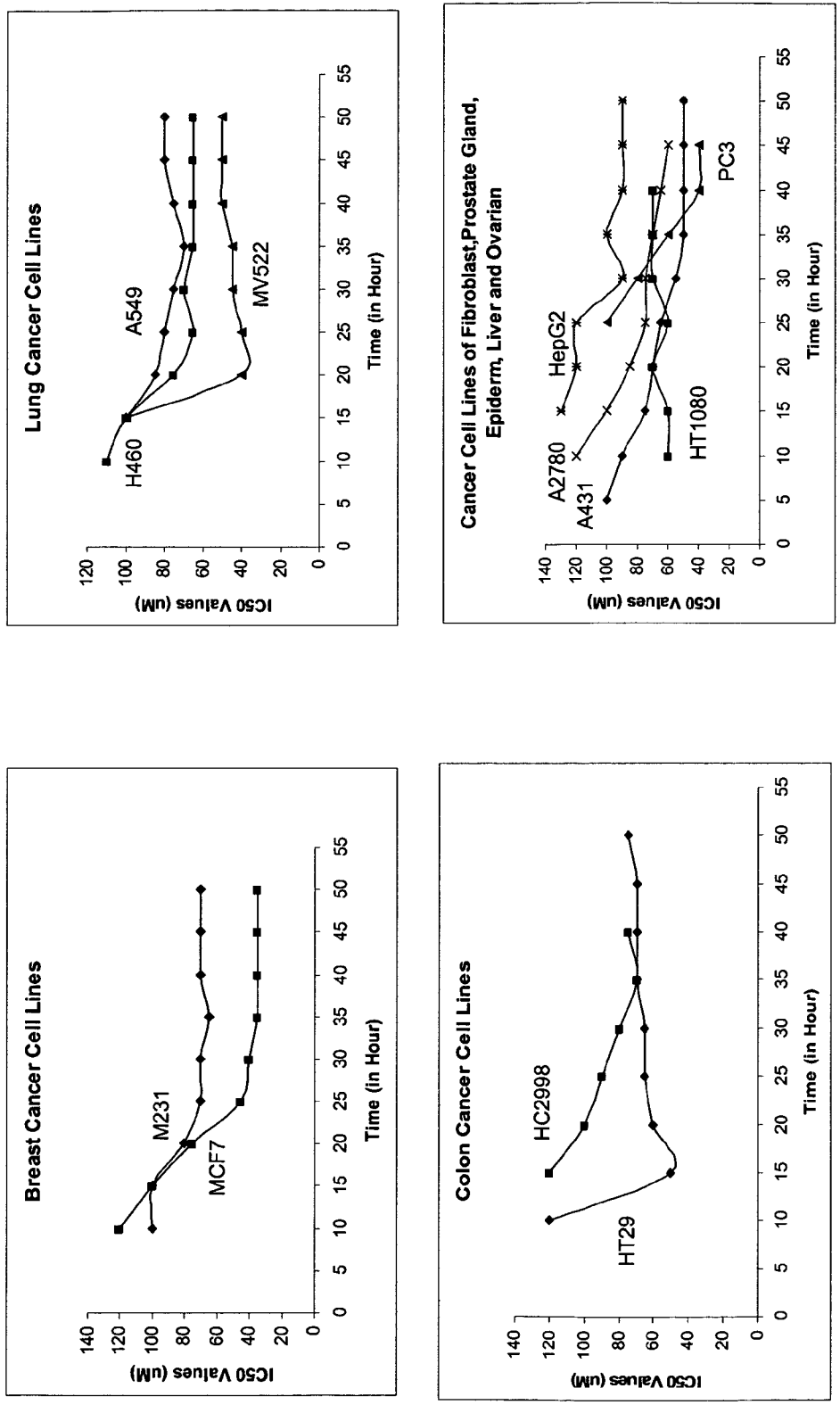
Figure 15D:
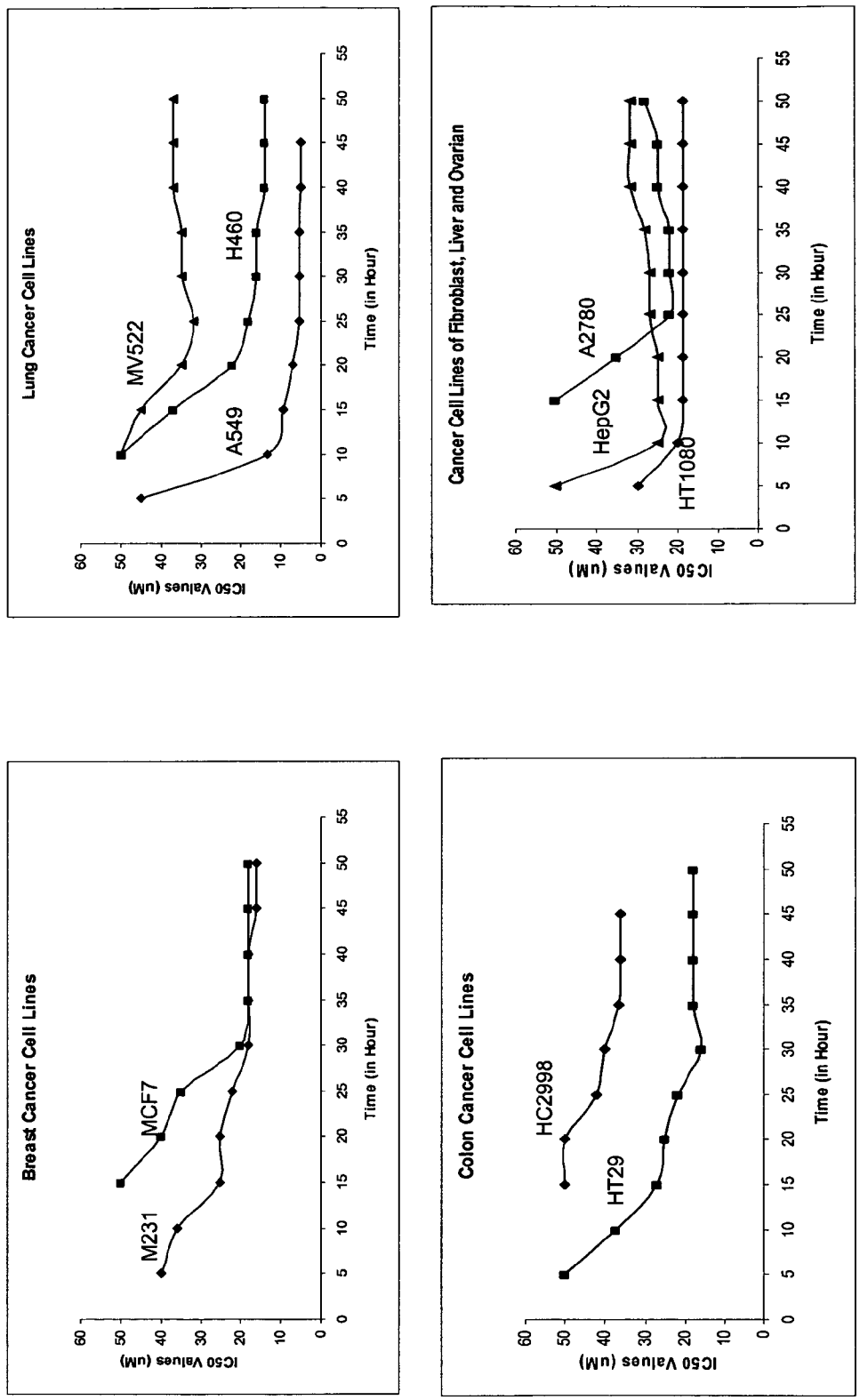
Figure 16B:
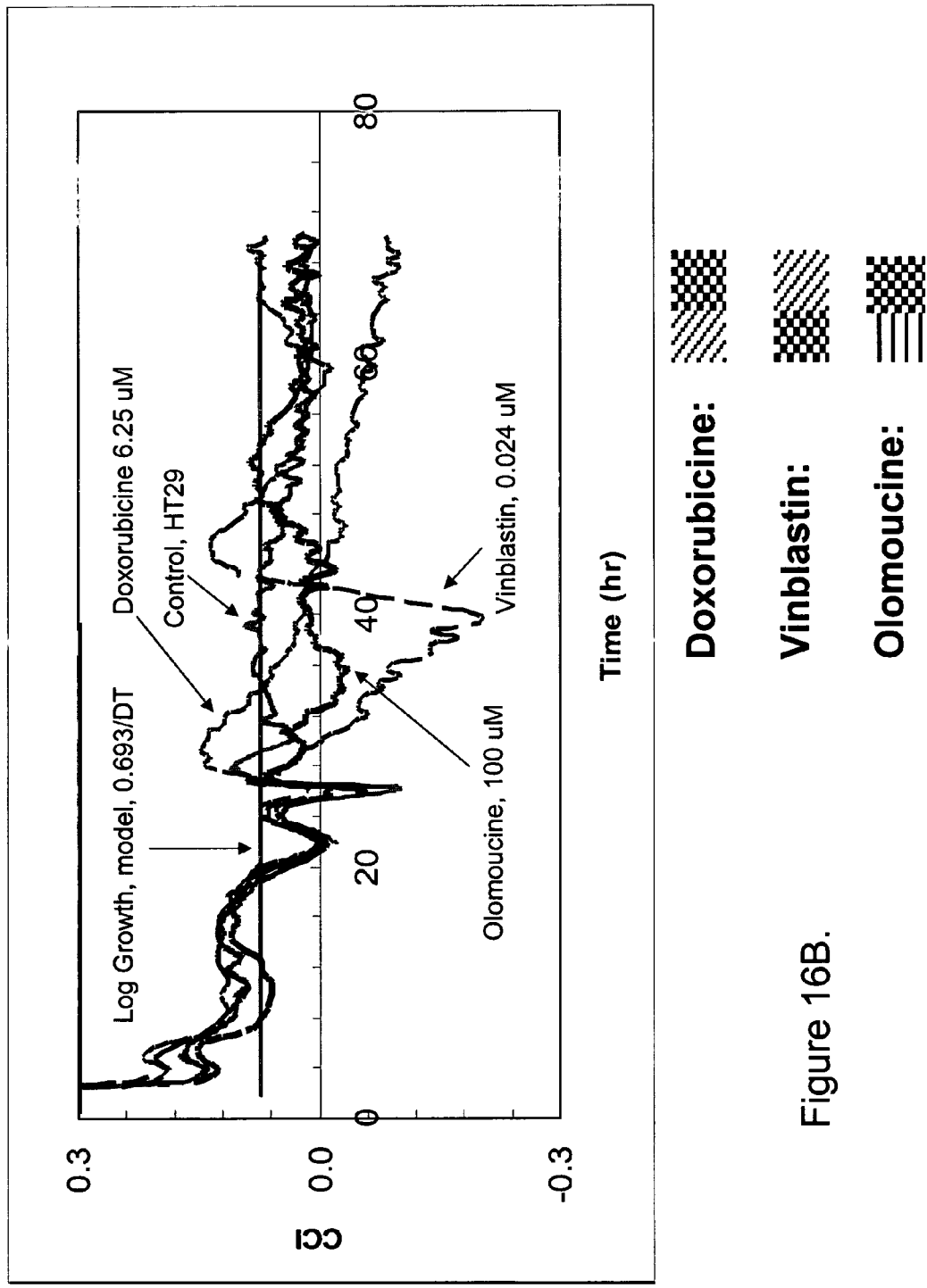
FIG. 16B shows the derived cell change index (CCI) from the cell index curves shown in FIG. 16A. Also shown is the "black-white shading codes" used for different responses based on the convention shown in FIG. 16C.
Figure 16C:
FIG. 16C shows the color-coding scheme used for representing the CCI curves. If the DT is the doubling time for the cells undergoing exponential growth in the cell culture media used, then CCI having different values relative to 0.7/DT indicates the different cell change status. If CCI>>0.7/DT, cell index increases faster than that expected for an exponential growth (or log growth) of the cells (such region n the CCI curve is represented as ▓Rectangle). If CCI is about 0.7/DT, cell index increases in the same rate as that expected for an exponential growth of the cells (such region in the CCI curve is represented as ▓Rectangle). If CCI is more than zero but somewhat smaller than 0.7/DT, then cell index increases in the rate slowed than that expected for an exponential growth (such region of the CCI curve is represented as ▓Rectangle). If CCI is about zero, then cell index shows a near constant value (such region of the CCI curve is represented as ▓Rectangle). If CCI is negative, then the cell index is decreasing with time, showing the cells losing attachment to the electrode surface or changing their morphology (such region of the curve is shown as ▓Rectangle). If CCI is very negative, then the cell index decreases rapidly with time, showing that either cells lose attachment to the electrode surfaces quickly or cells change their morphology very quickly (such region of the CCI curve is represented as ▓Rectangle). The transient, quick noise in the CCI values are removed so that the whole CCI curve is represented after compound addition by one, two or three black/white-shaded rectangles.
Figure 17:
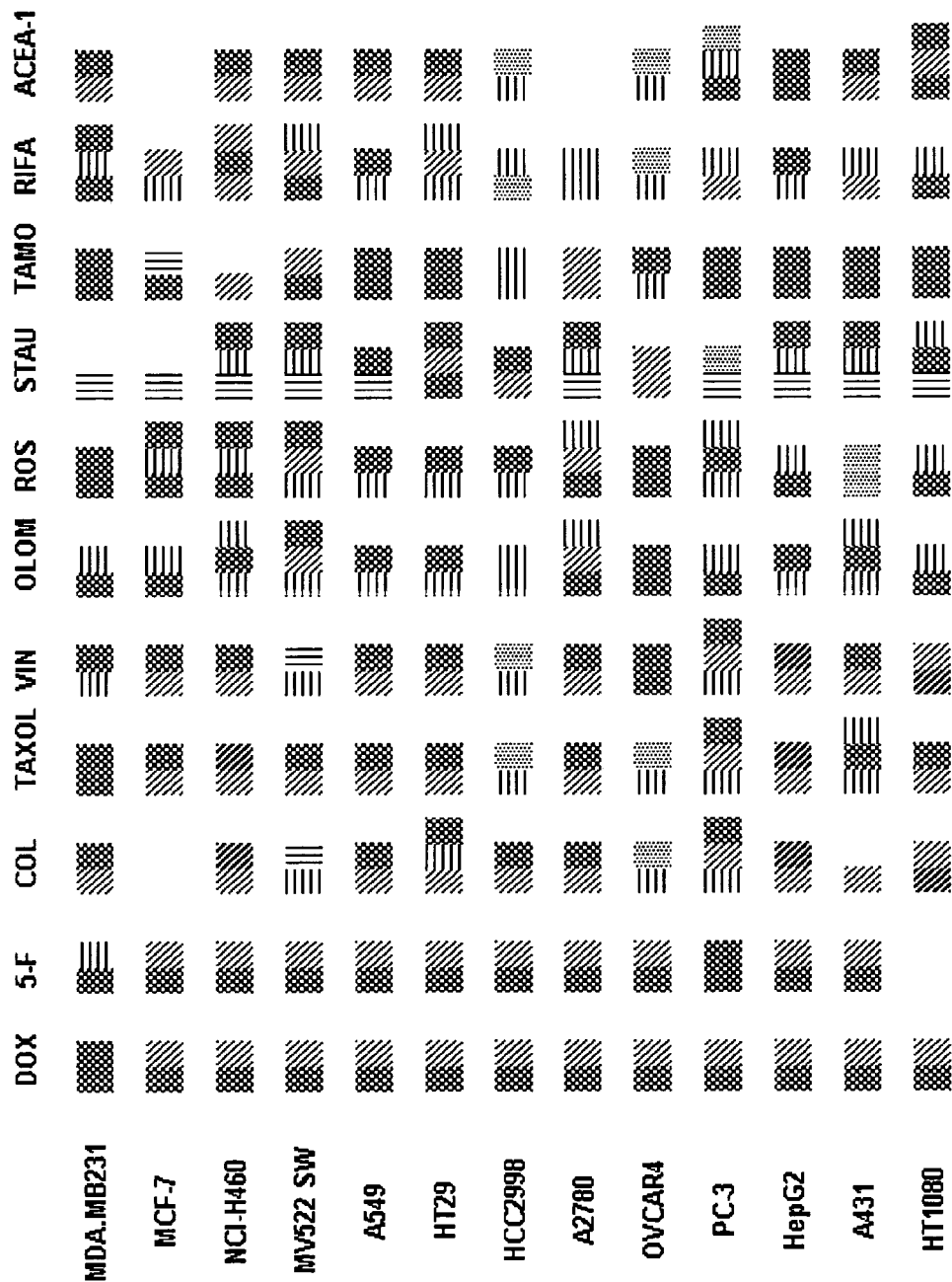
FIG. 17 shows the cell response profile of each cell line tested against the indicated chemotherapeutic agents. For each cell line and compound, the time-dependent cell change index (CCI) was calculated from their corresponding RT-CES responses at an IC50 concentration. (IC 50 is time dependent so that the IC50 concentration at 30 h, or the concentration closest to that, after drug addition is used). The specific CCI curves as related to specific cellular responses were coded according to the convention described in FIG. 16C and displayed in groups of compounds with similar mechanism of action. DOX: doxorubicin; 5-F: 5-Fluorouracil; COL: Colcemid; TAXOL: paclitaxel; VIN: vinblastin; OLOM: Olomoucine; ROS: Roscovitine; STAU: Staurosporine; TAMO: Tamoxifan; RIFA: Rifampicin; ACEA-1: an ACEA test compound.

Profiling of Dynamic Cell Responses to Anti-Cancer Drugs Using ACEA RT-CES System In this study, we used the RT-CES system to dynamically monitor cancer cell responses to chemotherapeutic compounds with characterized mechanisms, and to profile the specific cell response patterns. Thirteen cancer cell lines including cancers of breast, prostate, lung, colon, ovary, kidney, fibroblast, and central nervous system were tested (Table 1). Each cancer cell type was treated with 11 chemotherapeutic compounds, classified as DNA damaging agents, protein kinase inhibitors, anti-mitotic drugs, cell cycle specific inhibitors, protein synthesis inhibitors plus a compound of unknown category (Table 2). Dynamic and dose dependent cell-compound interaction patterns were characterized and summarized for all the tested cell lines and compounds. The profiles for three drugs, doxorubicin, olomoucine and paclitaxel against a panel of 12 different cell lines are presented in FIGS. 9, 10 and 11, respectively. In addition, we characterized the biological effect of these compounds on cells by monitoring cell cycle progression, cell viability and morphological status of the cells in an attempt to correlate specific cellular response to the shape of the cell index trace (FIGS. 12, 13 and 14). Furthermore we calculated the time-dependent IC-50 values for each compound against the various cell lines (FIG. 15) and developed an algorithm to calculate Cell Change Index to profile the dynamic cell response of the different chemotherapeutic agents across the different cell lines. Cell Change Index was calculated for the dynamic RT-CES responses of different cell lines to different chemotherapeutic agents using the definitions described above. Based on the time-dependent values of CCI, each CCI value region across the time scale is represented by black-white shading-based coding. For example, if after compound addition, the CCI value (for a particular cell line under a specific compound treatment at the concentration of IC50 value) is nearly zero for certain period of time and then becomes positive, attaining a value about 0.7/DT (DT is doubling). Then the cell response to this compound is represented as a rectangle followed by a rectangle. Examples of such analysis is shown in FIG. 16. The overall black-white shading-based coding map representing the cell dynamic responses to various compounds is shown in FIG. 17.

In summary of this study, we note that using the RT-CES system to screen chemotherapeutic agents results in unique activity patterns that is dependent on the compound itself, the concentration, length of incubation and the cell type. The "signature" patterns of each drug correlates with specific biological phenomenon such as log growth, cell cycle rest, morphology change and cell death. Cell Change Index was a good parameter derived from RT-CES data to mathematically describe cell changes. Cell response profiling based on CCI value indicates that drugs with similar mechanism of action displays similar patterns. Thus, the similarity in the dynamic cell-compound interaction patterns may indicate similarity in mechanism of action, mode of resistance and possibly molecular targets. The RT-CES system can be readily adapted to high throughput dynamic screening and analysis of anti-cancer compounds and the information-intensive approach presented in this study can be applied to profile existing cancer chemotherapeutic agents, screen new compounds and provide insight into the mechanism of action of anti-cancer agents.

TABLE I

List of cancer cell lines tested against a number of chemical compounds.

| Cancer Cell Line | Organ or Tissue Origin |
| --- | --- |
| MDA.MB231 | Breast Cancer |
| MCF7 | Breast Cancer |
| NCI-H460 | Non-Small Cell Lung Cancer |
| MV522 SW | Non-Small Cell Lung Cancer |
| A549 | Non-Small Cell Lung Cancer |
| HT29 | Colon cancer |
| HCC2998 | Colon cancer |
| A2780 | Ovarian Cancer |
| OVCAR4 | Ovarian Cancer |
| PC-3 | Prostate Cancer |
| HepG2 | Human Hepatosarcoma |
| A431 | Epidermoid Cancer |
| HT1080 | Fibrosarcoma |

TABLE II

List of chemical compounds used in the study of profiling cell dynamic responses to a number of anti-cancer compounds.

| Machanisms of Compound Action Effect on DNA replication or Topology | Chemical Compounds | concentration From High to Low (dilution factor: 2) |
| --- | --- | --- |
| Mitotic Poisons | Doxorubincin | 6.25 uM-0.098 uM |
|  | 5-Fluorouracil | 50 uM-0.78 uM |
|  | Colcemid | 3.125 uM-0.049 uM |
|  | Paclitaxol | 0.0125 uM-0.00019 uM |
|  | Vinblastin | 1.56 uM-0.024 uM |
| Cell Cycle Arrest | Olomoucine | 100 uM-1.56 uM |
|  | Roscovitine | 50 uM-0.78 uM |
| Kinase Inhibitors | Staurosporine | 5 uM-0.078 uM |
|  | Tamoxifan | 50 uM-0.78 uM |
| Protein synthesis Inhibitor | Rifampicin | 100 uM-1.56 uM |
| Unknown type | ACEA-1 |  |

EXAMPLE 2

Cytotoxicity Profiling

Methods

Cells. All the cells used in this study were obtained from ATCC and maintained at 37° C. incubator with 5% $CO_2$ saturation. H460, HepG2 and HT1080 cells were maintained in RPMI media containing 5% FBS and 1% penicillin and streptomycin. NIH3T3 cells were maintained in DMEM media containing 10% FBS and 1% penicillin and streptomycin.

Cell Proliferation Assays. For each of the cell type, the indicated number of cells was seeded per well in 96× microtiter plates (E-Plate™) with incorporated electrode structures in individual wells device in 100 μL of media. The attachment, spreading and proliferation of the cells were continuously monitored every 30 minutes using the RT-CES™ system (a cell-substrate impedance monitoring system. Cell proliferation was monitored for a period of 48-72 hours depending on the experiment. The electronic readout, cell-sensor impedance is displayed as a parameter called Cell Index.

Figure 18:
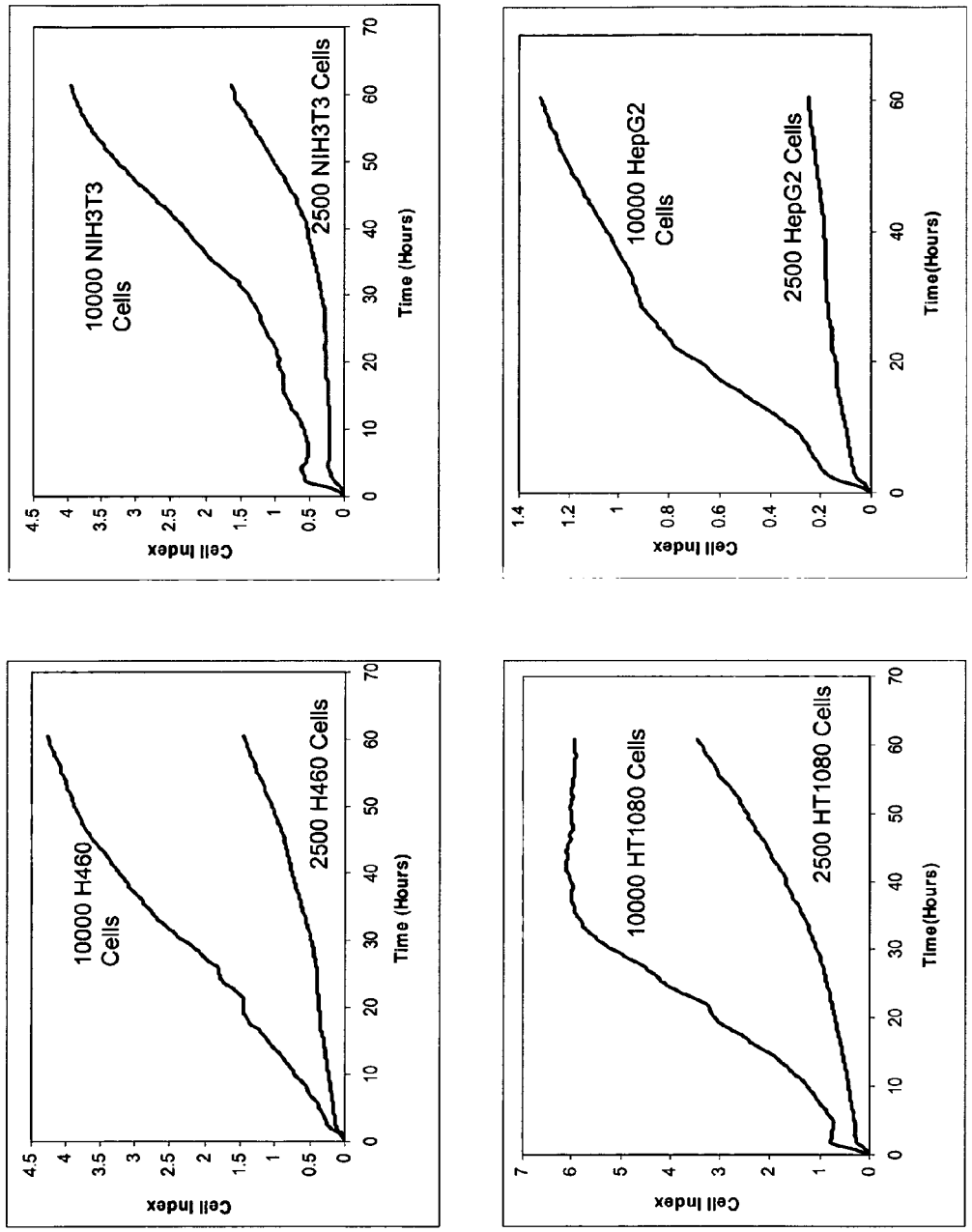
FIG. 18. Dynamic monitoring of cell proliferation. H1080 fibrosarcoma cells, H460 lung cancer cells, HepG2 hepatosarcoma cancer cells and NIH3T3 mouse fibroblast cell lines were seeded at a density of 2500 and 10,000 cells per well of ACEA 96× e-Plate device. The adhesion, spreading and proliferation of the cells were dynamically monitored every 30 minutes using a cell-substrate impedance monitoring system of the present invention.

Drug Treatment and Cytotoxicity Assessment. For each cell type the optimum cell concentration was chosen based on their respective proliferation pattern (FIG. 18). The indicated cell numbers were seeded per well of ACEA's 16× or 96× E-Plate™ (exemplary devices of the present invention) in 100 μL final volume. The attachment, spreading and proliferation of the cells were continuously monitored every 30 minutes using the RT-CES system (an exemplary system of the present invention). Approximately 24 hours after seeding, when the cells were in the log growth phase, the cells were treated with 100 μL of the indicated compounds dissolved in cell culture media. The cells were also treated with DMSO, which served as vehicle control. Depending on the experiment, the final DMSO concentration in the media was in the range of 0.25%-0.5%.

MTT Assay. Increasing numbers of NIH3T3 cells were seeded in 16× e-plate and monitored by RT-CES to obtain the corresponding Cell Index. The media was immediately aspirated and the cells were then assayed by using the standard MTT assay according to the manufacturer's protocol.

Flow Cytometry. A549 cells were seeded at a density of 500,000 cells/well in 60 mm tissue culture dishes. Approximately, 24 hours after seeding, the cells were treated with the indicated final concentration of Olomoucine and 16 hours later the cells were washed with PBS, trypsinized, washed twice with PBS and fixed in 70% methanol and stored at 4° C. until the staining step. The cells were stained with propidium iodide and analyzed by FACS using a wavelength of 488 nm.

Monitoring Dynamic Cell Proliferation in Real-Time Using the RT-CES

In order to assess dynamic cell proliferation using the RT-CES system, H460 human lung cancer cells, H1080 fibrosarcoma cells, HepG2 human hepatosarcoma cells and NIH3T3 mouse fibroblasts were seeded at 2500 and 10,000 cells per well in triplicate in ACEA's 96× E-Plate™. The cells were continuously monitored every 30 minutes using the RT-CES system for the indicated period of time (FIG. 18). As shown in FIG. 18, each cell type has its own characteristic kinetic trace, based on the number of cells seeded, the overall size and morphology of the cells and the degree to which the cells interact with the sensor surface. Also, the adhesion and spreading kinetics as well as time when the cells enter the log growth phase is characteristic of each of the indicated cell lines and therefore offers an excellent internal control and a way to standardize and validate stock cultures during different phases of the manufacturing process.

Figure 19:
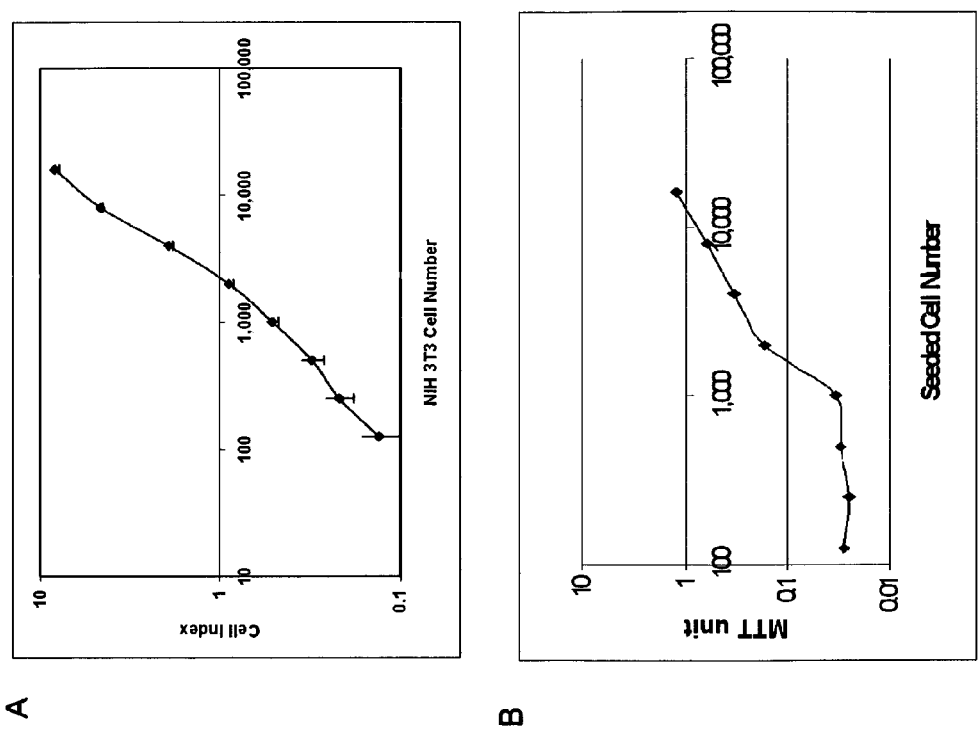
FIG. 19. Correlation between cell-substrate impedance measurement (as shown here, Cell Index) and number of cells seeded and comparison of Cell Index with MTT. (A) Increasing numbers of NIH3T3 ranging from 100 cells all the way up to 10,000 cells were seeded in a device of the present invention and the cells were monitored for 10 hours at which point the Cell Index was obtained. The Cell Index value was plotted against the corresponding number of cells. (B) The cells described in FIG. 19A were assayed by MTT assay at the end of the experiment and the optical density at 590 nm was plotted against the number of cells seeded.

To ascertain that the RT-CES units of Cell Index correlates with the number of the cells in the well, increasing numbers of NIH3T3 cells were seeded in ACEA 16× E-Plate™ and were monitored for up to 10 hours, at which time the Cell Index was acquired. FIG. 19A shows a plot of Cell number seeded versus the Cell Index obtained and indicates that for this particular cell type the RT-CES system could detect as little as 100 cells and the readout is linear by two orders of magnitude all the way up to 10000 cells. In addition, at the end of the experiment described in FIG. 19A, the cells were also assayed by the MTT assay. As shown in FIG. 19B, even at up to 1000 cells the MTT assay is not appreciably different than background values and for cell numbers exceeding 1000, then the MTT units correlates with the number of cells seeded in a linear fashion. However, it is important to remember that while the RT-CES system is capable of dynamic and continuous measurements, for comparative reasons the experiment described in FIG. 19 was only conducted at a single point, since MTT is a single point assay.

Assessment of Drug Interaction with Target Cells Using the RT-CES™ System

To assess drug potency using the RT-CES system, the IC-50 value of Tamoxifen was determined for different cell lines and compared with MTT assay at 48 hours after Tamoxifen addition. According to Table III, the IC-50 values obtained for Tamoxifen for the different cell lines using the RT-CES system is very consistent with the values obtained by the MTT assay, indicating that the RT-CES system can be used to assess the potency of various drugs against different adherent cell lines.

Figure 20:
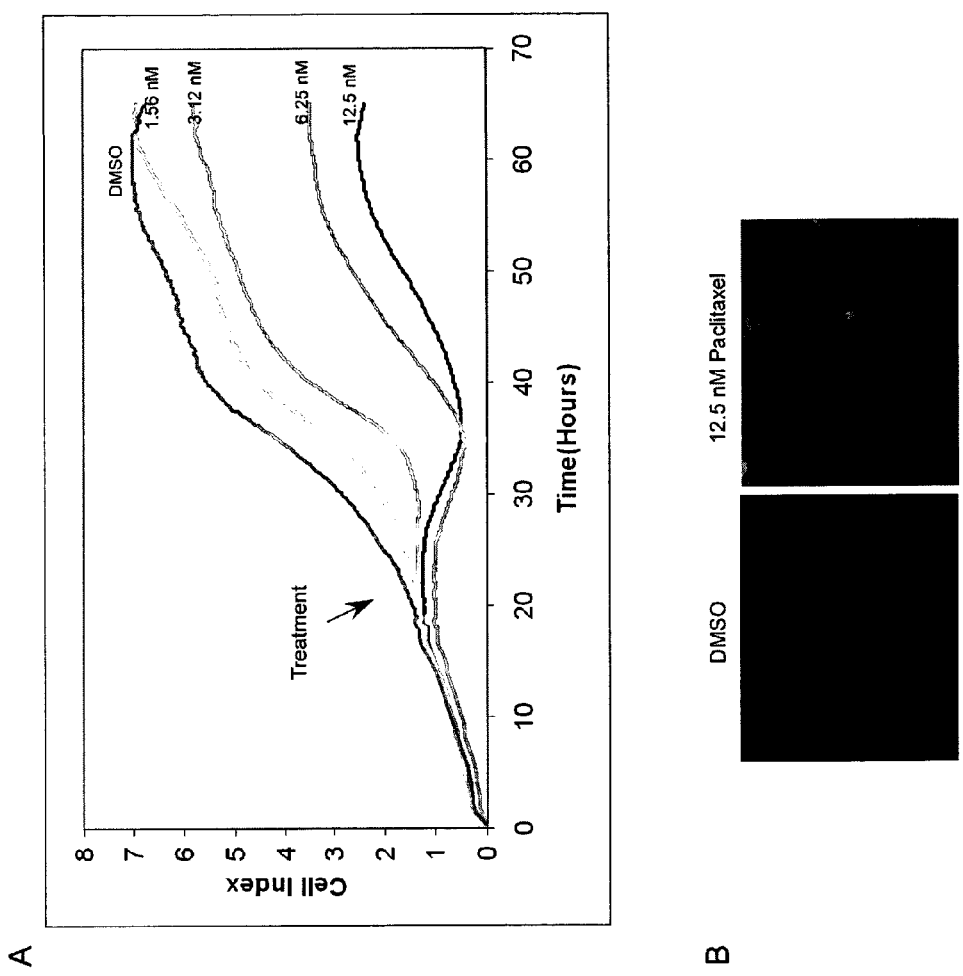
FIG. 20. Dynamic monitoring of drug interaction with target cells using a cell-substrate impedance monitoring system of the present invention. (A) A549 cells were seeded in a device of present invention at a density of 10,000 cells per well and the cells were continuously monitored up to 24 hours at which point paclitaxel was added at the indicated final concentrations. (B) Annexin V staining of A549 cells treated with DMSO or 12.5 nM paclitaxel for 20 hours. The cells were observed with fluorescence microscope and images were captured with an attached digital camera.

In order to observe the kinetics of drug interaction with target cells, A549 non-small lung cancer cells were seeded in ACEA 96× E-Plate™ and continuously monitored until the cells reached the log growth phase at which point different concentrations of paclitaxel were added to the cells at the indicated final concentration. As shown in FIG. 20A, paclitaxel at the highest concentration initially induces a cytotoxic effect which is mainly due to cell death as judged by Annexin V staining (FIG. 20B). Remarkably, the cells recover from the initial cytotoxic effect of the drug and start to re-proliferate. While it remains to be determined if this phenomenon is due to metabolism and inactivation of paclitaxel or due to the emergence of paclitaxel-resistant subpopulation, this experiment clearly exemplifies the tremendous advantage of real-time measurement which is offered by the RT-CES system and allows the user to the opportunity to observe and assess the entire history of drug interaction with the target cells which provides further information in addition to cell viability or cytotoxicity. The phenomenon observed in FIG. 20A would've been easily missed by traditional single-point assays such as MTT.

Figure 21:
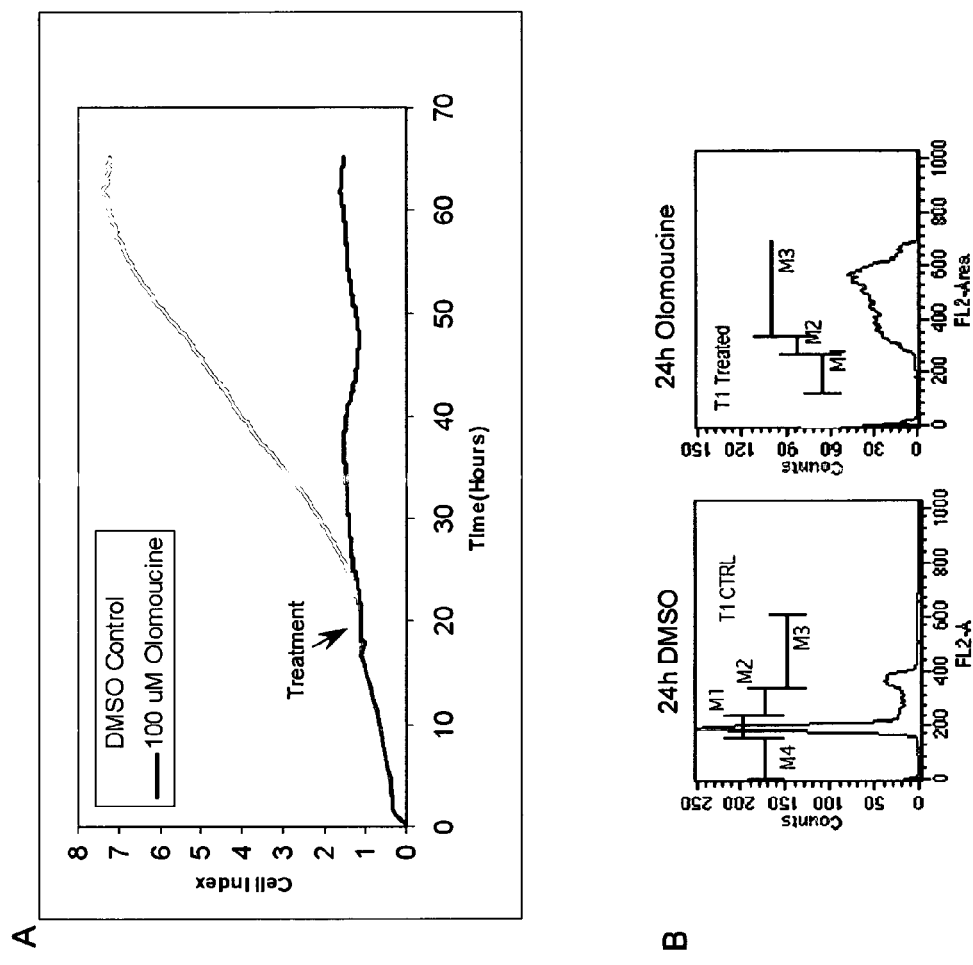
FIG. 21. Dynamic monitoring of cell cycle arrest using a cell-substrate impedance monitoring system of the present invention. A549 cells were seeded in a device of present invention at 10,000 cells per well and continuously monitored using the RT-CES. The cells were treated with either (A) DMSO or 100 μM Olomoucine (B) A549 cells growing on tissue culture dishes for 20 hours were treated with DMSO or 100 μM Olomoucine. Cell cycle analysis was performed by flow cytometry.

Yet another major advantage of using the RT-CES system to continually monitor the interaction of drugs with target cells is that the user can obtain insight into the mechanism of action of the drug of interest. To demonstrate this point, A549 cells were seeded in ACEA 96× microtiter device and continually monitored by the RT-CES. The cells were treated with either DMSO as the vehicle control or with 100 μM Olomoucine which is a CDK inhibitor and induces cell cycle arrest either at G1→S transition or at the G2→M transition, depending on the cell line. As shown in FIG. 21A addition of Olomoucine to exponentially growing A549 cells causes the trace of the Cell Index recordings of the cells to level off and remain in a steady state that is reminiscent of cell cycle block, where the cells are neither proliferating nor dying off. The control cells treated with DMSO continue to proliferate until they reach confluence, at which time they are contact inhibited and the Cell Index recording levels off. To demonstrate that the effect of Olomoucine on A549 cells as monitored by the RT-CES was indeed due to an arrest of the cell cycle, A549 cells growing on tissue culture dish were treated with the same concentrations of DMSO and Olomoucine and subjected to flow cytometry analysis. As shown in FIG. 21B, the flow cytometry analysis indicates that treatment of A549 cells with the indicated concentration of Olomoucine induces cell cycle arrest at the G2→M transition, where CDKs such as CDK2 is active. Taken together, using the RT-CES system to dynamically monitor drug interaction with the target cells offers the user the opportunity to understand the mechanism of drug action and its mode of interaction with the target cell.

In order to assess the RT-CES system for analysis of cytotoxicity, the interaction of A549 cells was examined with cytotoxic agents with different mechanism of action. FIG. 22 shows the characteristic trace of A549 cells monitored by RT-CES™ and treated with different concentrations of 5-fluorouracil, vinblastine and staurosporine. According to FIG. 22, dynamic monitoring of the interaction of the indicated cytotoxic agents leads to the generation of characteristic kinetic patterns that is dependent on the cellular background, the concentration of the drug, the duration of exposure and the mechanism of drug action. Since each compound has its own characteristic pattern, these kinetic traces could potentially be used to determine the mechanism of action of compounds with unknown targets by comparing the kinetic profile to the profile of compounds with known mechanism of action.

Label-free and dynamic monitoring of cell proliferation, viability and cytotoxicity using the RT-CES system offers very distinct and important advantages over traditional end-point assays. It allows for built in internal quality control to assure consistency and reproducibility between the different assays. Dynamic monitoring allows for observation of the entire episode of drug interaction with target cells and the user can therefore have a better understanding of the mode and mechanism of drug interaction. Furthermore, the actual kinetic trace of the drug interaction with the target cell is very significant because it can offer clues as to the mechanism of drug interaction with the target cell. Finally, since each compound or drug has its own characteristic profile with respect to its interaction with target cells, the RT-CES system can be used as a way to determine the mechanism of action of drugs with unknown targets.

Table III. Comparison of IC-50 values for Tamoxifen treatment of different cancer cell lines using the RT-CES system versus MTT assay. The indicated cell lines were seeded in ACEA 16× devices and monitored by RT-CES. Approximately 24 hours later, the cells were treated with increasing concentrations of Tamoxifen and then continually monitored by RT-CES. The experiment was stopped about 48 hours later and the cells in the 16× devices were assayed by using MTT. The IC-50 values derived from RT-CES system are time-dependent. In the table, the IC-50 values at about 48 hrs after compound treatment are shown for RT-CES system determination and MTT assay.

| Cell Type | RT-CES ™ | MTT Assay |
|---|---|---|
| HT1080 | 22.4 µM | 30.0 µM |
| NIH3T3 | 16.0 µM | 19.0 µM |
| HepG2 | 15.2 µM | 16.2 µM |
| HUEVEC | 7.5 µM | 8.0 µM |

All of the references cited herein, including patents, patent applications, and publications, and including references cited in the Bibliography, are incorporated by reference in their entireties.

Headings are for the convenience of the reader and do not limit the scope of the invention.

We claim:

1. A device for monitoring cell-substrate impedance, comprising:
 a) a nonconducting substrate;
 b) two or more electrode arrays fabricated on a same plane of said substrate, wherein each of said two or more electrode arrays comprises two electrode structures and the electrode structures of each of said two or more electrode arrays have substantially the same surface area;
 c) two or more fluid containers on said substrate, wherein each of said two or more arrays is associated with one of said two or more fluid containers; and
 d) at least two connection pads:
 wherein for each of said two or more electrode arrays, each of said two electrode structures comprises multiple electrode elements and said multiple electrode elements of each of said two electrode structures are connected to an electrode bus, further wherein the first of said two electrode structures of each of said at least two electrode arrays is connected to one of said at least two connection pads from a first electrode bus via an electrically conductive trace, and the second of said two electrode structures of each of said at least two electrode arrays is connected to another of said at least two connection pads from a second electrode bus via another electrically conductive trace, further wherein each array is individually addressed;
 further wherein for at least two of said two or more electrode arrays, each of which has a first electrode structure that is connected to a common connection pad from the first electrode bus via the electrically conductive trace and a second electrode structure that is connected to an independent connection pad from the second electrode bus via the another electrically conductive trace;
 further wherein electrode buses are positioned at ends of electrically conductive traces and not within electrically conductive traces as trace segments; and
 further wherein said substrate has a surface suitable for cell attachment or growth; wherein said cell attachment or growth on said substrate can result in a detectable change in impedance between or among said electrode structures within each electrode array.

2. A system for monitoring cell-substrate impedance, comprising:
 a) one or more devices of claim 1, wherein said at least two fluid containers are two or more wells, wherein at least two of said two or more wells of said device comprise an electrode array at the bottom of the well, wherein said electrode array is individually addressed, further wherein said device can be used to measure differences in impedance values that relate to cell behavior;
 b) an impedance analyzer;
 c) a device station comprising electronic circuitry that can engage said device and selectively connect said two or more electrode arrays of said device to said impedance analyzer; and
 d) a software program that can control said device station and record and analyze data obtained from said impedance analyzer.

3. The device according to claim 1, wherein said nonconducting substrate comprises silicon dioxide on silicon, silicon-on-insulator (SOI) wafer, glass, sapphire, ceramic, polymer, fiber glass, or plastic.

4. The device according to claim 3, wherein said plastic is selected from the group consisting of polyimide, polystyrene, polycarbonate, polyvinyl chloride, polyester, polypropylene and urea resin.

5. The device according to claim 1, wherein said electrode elements of the array are of approximately equal widths.

6. The device according to claim 5, wherein said electrode elements of the array are greater than 30 microns in width.

7. The device according to claim 5, wherein said electrode elements of the array are from about 50 to about 300 microns in width.

8. The device according to claim 1, wherein said electrode elements are approximately evenly spaced.

9. The device according to claim 8, wherein gaps between said electrode elements are less than 50 microns.

10. The device according to claim 1, wherein gaps between said electrode elements are less than 50 microns.

11. The device according to claim 1, wherein each fluid container forms a well, further wherein the device is a multi-well device.

12. The device according to claim 11, wherein said multi-well device comprises between 2 and 1536 wells.

13. The device according to claim 12, wherein said multi-well device comprises between 4 and 384 wells.

14. The device according to claim 11, wherein said multi-well device is formed from a bottomless plate having a well diameter from about 1 millimeter to about 20 millimeters.

15. The device according to claim 14, wherein said well diameter is from about 2 millimeters to about 8 millimeters.

16. The system according to claim 2, wherein said software determines a cell index (CI) or cell change index (CCI) from said data.

17. The system according to claim 2, wherein said software generates a dose response curve from said data.

18. The system according to claim 2, wherein the system monitors cell-substrate impedance at a single frequency or at multiple frequencies.

19. A method of performing an assay to evaluate the effect of one or more test compounds on cells, comprising:
  a) providing the cell-substrate impedance monitoring system of claim 2;
  b) adding cells to two or more wells of said system;
  c) adding different concentrations of a test compound to said two or more wells comprising cells to form two or more compound wells comprising different concentrations of said test compound;
  d) providing at least one additional well as a control well to which cells are added that does not receive test compound;
  e) monitoring impedance from said two or more test compound wells and said at least one control well to obtain impedance measurements at least one time point before the addition of different concentrations of said test compound to said compound wells and at three or more time points after adding said different concentrations of said test compound to said three or more compound wells; and
  f) analyzing said impedance measurements from said two or more compound wells and said at least one control well to evaluate the effect of said test compound on cells.

* * * * *